(12) United States Patent
Hyde et al.

(10) Patent No.: US 8,979,885 B2
(45) Date of Patent: Mar. 17, 2015

(54) DEVICES, SYSTEMS, AND METHODS TO CONTROL STOMACH VOLUME

(75) Inventors: Roderick A. Hyde, Redmond, WA (US); Michael A. Smith, Phoenix, AZ (US); Elizabeth A. Sweeney, Seattle, WA (US); Lowell L. Wood, Jr., Bellevue, WA (US); Richard N. Zare, Stanford, CA (US)

(73) Assignee: Elwha LLC, Bellevue, WA (US)

( * ) Notice: Subject to any disclaimer, the term of this patent is extended or adjusted under 35 U.S.C. 154(b) by 313 days.

(21) Appl. No.: 13/385,572

(22) Filed: Feb. 24, 2012

(65) Prior Publication Data

US 2013/0226217 A1     Aug. 29, 2013

Related U.S. Application Data

(63) Continuation-in-part of application No. 13/385,570, filed on Feb. 24, 2012, and a continuation-in-part of application No. 13/385,574, filed on Feb. 24, 2012.

(51) Int. Cl.
*A61M 29/00* (2006.01)
*A61F 5/00* (2006.01)

(52) U.S. Cl.
CPC ....... *A61F 5/0073* (2013.01); *A61F 2005/0016* (2013.01)
USPC ...................................................... 606/191

(58) Field of Classification Search
CPC ............... A61B 17/12022; A61B 17/12027; A61B 17/12036; A61B 17/1204; A61B 17/12099; A61B 17/12131; A61B 17/12168; A61B 17/12172; A61B 17/12177; A61B 17/12181; A61B 17/12186; A61B 17/1219; A61F 5/0003; A61F 5/0006; A61F 5/0013; A61F 5/003; A61F 5/0033; A61F 5/0036; A61F 5/004; A61F 5/0043; A61F 5/0046; A61F 5/0073
USPC ............. 600/37; 604/8, 9, 104–109; 606/191; 623/23.64, 23.68
See application file for complete search history.

(56) References Cited

U.S. PATENT DOCUMENTS

| | | | |
|---|---|---|---|
| 4,133,315 A | | 1/1979 | Berman et al. |
| 4,371,814 A | | 2/1983 | Hannas |
| 4,607,618 A | * | 8/1986 | Angelchik .................... 128/898 |

(Continued)

FOREIGN PATENT DOCUMENTS

| | | |
|---|---|---|
| CA | 1324303 | 11/1993 |
| WO | WO 2010/042063 A1 | 4/2010 |

OTHER PUBLICATIONS

PCT International Search Report; International App. No. PCT/US13/26786; Jul. 8, 2013; pp. 1-4.

(Continued)

*Primary Examiner* — Ryan Severson

(57) ABSTRACT

Embodiments disclosed herein relate to methods, devices, and computer systems thereof for reducing stomach volume in a subject. In certain embodiments, a subject receives a stomach-volume-reducing device that optionally includes at least one reservoir configured to release at least one appetite suppressant. In an embodiment, the stomach-volume-reducing device is responsive to one or more environmental conditions of the subject, for example, pH or chemical chemicals in the stomach of the subject. In an embodiment, the stomach-volume-reducing device controls hunger in the subject.

44 Claims, 31 Drawing Sheets

(56) References Cited

U.S. PATENT DOCUMENTS

| | | | |
|---|---|---|---|
| 4,703,756 A | 11/1987 | Gough et al. | |
| 4,930,535 A | 6/1990 | Rinehold | |
| 5,084,061 A | 1/1992 | Gau et al. | |
| 5,112,614 A | 5/1992 | Magruder et al. | |
| 5,129,915 A | 7/1992 | Cantenys | |
| 5,259,399 A | 11/1993 | Brown | |
| 5,331,450 A | 7/1994 | Heep et al. | |
| 5,338,625 A | 8/1994 | Bates et al. | |
| 5,359,448 A | 10/1994 | Laszlo et al. | |
| 5,571,152 A | 11/1996 | Chen et al. | |
| 5,582,170 A | 12/1996 | Soller | |
| 5,603,820 A | 2/1997 | Malinski et al. | |
| 6,210,326 B1 | 4/2001 | Ehwald | |
| 6,217,906 B1 | 4/2001 | Gumucio et al. | |
| 6,234,973 B1 | 5/2001 | Meador et al. | |
| 6,268,161 B1 | 7/2001 | Han et al. | |
| 6,271,278 B1 | 8/2001 | Park et al. | |
| 6,280,604 B1 | 8/2001 | Allen et al. | |
| 6,287,452 B1 | 9/2001 | Allen et al. | |
| 6,436,069 B1 * | 8/2002 | Jellie | 604/107 |
| 6,442,413 B1 | 8/2002 | Silver | |
| 6,450,946 B1 | 9/2002 | Forsell | |
| 6,454,759 B2 | 9/2002 | Krulevitch et al. | |
| 6,514,689 B2 | 2/2003 | Han et al. | |
| 6,546,268 B1 | 4/2003 | Ishikawa et al. | |
| 6,579,301 B1 | 6/2003 | Bales et al. | |
| 6,733,512 B2 | 5/2004 | McGhan | |
| 6,764,446 B2 | 7/2004 | Wolinsky et al. | |
| 6,818,356 B1 | 11/2004 | Bates | |
| 6,823,717 B2 | 11/2004 | Porter et al. | |
| 6,965,791 B1 | 11/2005 | Hitchcock et al. | |
| 6,981,980 B2 | 1/2006 | Sampson et al. | |
| 6,994,934 B2 | 2/2006 | Stanish et al. | |
| 7,025,734 B1 | 4/2006 | Ellis et al. | |
| 7,044,911 B2 | 5/2006 | Drinan et al. | |
| 7,066,945 B2 * | 6/2006 | Hashiba et al. | 606/191 |
| 7,074,423 B2 | 7/2006 | Fereira et al. | |
| 7,105,352 B2 | 9/2006 | Asher et al. | |
| 7,110,803 B2 | 9/2006 | Shults et al. | |
| 7,144,655 B2 | 12/2006 | Jenson et al. | |
| 7,162,289 B2 | 1/2007 | Shah et al. | |
| 7,168,294 B2 | 1/2007 | Porter et al. | |
| 7,181,261 B2 | 2/2007 | Silver et al. | |
| 7,189,471 B2 | 3/2007 | Jankowksi et al. | |
| 7,194,801 B2 | 3/2007 | Jenson et al. | |
| 7,205,701 B2 | 4/2007 | Liu et al. | |
| 7,206,605 B2 | 4/2007 | Hattori | |
| 7,215,887 B2 | 5/2007 | Ternullo et al. | |
| 7,218,900 B2 | 5/2007 | Suzuki | |
| 7,227,956 B1 | 6/2007 | Onishi | |
| 7,236,595 B1 | 6/2007 | Bean et al. | |
| 7,236,821 B2 | 6/2007 | Cates et al. | |
| 7,238,628 B2 | 7/2007 | Demaray et al. | |
| 7,245,894 B2 | 7/2007 | Sekiguchi et al. | |
| RE39,785 E | 8/2007 | Fuse | |
| 7,254,160 B2 | 8/2007 | Kawamoto et al. | |
| 7,257,327 B2 | 8/2007 | Small | |
| 7,260,155 B2 | 8/2007 | Stonick et al. | |
| 7,260,402 B1 | 8/2007 | Ahmed | |
| 7,260,764 B2 | 8/2007 | Chen | |
| 7,260,768 B1 | 8/2007 | Matsumoto et al. | |
| 7,291,503 B2 | 11/2007 | Swager | |
| 7,798,954 B2 | 9/2010 | Birk et al. | |
| 7,854,745 B2 | 12/2010 | Brister et al. | |
| 7,919,112 B2 | 4/2011 | Pathak et al. | |
| 7,919,293 B2 | 4/2011 | Sung et al. | |
| 7,931,693 B2 | 4/2011 | Binmoeller | |
| 8,021,384 B2 | 9/2011 | Weiss et al. | |
| 8,066,780 B2 * | 11/2011 | Chen et al. | 623/23.65 |
| 8,092,479 B2 * | 1/2012 | Albrecht et al. | 606/191 |
| 8,162,969 B2 | 4/2012 | Brister et al. | |
| 8,182,441 B2 * | 5/2012 | Swain et al. | 604/9 |
| 8,216,266 B2 * | 7/2012 | Hively | 606/192 |
| 8,267,888 B2 * | 9/2012 | Marco et al. | 604/104 |
| 8,282,666 B2 * | 10/2012 | Birk | 606/192 |
| 8,287,562 B2 * | 10/2012 | Kasic, II | 606/192 |
| 8,628,553 B2 * | 1/2014 | Voegele et al. | 606/191 |
| 2001/0051766 A1 * | 12/2001 | Gazdzinski | 600/309 |
| 2003/0027240 A1 * | 2/2003 | Asher et al. | 435/25 |
| 2003/0066536 A1 | 4/2003 | Forsell | |
| 2003/0078611 A1 * | 4/2003 | Hashiba et al. | 606/191 |
| 2003/0171768 A1 * | 9/2003 | McGhan | 606/191 |
| 2004/0186502 A1 * | 9/2004 | Sampson et al. | 606/191 |
| 2005/0143787 A1 | 6/2005 | Boveja et al. | |
| 2006/0024813 A1 | 2/2006 | Warthoe | |
| 2006/0241748 A1 | 10/2006 | Lee et al. | |
| 2006/0247722 A1 | 11/2006 | Maschino et al. | |
| 2006/0280307 A1 | 12/2006 | Ikushima et al. | |
| 2007/0016262 A1 | 1/2007 | Gross et al. | |
| 2007/0078476 A1 * | 4/2007 | Hull et al. | 606/191 |
| 2007/0100368 A1 | 5/2007 | Quijano et al. | |
| 2007/0123809 A1 | 5/2007 | Weiss et al. | |
| 2007/0265645 A1 | 11/2007 | Birk et al. | |
| 2008/0058887 A1 | 3/2008 | Griffin et al. | |
| 2008/0065136 A1 | 3/2008 | Young | |
| 2008/0109027 A1 * | 5/2008 | Chen et al. | 606/191 |
| 2008/0208135 A1 * | 8/2008 | Annunziata | 604/175 |
| 2008/0208239 A1 * | 8/2008 | Annunziata | 606/191 |
| 2008/0234718 A1 * | 9/2008 | Paganon et al. | 606/192 |
| 2008/0249635 A1 * | 10/2008 | Weitzner et al. | 623/23.65 |
| 2008/0319506 A1 | 12/2008 | Cauller | |
| 2009/0012553 A1 * | 1/2009 | Swain et al. | 606/191 |
| 2009/0192535 A1 * | 7/2009 | Kasic, II | 606/157 |
| 2010/0114141 A1 * | 5/2010 | Albrecht et al. | 606/191 |
| 2010/0114142 A1 * | 5/2010 | Albrecht et al. | 606/191 |
| 2010/0114143 A1 * | 5/2010 | Albrecht et al. | 606/191 |
| 2010/0114145 A1 * | 5/2010 | Albrecht et al. | 606/191 |
| 2010/0222642 A1 * | 9/2010 | Trovato | 600/37 |
| 2010/0249822 A1 * | 9/2010 | Nihalani | 606/191 |
| 2010/0249825 A1 * | 9/2010 | Nihalani | 606/198 |
| 2010/0324358 A1 | 12/2010 | Birk et al. | |
| 2011/0196197 A1 * | 8/2011 | Forsell | 600/37 |
| 2011/0319924 A1 * | 12/2011 | Cole et al. | 606/192 |
| 2012/0041463 A1 * | 2/2012 | Forsell | 606/191 |
| 2012/0089170 A1 * | 4/2012 | Dominguez | 606/192 |
| 2012/0095385 A1 * | 4/2012 | Dominguez et al. | 604/9 |
| 2012/0191123 A1 * | 7/2012 | Brister et al. | 606/191 |
| 2012/0323160 A1 * | 12/2012 | Babkes | 604/9 |
| 2013/0296764 A1 * | 11/2013 | Stack et al. | 604/9 |
| 2014/0025031 A1 * | 1/2014 | Lam | 604/500 |
| 2014/0066967 A1 * | 3/2014 | Levy et al. | 606/191 |
| 2014/0066968 A1 * | 3/2014 | Pavlovic et al. | 606/191 |

OTHER PUBLICATIONS

Bertleff et al.; "Comparison of Closure of Gastric Perforation Ulcers With Biodegradable Lactide-Glycolide-Caprolactone or Omental Patches"; JSLS; 2009; pp. 550-554; vol. 13; Society of Laparoendoscopic Surgeons, Inc.

Chaudhri et al.; "Gastrointestinal hormones regulating appetite"; Phil. Trans. R. Soc. B; 2006; pp. 1187-1209; vol. 361; The Royal Society.

Geliebter et al.; "Clinical trial of silicone-rubber gastric balloon to treat obesity"; Int J Obes.; Apr. 1991; pp. 259-266; vol. 15, No. 4 (Abstract only).

Gupta et al.; "Preparation and characterization of superporous hydrogels as gastroretentive drug delivery system for rosiglitazone maleate"; DARU; 2010; pp. 200-210; vol. 18, No. 3.

Hoffman, Allan S.; "Bioconjugates of Intelligent Polymers and Recognition Proteins for Use in Diagnostics and Affinity Separations"; Clinical Chemistry; 2000; pp. 1478-1486; vol. 46, No. 9; American Association for Clinical Chemistry.

Imaz et al.; "Safety and Effectiveness of the Intragastric Balloon for Obesity. A Meta-Analysis"; Obes Surg; 2008; pp. 841-846; vol. 18; Springer Science + Business Media B.V.

Kumar et al.; "Study of fiber optic sugar sensor"; PRAMANA—journal of physics; Aug. 2006; pp. 383-387; vol. 67, No. 2; Indian Academy of Sciences.

Lendlein et al.; "Light-induced shape-memory polymers"; Nature; Apr. 14, 2005; pp. 879-882; vol. 434; Nature Publishing Group.

(56) References Cited

OTHER PUBLICATIONS

Low et al.; "Microactuators toward microvalves for responsive controlled drug delivery"; Sensors and Actuators B: Chemical; Aug. 10, 2000, pp. 149-160; vol. 67, Issues 1-2; Elsevier Science S.A.

Malinski et al.; "Monitoring Metal Concentrations in Tissues and Single Cells Using Ultramicrosensors"; Environ Health Perspect; Sep. 1994; pp. 147-151; vol. 102, Suppl 3.

Martin et al.; "The Lipid-Sensor Candidates CD36 and GPR120 are Differentially Regulated by Dietary Lipids in Mouse Taste Buds: Impact on Spontaneous Fat Preference"; PLoS ONE; Aug. 2011; pp. 1-10; vol. 6, No. 8.

"MIP implantable, The new generation of implantable pumps"; Mip Technical Specifications; one page; printed on Jun. 11, 2011; located at www.debiotech.com/products/msys/mip_page_2.html.

Podual et al.; "Preparation and dynamic response of cationic copolymer hydrogels containing glucose oxidase"; Polymer; 2000; pp. 3975-3983; vol. 41, Elsevier Science Ltd.

Preejith et al.; "Total protein measurement using a fiber-optic evanescent wave-based biosensor"; Biotechnology Letters; 2003; pp. 105-110; vol. 25; Kluwer Academic Publishers.

Sofla et al.; "Shape morphing hinged truss structures"; Smart Mater. Struct.; 2009; pp. 1-8; vol. 18; IOP Publishing Ltd.

Swanström et al; "Natural Orifice Transluminal Endoscopic Surgery: The Future of Gastrointestinal Surgery"; The Permanente Journal; Spring 2008; pp. 42-47; vol. 12, No. 2.

"TERIS Procedure"; one page; printed on Nov. 8, 2011; located at www.barosense.com/patients_TERIS_procedure.html; Barosense, Inc.

Thornton et al.; "Enzyme responsive polymer hydrogel beads"; Chem. Commun.; 2005; pp. 5913-5915; The Royal Society of Chemistry.

"TOGA U.S. Clinical Trial"; two pages; printed on Nov. 8, 2011; located at www.satietyinc.com/toga-clinical-trial/overview/; Satiety, Inc.

Tsesmeli et al.; "Review of endoscopic devices for weight reduction: old and new balloons and implantable prostheses"; Endoscopy; 2009; pp. 1082-1089; vol. 41.

Tu et al.; "A Novel Electrochemical Microsensor for Nitric Oxide Based on Electropolymerized Film of $o$-Aminobenzaldehyde-ethylene-diamine Nickel"; Electroanalysis; 1999; pp. 70-74; vol. 11, No. 1; Wiley-VCH Verlag GmbH.

Zhang et al.; "Rapid pH/temperature-responsive cationic hydrogels with dual stimuli-sensitive grafted side chains"; Polymer; 2009; pp. 2516-2525; vol. 50; Elsevier Ltd.

\* cited by examiner

FIG. 9

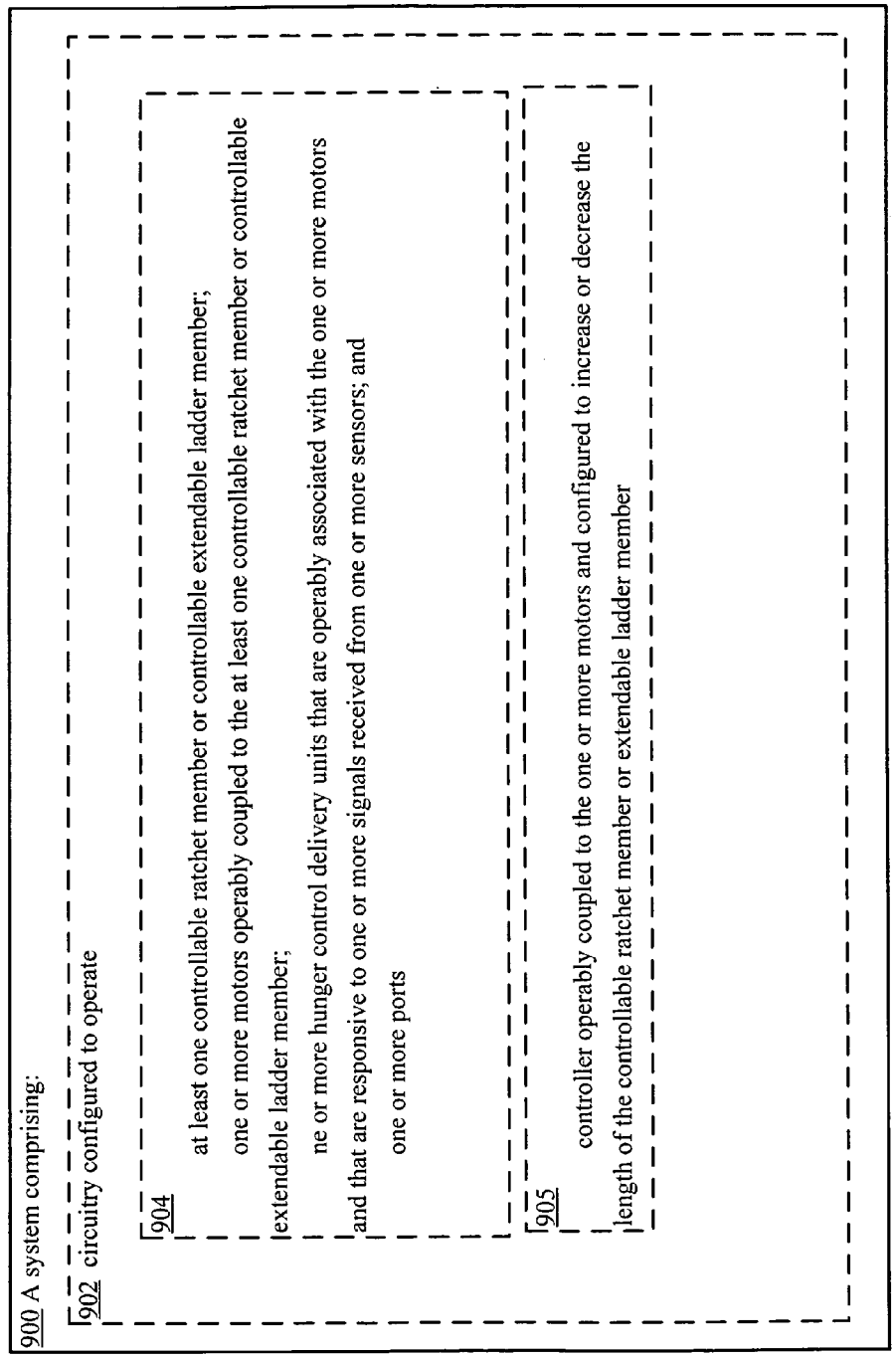

900 A system comprising:

902 circuitry configured to operate 904 at least one controllable ratchet member or controllable extendable ladder member;
one or more motors operably coupled to the at least one controllable ratchet member or controllable extendable ladder member;
one or more hunger control delivery units that are operably associated with the one or more motors and that are responsive to one or more signals received from one or more sensors; and one or more ports 905 controller operably coupled to the one or more motors and configured to increase or decrease the length of the controllable ratchet member or extendable ladder member

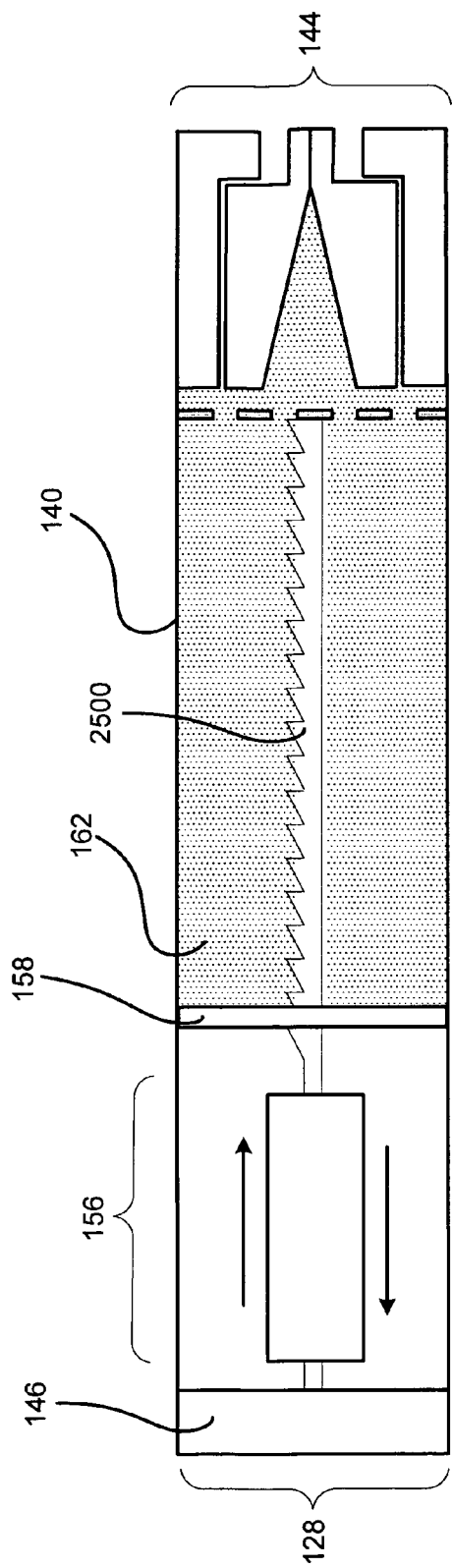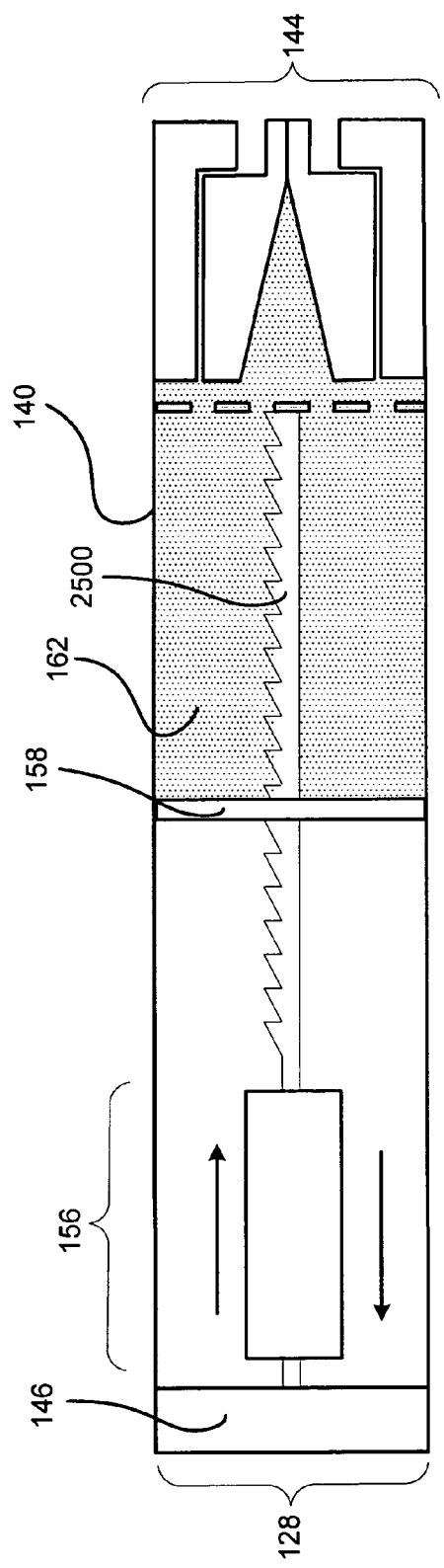

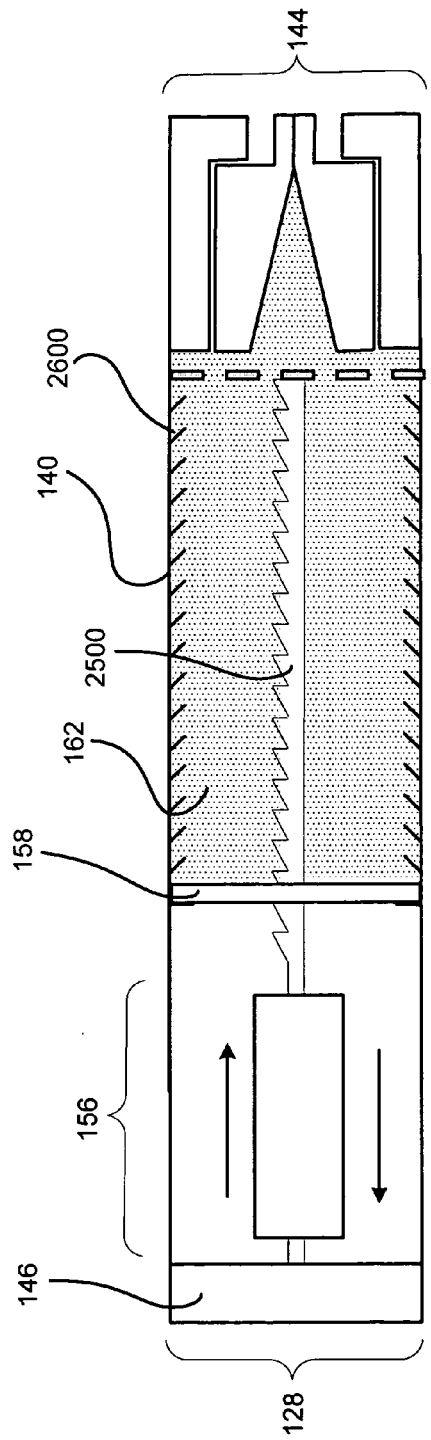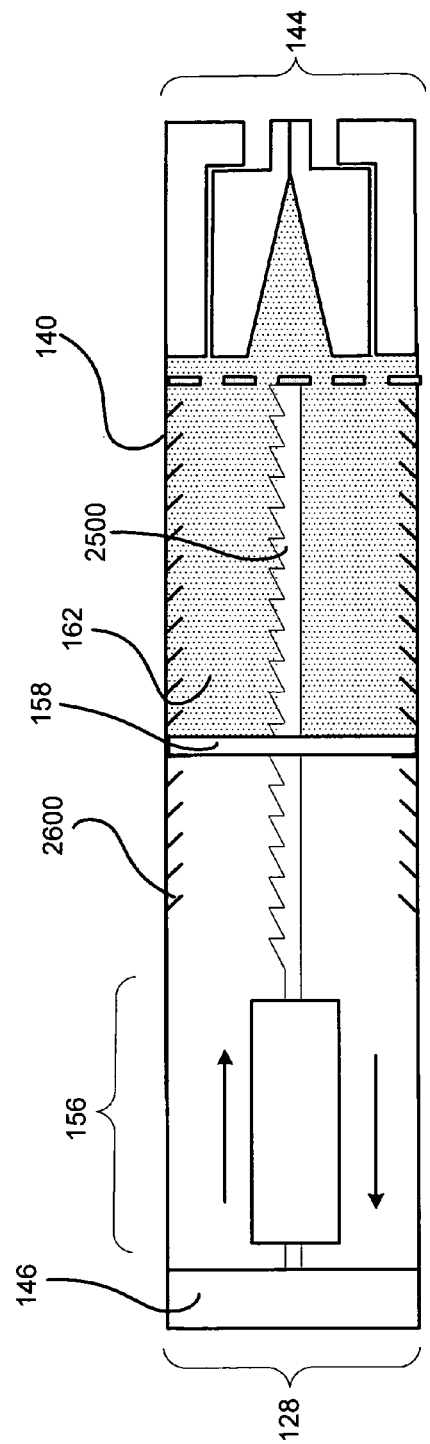

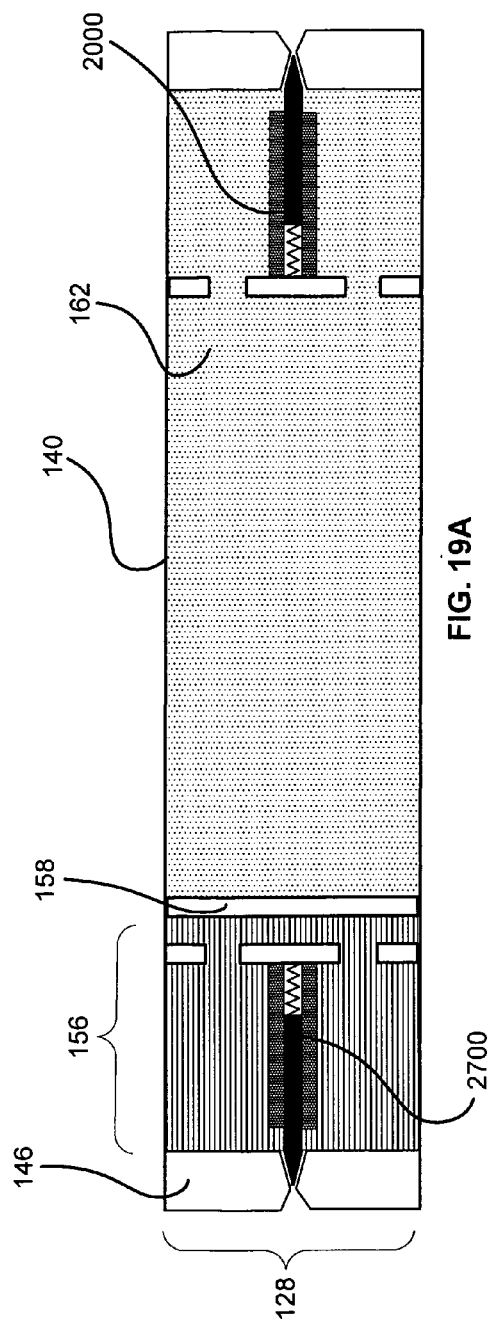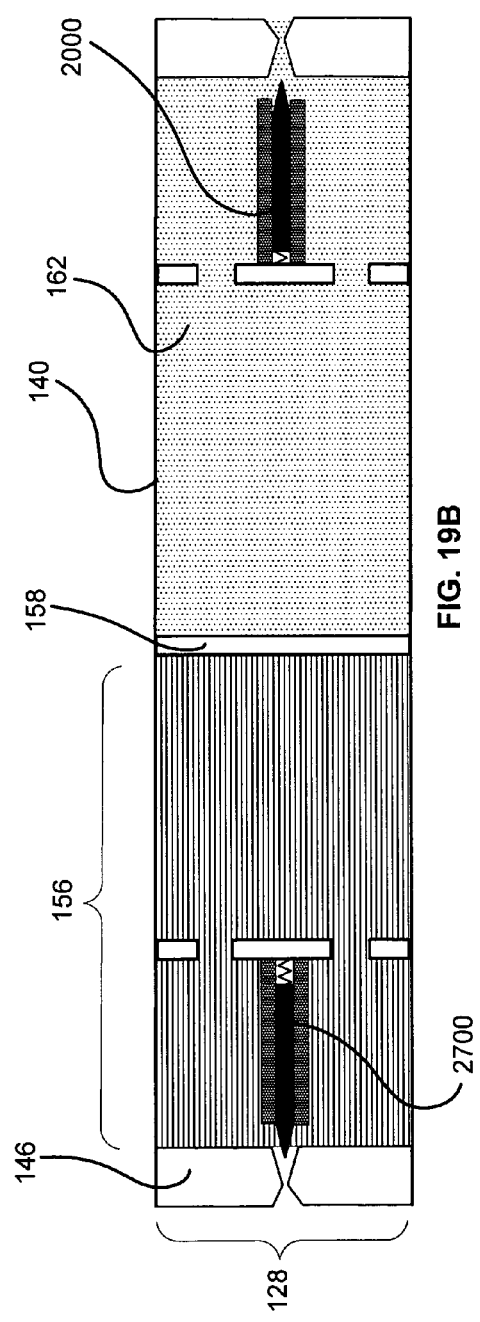

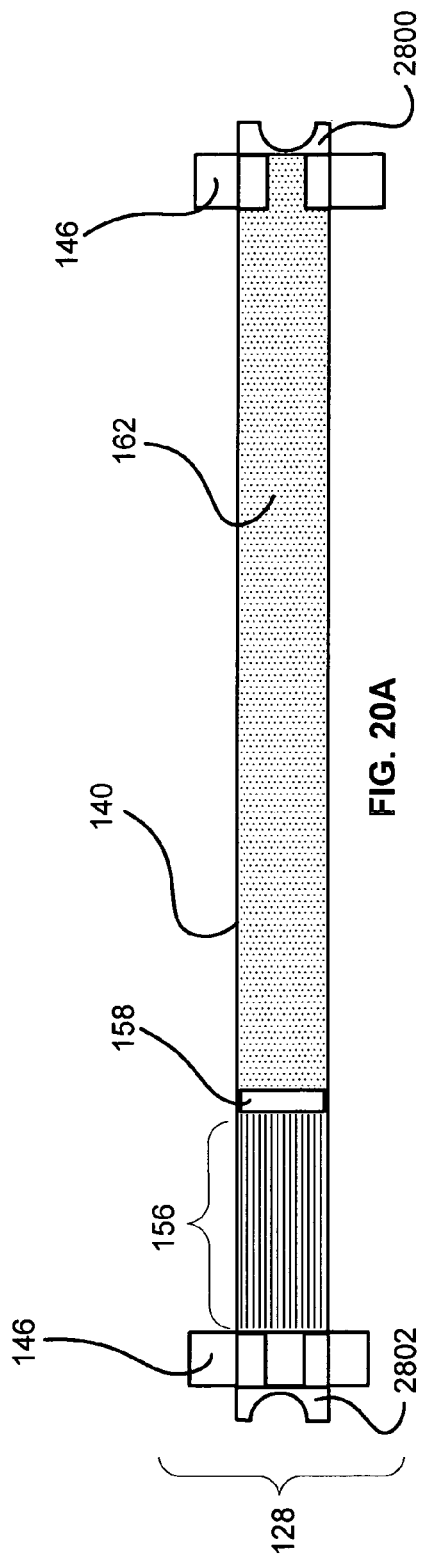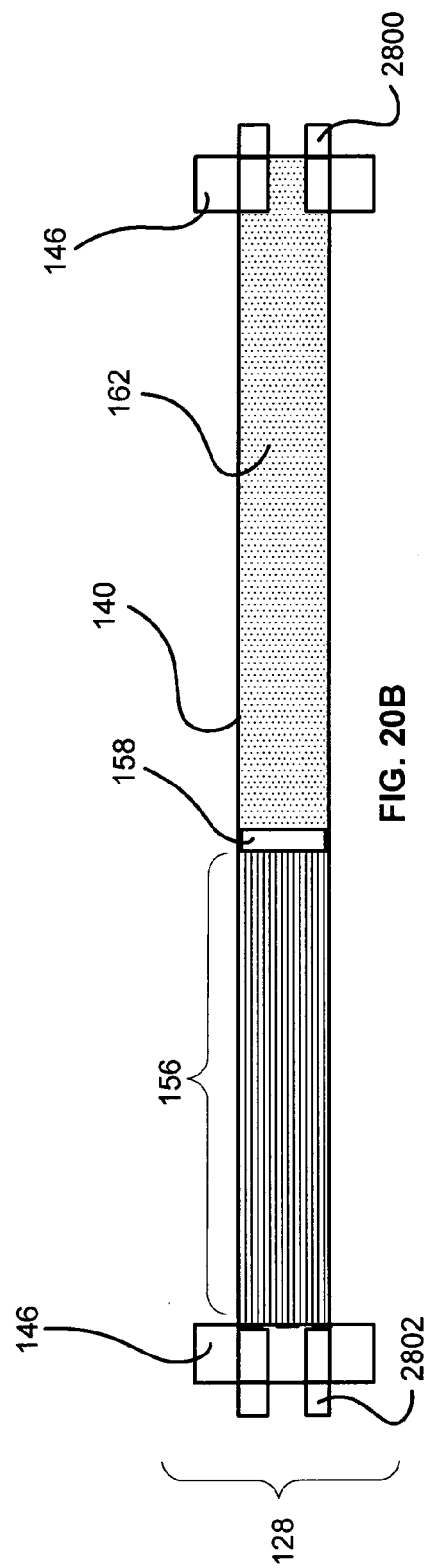

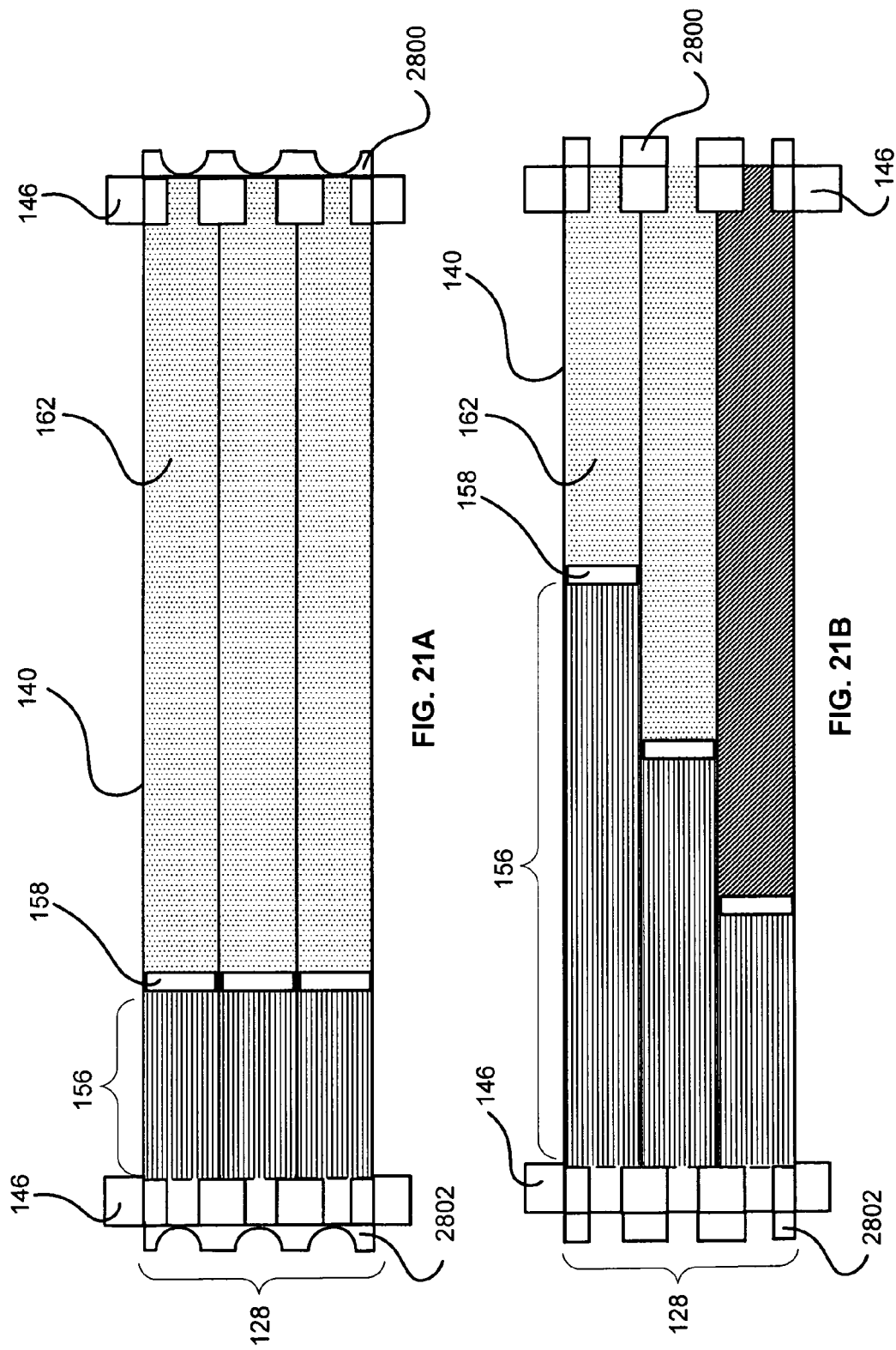

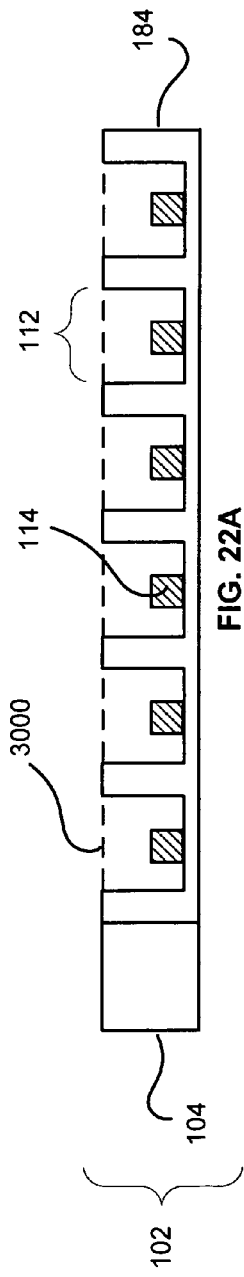
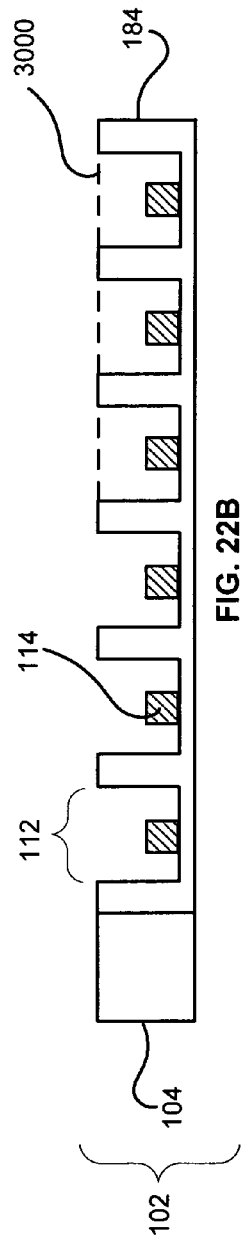
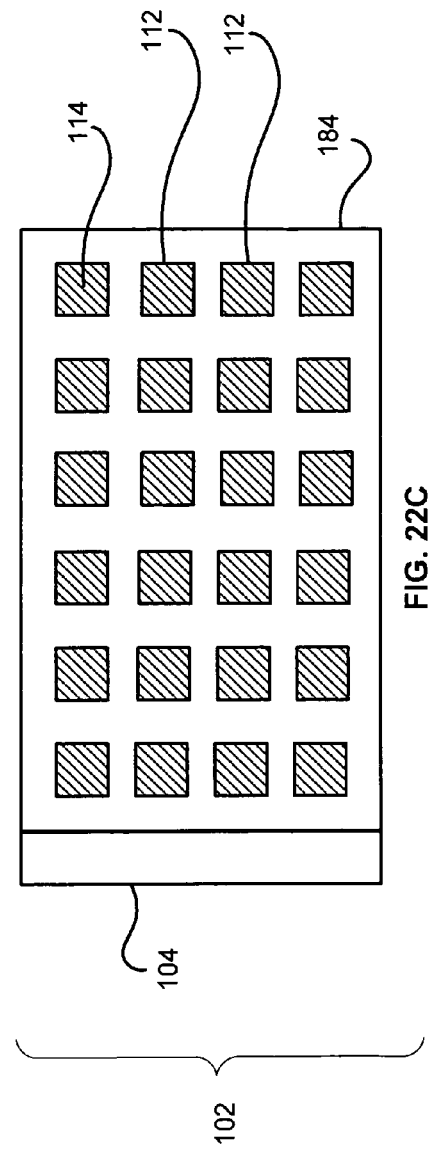

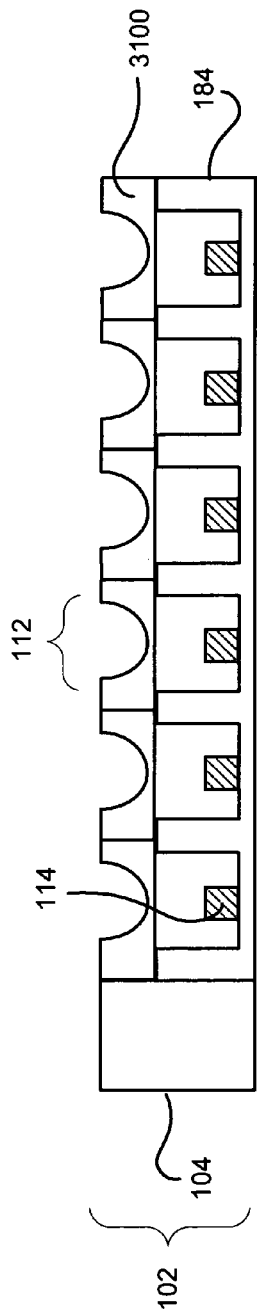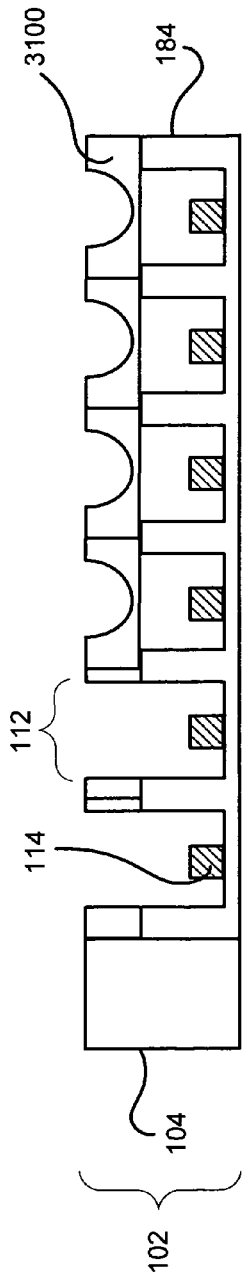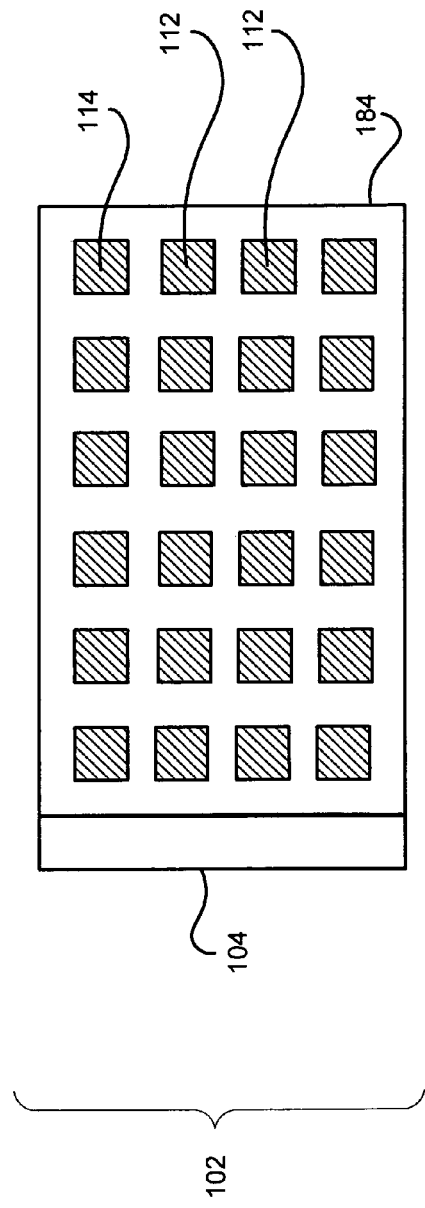

DEVICES, SYSTEMS, AND METHODS TO CONTROL STOMACH VOLUME

CROSS-REFERENCE TO RELATED APPLICATIONS

The present application is related to and claims the benefit of the earliest available effective filing date(s) from the following listed application(s) (the "Related applications") (e.g., claims earliest available priority dates for other than provisional patent applications or claims benefits under 35 USC §119(e) for provisional patent applications, for any and all parent, grandparent, great-grandparent, etc. applications of the Related application(s)). All subject matter of the Related applications and of any and all parent, grandparent, great-grandparent, etc. applications of the Related applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/385,574, entitled DEVICES, SYSTEMS, AND METHODS TO CONTROL STOMACH VOLUME, naming Roderick A. Hyde, Michael A. Smith, Elizabeth A. Sweeney, Lowell L. Wood, Jr., and Richard N. Zare as inventors, filed 24 Feb. 2012, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 13/385,570, entitled DEVICES, SYSTEMS, AND METHODS TO CONTROL STOMACH VOLUME, naming Roderick A. Hyde, Michael A. Smith, Elizabeth A. Sweeney, Lowell L. Wood, Jr., and Richard N. Zare as inventors, filed 24 Feb. 2012, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

SUMMARY

Various embodiments are disclosed herein that relate to methods, devices, systems, and computer program products for controlling stomach volume of a subject.

In an embodiment, the stomach-volume-reducing device includes a reversibly responsive housing encasing or including at least one intelligent responsive matrix. In an embodiment, the device is surgically implanted. In an embodiment, the device is held primarily in the stomach of a subject by its expanded size. In an embodiment, a system includes circuitry for operating the stomach-volume-reducing device.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 9 illustrates a partial view of a particular embodiment of a system with one or more hunger control delivery units as described herein.

FIG. 17A illustrates a partial view of a particular embodiment of a hunger control delivery reservoir as described herein.

FIG. 17B illustrates a partial view of a particular embodiment of a hunger control delivery reservoir as described herein.

FIG. 18A illustrates a partial view of a particular embodiment of a hunger control delivery reservoir as described herein.

FIG. 18B illustrates a partial view of a particular embodiment of a hunger control delivery reservoir as described herein.

FIG. 19A illustrates a partial view of a particular embodiment of a hunger control delivery reservoir as described herein.

FIG. 19B illustrates a partial view of a particular embodiment of a hunger control delivery reservoir as described herein.

FIG. 20A illustrates a partial view of a particular embodiment of a hunger control delivery reservoir as described herein.

FIG. 20B illustrates a partial view of a particular embodiment of a hunger control delivery reservoir as described herein.

FIG. 21A illustrates a partial view of a particular embodiment of a hunger control delivery reservoir as described herein.

FIG. 21B illustrates a partial view of a particular embodiment of a hunger control delivery reservoir as described herein.

FIG. 22A illustrates a partial view of a particular embodiment of a sensor as described herein.

FIG. 22B illustrates a partial view of a particular embodiment of a sensor as described herein.

FIG. 22C illustrates a partial view of a particular embodiment of a sensor as described herein.

FIG. 23A illustrates a partial view of a particular embodiment of a sensor as described herein.

FIG. 23B illustrates a partial view of a particular embodiment of a sensor as described herein.

FIG. 23C illustrates a partial view of a particular embodiment of a sensor as described herein.

DETAILED DESCRIPTION

Figure 1:
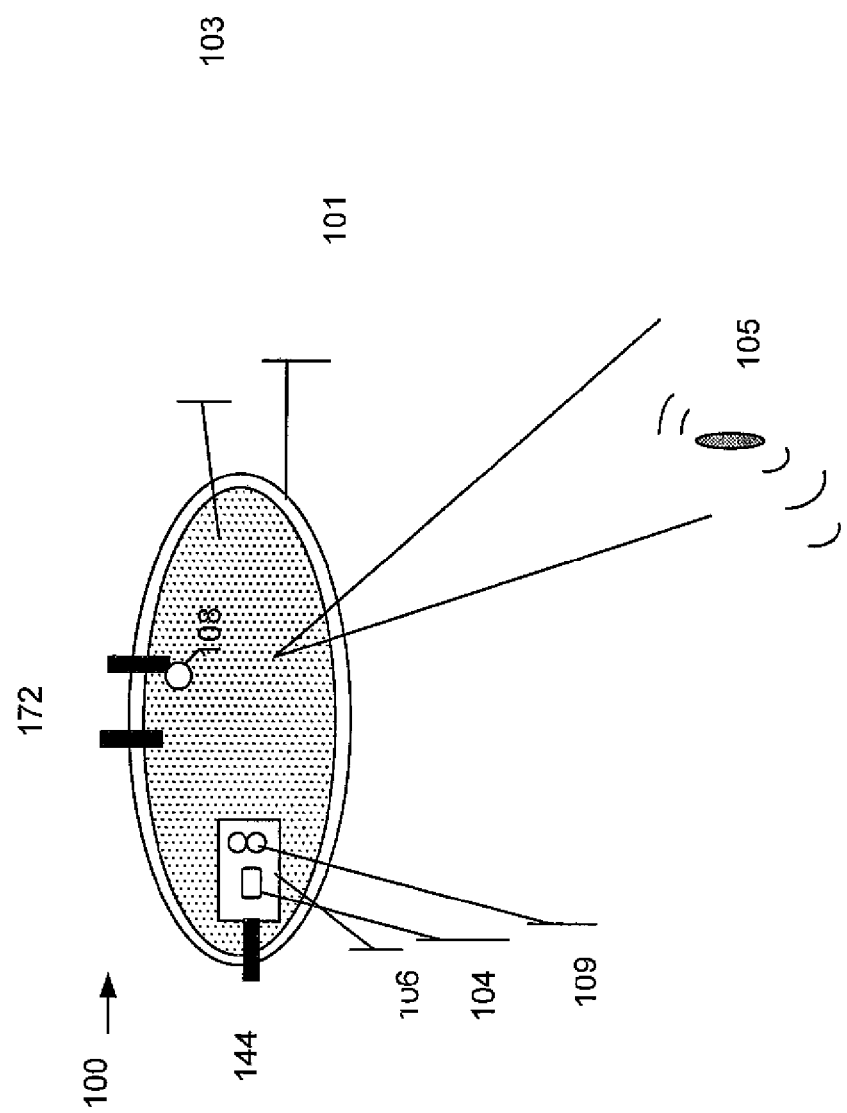
FIG. 1 illustrates a partial view of a particular embodiment of a device and system described herein.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In an embodiment, at least one of the methods, devices, or computer systems disclosed herein are utilized for controlling stomach volume in a subject. In an embodiment, the methods, devices, or computer systems disclosed herein assist in controlling hunger of a subject. In an embodiment, the hunger control is cyclical such that it mimics the subject's natural hunger cycles. In an embodiment, the methods, devices, or computer systems disclosed herein assist in weight loss in a subject by reducing the subject's gastric volume and/or suppressing the subject's appetite.

For example, in an empty state, the stomach is contracted and its mucosa and submucosa are gathered into distinct folds; when distended with food, the folds are flat, altering the size from approximately 50 mL to approximately 1 L. The empty stomach is nonmotile and not producing much acid, although the migrating motor complex is active on a low level. Once a subject becomes aware of food (e.g., by way of smell, thought, sight, etc.), nervous and chemical signals initiate secretion of small amounts of acid and a low level of gastric motility occurs. As food enters the stomach, stretching and irritation of the stomach occurs, and the pH of the stomach is lowered significantly, when secretion of enzymes ensues and contractions begin. The content of food can affect the emptying rate (e.g., presence of fat slows rate of stomach emptying). As pH drops and stomach content shifts, acid production is reduced to basal or negative levels. Thus, in an embodiment, the earlier the device expands to decrease stomach spatial volume in a subject, the better hunger will be suppressed. In an embodiment, the stomach-volume reducing device increases the subject's feeling of satiety or reduces hunger. In an embodiment, chemical appetite suppressants are also utilized to control hunger. (See, for example, on the worldwide web, arbl.cvmbs.colostate.edu/hbooks/pathphys/digestion/stomach/index.html, the contents of which are incorporated herein by reference.)

In an embodiment, a subject includes, but is not limited to, a human or non-human animal (for example, pet, livestock, food animals, wild animals, game animals, etc.).

Stomach Volume Reducing Device

In an embodiment, the stomach volume reducing device includes at least one of an intelligent responsive gel (e.g., swells), gastric attachment, at least one moveable member, or at least one umbrella type mechanism. For example, in an embodiment, the stomach volume reducing device includes a reversibly responsive expandable device, the reversibly responsive expandable device encasing at least one intelligent responsive matrix that is responsive to at least one chemical in the stomach of a subject. In an embodiment, the device includes at least one port. In an embodiment, the device includes at least one controllable micropump or controllable valve operably connected to at least one port. In an embodiment, the device further includes at least one housing. See Figure Descriptions for more details.

In an embodiment, the intelligent responsive matrix includes a crystalline colloidal array. Crystalline colloidal arrays are generally synthesized through a free-radical heterogeneous nucleation emulsion polymerization. See, for example, the worldwide web at: pitt.edu/~asher/homepage/colgrp.html, visited on Jan. 6, 2012, the content of which is incorporated herein by reference. Crystalline colloidal arrays can be prepared in the form of particles that are approximately 100-400 nm in diameter. The reactants for the polymerization include an emulsifier, slightly water-soluble monomers, a less water-soluble crosslinker, a water-soluble initiator, and a buffer in an aqueous polymerization medium. The surface charge and size of the resulting particles can be altered by varying the relative amounts of these reactants. Id. For example, a typical colloidal particle synthesis by emulsion polymerization (for approximately 100 nm particles)

includes approximately 137.5 mL water, 60.0 mL styrene, 2.33 g divinylbenzene, 2.87 g COPS-1, 2.0 g MA-80, 0.17 g NaHCO$_3$, 0.75 g N$_2$H$_8$S$_2$O$_8$, heated at 70° C. for 3 hours. Aqueous suspensions of monodisperse, highly-charged polystyrene particles self-assemble into highly-ordered three-dimensional arrays, known as crystalline colloidal arrays (CCAs). Id. Likewise, a CCA lattice can be stabilized by polymerizing it within a hydrogel to form a polymerized crystalline colloidal array (PCCA) with nonionic polymerizable monomers, cross-linkers and photoinitiators. When molecular recognition groups are incorporated into the hydrogel backbone either during or after polymerization, the resulting intelligent polymerized crystalline colloidal array (IPCCA) will optically report on the concentration of the analyte of interest. As the analyte of interest is bound, there will be a change in the free energy of the system, resulting in a change in the equilibrium volume of the hydrogel and a change in the observed diffraction from the PCCA.

Consequently, many CCAs are formed into sensors, for example, a photonic crystal glucose sensor, protein marker sensors, organophosphate sensors, ammonia sensors, zinc sulfide particle sensor, or others. Id.

In an embodiment, the stomach volume reducing device includes at least one sensor. In an embodiment, the stomach volume reducing device includes at least one transmitter.

FIG. 1 illustrates an embodiment in which a reversibly responsive expandable housing device 100 is a polymer envelope 101 that is encasing glucose-responsive, pH-sensitive hydrogel particles. A portion of the hydrogel particles or a subset of the ingested envelopes may include, within the glucose-responsive, pH-sensitive hydrogel 103, an appetite suppressant 105 that is released upon the gel swelling in response to the glucose and in the presence of low pH. Further, the device includes a microchip 106, piezoelectric pump 104, a port 144 that may be operably associated with a sensor 108 for sensing at least one environmental condition 172 of the subject's stomach, and one or more microvalves 109.

Figure 2:
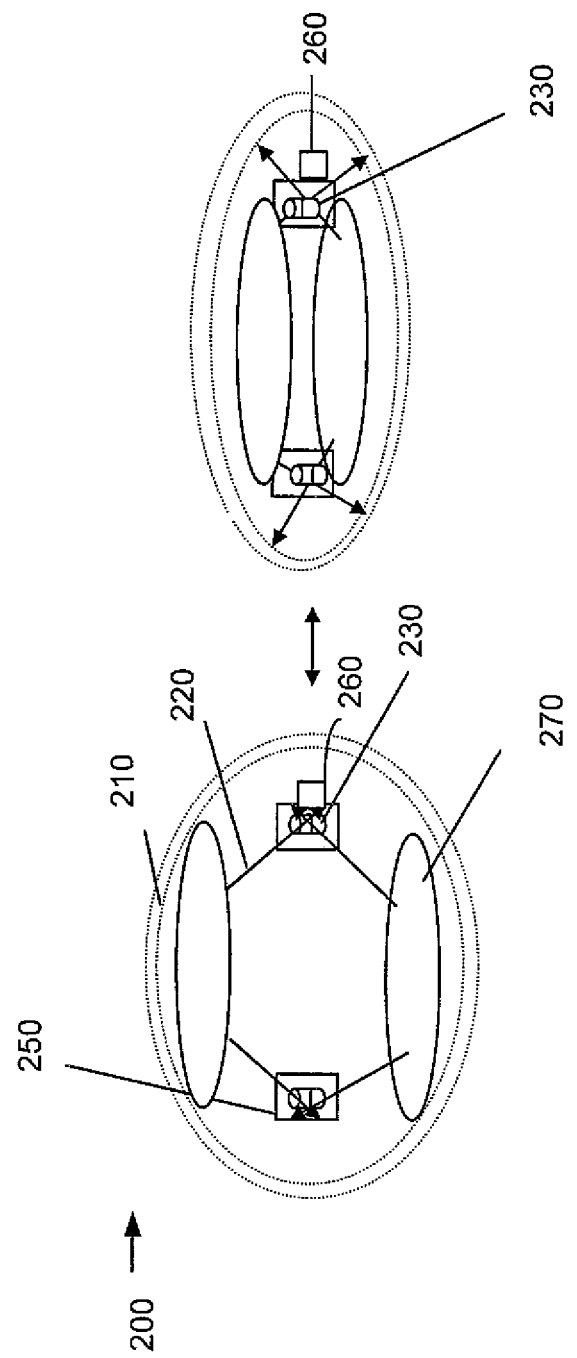
FIG. 2 illustrates a partial view of a particular embodiment of a device and system with a polymer envelope described herein.

FIG. 2 illustrates a reversibly responsive expandable device housing 200 that is, in this embodiment, a non-toxic polymer envelope 210 encasing an actuatable mechanical member 220 (truss rod, as noted other actuatable mechanical members can be used). As illustrated in FIG. 2, the actuatable mechanical members are moveable by at least one piezoelectric motor 230. In addition, the device 200 includes a motor control chip 250 (operably coupled to control circuitry) and an ellipsoid space filler 270. In an embodiment, a sensor 260 is operably coupled to at least one of the actuatable mechanical member, or the motor.

Figure 3B:
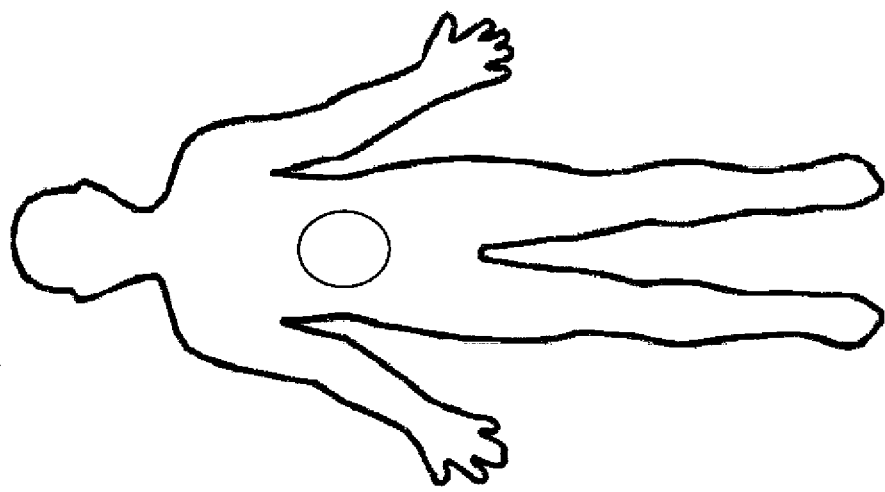
FIG. 3 illustrates a partial view of a particular embodiment of a device located within a subject's body as described herein.
Figure 3A:
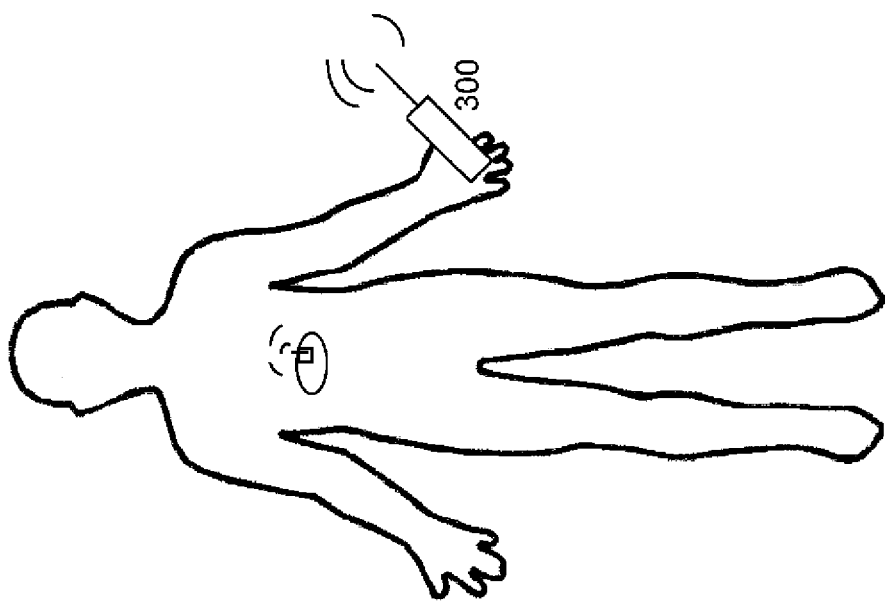

FIG. 3 illustrates a stomach volume reducing device in a collapsed state (FIG. 3A), as well as in an expanded state (FIG. 3B). For example, the chemical is ingested prior to an expected meal, and the chemical-detecting sensor, after detecting the chemical, transmits an electrical signal to the umbrella-like devices to actuate the piezo-electric motors, erect the ellipsoid space fillers, and expand the space filling device to occupy approximately 70% of the stomach volume. In an embodiment, the device includes a remote control 300 that the subject uses to expand or collapse the device. See FIG. 3A.

In an embodiment, the system 100 includes a stomach volume reducing device with one or more hunger control delivery reservoirs 128. See, for example, FIG. 4. In an embodiment, the stomach volume reducing device is configured for implantation within a subject, optionally including one or more hunger control delivery reservoirs 128.

In an embodiment, the stomach volume reducing device includes one or more power sources 116, which may be operably coupled to one or more components of the stomach volume reducing device or the device as a whole. In an embodiment, a hunger control delivery reservoir 128 is operably coupled to one or more batteries 120. In an embodiment, a battery 120 includes a thin-film fuel cell for providing electrical power. In an embodiment, the fuel cell is of a solid oxide type (SOFC), a solid polymer type (SPFC), a proton exchange membrane type (PEMFC), and/or substantially any combination thereof. Methods to fabricate such thin-film fuel cells are known and have been described (e.g., U.S. Pat. No. 7,189,471), incorporated herein by reference. In an embodiment, one or more batteries 120 include one or more storage films that are configured for energy storage and energy conversion. Methods to fabricate such storage films are known and have been described (e.g., U.S. Pat. No. 7,238,628), incorporated herein by reference. In an embodiment, a battery 120 is a biobased battery 120 (e.g., U.S. Pat. No. 6,994,934, incorporated herein by reference). In an embodiment, the battery includes at least one inductive recharger or similar internal charger 121.

In an embodiment, one or more batteries 120 are thin-film batteries 120. Methods to fabricate thin-film batteries 120 are known and have been described (e.g., U.S. Pat. Nos. 7,194, 801; 7,144,655; 6,818,356, incorporated herein by reference). In an embodiment, one or more electromagnetic receivers 118 are used to electromagnetically couple power to energize one or more hunger control delivery reservoirs 128 from an external power source 116. Methods to construct electromagnetic receivers 118 have been described (e.g., U.S. Pat. No. 5,571,152), incorporated herein by reference. Briefly, in an embodiment, one or more electromagnetic receivers 118 may be operably coupled to one or more rectifier chips. The one or more electromagnetic receivers 118 include one or more cores about which are wrapped in an electrical conductor. In an embodiment, cores comprise a material, such as a ferrite material, due to its relatively high magnetic permeability and low magnetic hysteresis. However, other materials can be used for this purpose. In an embodiment, a hunger control delivery reservoir 128 is operably coupled to one or more capacitors 122. In an embodiment, one or more electromagnetic receivers 118 are operably coupled to one or more batteries 120. In an embodiment, one or more electromagnetic receivers 118 are operably coupled to one or more capacitors 122. Accordingly, in an embodiment, one or more hunger control delivery reservoirs 128 are configured such that they are operably coupled to a rechargeable power source 116.

In an embodiment, wireless transmission may serve as a means to power the system, including the external device. See U.S. Patent App. Pub. No. 2005/0143787, which is incorporated herein by reference.

In an embodiment, a hunger control delivery reservoir 128 is operably coupled to one or more hunger control units 146. In an embodiment, the one or more hunger control units 146 serve to regulate the activity of one or more hunger control delivery reservoirs 128. For example, in an embodiment, one or more hunger control units 146 regulate one or more times when one or more hunger control delivery reservoirs 128 administer one or more appetite suppressants 162. In an embodiment, one or more hunger control units 146 regulate one or more time periods when one or more hunger control delivery reservoirs 128 administer one or more appetite suppressants 162 to control hunger. In an embodiment, one or more hunger control units 146 regulate what appetite suppressants 162 are administered by one or more hunger control delivery reservoirs 128. In an embodiment, one or more hunger control units 146 regulate the operation of one or more reservoir motors 156 operably coupled to one or more hunger control delivery reservoirs 128. For example, in an embodiment, one or more control units 146 regulate the duration of operation of one or more reservoir motors 156. In an embodiment, one or more hunger control units 146 regulate the time when one or more reservoir motors 156 are operated. In an embodiment, one or more hunger control units 146 regulate the frequency with which one or more motors 156 are operated. In an embodiment, one or more hunger control units 146 are operably coupled to one or more processors 148. In an embodiment, one or more hunger control delivery reservoirs 128 include a processor 148 configured to process information received from one or more sensors 102. For example, in an embodiment, one or more processors 148 are configured to calculate the concentration of one or more detected pH or electrical signals from the subject. In an embodiment, one or more processors 148 is configured to determine changes in the concentration or source of one or more of detected pH or electrical signals from the subject relative to time. In an embodiment, one or more processors 148 are configured to regulate one or more motors 156 that are operably coupled to the hunger control delivery reservoirs 128. For example, in an embodiment, one or more processors 148 facilitate operation of one or more motors 156 to administer one or more amounts of one or more appetite suppressants 162. In an embodiment, one or more processors 148 facilitate operation of one or more motors 156 to administer one or more appetite suppressants 162 at one or more times. In an embodiment, one or more processors 148 facilitate operation of one or more motors 156 to administer one or more amounts of one or more appetite suppressants 162 at one or more times. In an embodiment, one or more processors 148 include delivery logic 150. For example, in an embodiment, one or more delivery processors 148 include delivery logic 150 that is programmed to facilitate administration of one or more appetite suppressants 162 to an subject. In an embodiment, one or more delivery processors 148 include delivery logic 150 that is programmed to facilitate administration of one or more appetite suppressants 162 to an subject such that the concentration of the one or more appetite suppressants 162 is substantially maintained at a set point. In an embodiment, one or more delivery processors 148 include delivery logic 150 that is programmed to facilitate administration of one or more appetite suppressants 162 to an subject such that the concentration of the one or more appetite suppressants 162 is substantially maintained within a range of concentrations. In an embodiment, one or more delivery processors 148 include delivery logic 150 that is programmed to facilitate administration of one or more appetite suppressants 162 to an subject with regard to characteristics of the subject, particularly hunger or food cravings. For example, in an embodiment, delivery logic 150 accounts for the size of an subject to facilitate administration of one or more appetite suppressants 162 to an subject. In an embodiment, a control unit 146 includes hunger control delivery memory 152. For example, in an embodiment, one or more hunger control delivery reservoirs 128 save information operably coupled to the identity of one or more administered appetite suppressants 162, the concentration of one or more administered appetite suppressants 162, changes in the concentration of one or more appetite suppressants 162, or substantially any combination thereof. Numerous types of memory may be used for hunger control delivery memory 152. Examples of memory include, but are not limited to, flash memory, random access memory, read-only memory, and the like.

In an embodiment, a hunger control delivery reservoir 128 includes one or more transmitters 154. Numerous types of transmitters 154 may be used in association with system 100. Examples of such transmitters 154 include, but are not limited to, transmitters that transmit one or more acoustic signals, optical signals, radio signals, wireless signals, hardwired signals, infrared signals, ultrasonic signals, and the like (e.g., U.S. Pat. Nos. RE39,785; 7,260,768; 7,260,764; 7,260,402; 7,257,327; 7,215,887; 7,218,900; herein incorporated by reference). In an embodiment, one or more transmitters 154 may transmit one or more signals that are encrypted. Numerous types of transmitters are known and have been described (e.g., U.S. Patent Nos. and Published U.S. Patent Applications: U.S. Pat. Nos. 7,236,595; 7,260,155; 7,227,956; US 2006/0280307; herein incorporated by reference).

A hunger control delivery reservoir 128 includes one or more receivers 132. In an embodiment, numerous types of receivers 132 are used in association with system 100. Examples of such receivers 132 include, but are not limited to, receivers that receive one or more acoustic signals, optical signals, radio signals, wireless signals, hardwired signals, infrared signals, ultrasonic signals, and the like. Such receivers 132 are known and have been described (e.g., U.S. Pat. Nos. RE39,785; 7,218,900; 7,254,160; 7,245,894; 7,206,605; herein incorporated by reference).

In an embodiment, the device includes a housing and potentially a reservoir. In an embodiment, one or more device housings 140 are operably coupled with one or more ports 144. In an embodiment, one or more device housings 140 are operably coupled with one or more motors 156. In an embodiment, one or more device housings 140 are operably coupled with one or more moveable members 158. In an embodiment, the one or more moveable members include one or more mechanical actuatable members 159.

In an embodiment, a device housing 140 may be configured as a tube with a port 144 operably coupled to a distal end of the tube. In an embodiment, such a device housing 140 is configured to accept a moveable member 158 that is configured to slide within the interior of the device housing tube from a proximal end of the tube to the distal end of the tube. In an embodiment, the moveable member 158 is operably coupled to one or more motors 156 that are configured to translocate the moveable member 158. In an embodiment, the space within the tube between the moveable member 158 and the port 144 is configured as a reservoir 128 that included one or more appetite suppressants 162. Accordingly, movement of the moveable member 158 from the proximal end to the distal end of the tube will cause the one or more appetite suppressants 162 to be expelled from the port 144. In an embodiment, numerous types of motors 156 can be operably coupled to one or more hunger control delivery reservoirs 128. Examples of such motors 156 include, but are not limited to, stepper motors 156, osmotic motors 156, piezoelectric motors 156, ultrasonic motors 156, acoustic motors 156, and the like. In an embodiment, one or more moveable members 158 can be operably coupled to one or more ratcheted members such that the one or more moveable members 158 can be engaged by the one or more ratcheted members in conjunction with movement facilitated by one or more motors 156.

One or More Sensors

Figure 4:
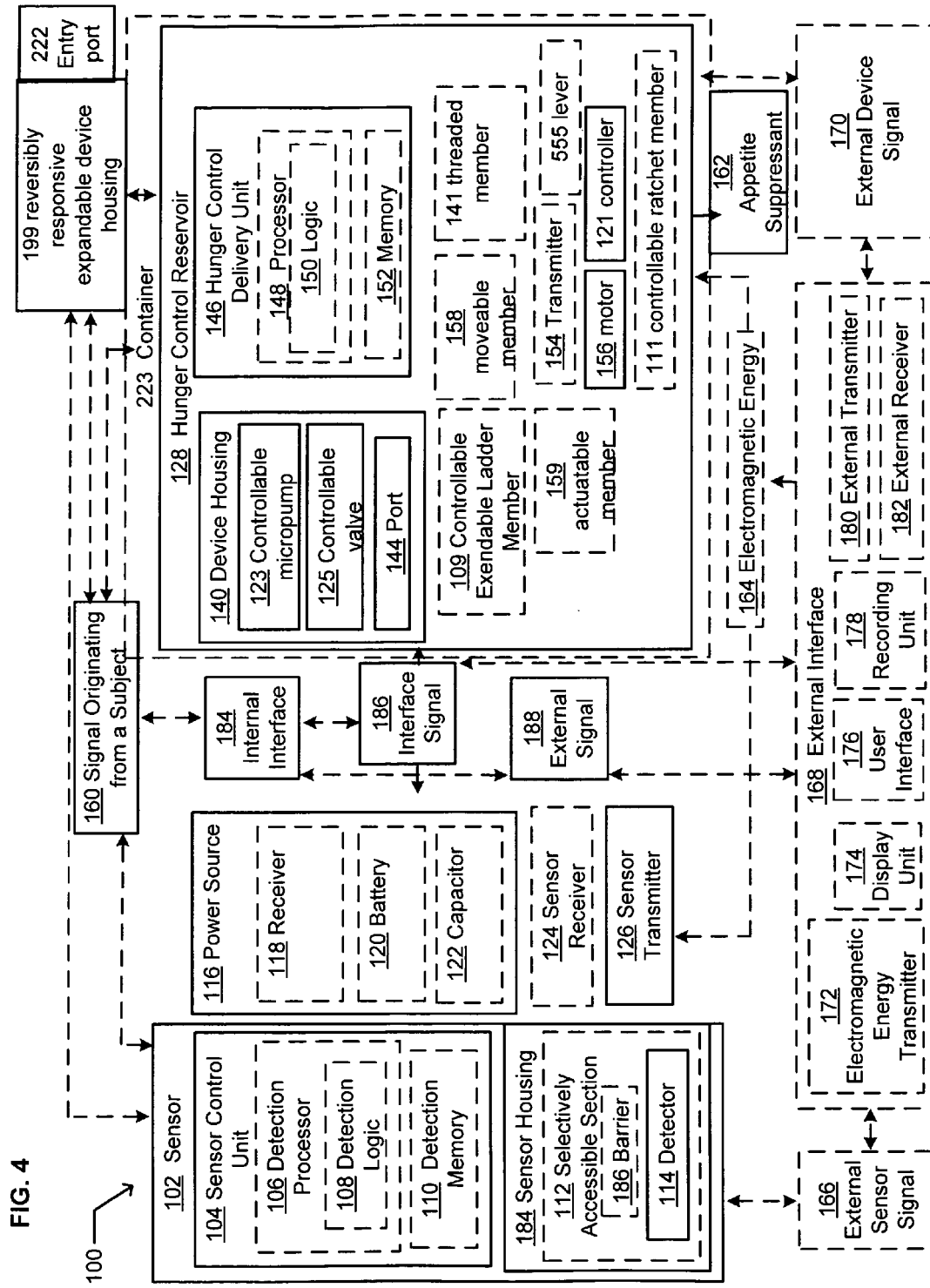
FIG. 4 illustrates a partial view of a particular embodiment of a system described herein.

As illustrated in FIG. 4, in an embodiment, a system 100 includes one or more sensors 102. In an embodiment, one or more sensors 102 may be configured for implantation within an subject (e.g., U.S. Pat. Nos. 7,110,803 and 7,044,911, each of which is incorporated herein by reference). Sensors 102 may be configured for implantation at numerous positions within an subject. For example, in an embodiment, one or more sensors 102 may be configured for implantation into the vasculature of a subject (e.g., U.S. Pat. Nos. 7,181,261; 7,025,734; and 7,236,821, each of which is incorporated herein by reference).

In an embodiment, the one or more sensors 102 include at least one fiber-optic sensor. In an embodiment, the one or more sensors 102 include at least one fiber-optic wave-based biosensor. In an embodiment, the one or more sensors 102 include at least one protein sensor. See, for example, Preejith, et al. Biotech. Lett. 25: 105-110 (2003), which is incorporated herein by reference.

In an embodiment, the one or more sensors 102 include at least one fiber optic sugar sensor. See, for example, Kumar, et al., Pramana J. of Phys. Vol. 67, No. 2, 383-387 (2006), which is incorporated herein by reference.

In an embodiment, the one or more sensors 102 include at least one polymethylmethacrylate fiber sensor.

In an embodiment, the one or more sensors 102 include at least one chemical sensor configured to detect at least one chemical, temperature, pressure, or electrical condition of the subject (e.g., presence of sugar, presence of protein, pH, presence of carbon dioxide or other gases, presence of at least one enzyme, nerve signals originating from the subject, etc.). In an embodiment, at least one chemical or electrical condition sensor is operably coupled to the port. In an embodiment, a port is responsive to the sensed chemical or electrical condition by the at least one chemical or electrical condition sensor. In an embodiment, the chemical sensor is a chemical sensor.

In an embodiment, a sensor 102 is operably coupled to one or more sensor control units 104. In an embodiment, the one or more sensor control units 104 serve to regulate the activity of the one or more sensors 102. For example, in an embodiment, one or more sensor control units 104 regulate one or more times when the one or more sensors 102 detect one or more of pH or electrical signals from the subject. In an embodiment, the one or more sensor control units 104 regulate one or more time periods when one or more sensors 102 detect one or more of pH or electrical signals from the subject. In an embodiment, one or more sensor control units 104 are operably coupled to one or more detection processors 106. In an embodiment, one or more sensors 102 include a detection processor 106 that is configured to process information received from one or more detectors 114. For example, in an embodiment, one or more detection processors 106 are configured to calculate the concentration of one or more of detected pH, chemical chemicals, or electrical (nerve) signals from the subject. In an embodiment, one or more detection processors 106 are configured to determine changes in the concentration of one or more detected pH, chemical chemicals, or nerve signals from the subject relative to time. In an embodiment, one or more detection processors 106 are configured to prepare one or more instructions for one or more hunger control delivery reservoirs 128. For example, in an embodiment, one or more detection processors 106 instruct one or more hunger control delivery reservoirs 128 to administer one or more amounts of one or more appetite suppressants 162.

In an embodiment, the at least one intelligent polymer includes a polymer conjugated to recognize at least one protein (e.g., antibody, enzyme, etc.). Such intelligent polymers are bioconjugated, for example, by random polymer conjugation to lysine amino groups on the protein surface, or by site-specific conjugation of the polymer to specific amino acid sites (e.g., cysteine sulfhydryl groups) that are engineered into the known amino acid sequence of the protein. See, for example, Hoffman, Am. Assoc. for Clin. Chem. on the worldwide web at clinchem.org/content/46/9/1478.full, accessed on Jan. 6, 2012, the content of which is incorporated herein by reference.

In an embodiment, one or more detection processors 106 instruct one or more hunger control delivery reservoirs 128 to administer one or more appetite suppressants 162 at one or more times. In an embodiment, one or more detection processors 106 instruct one or more hunger control delivery reservoirs 128 to administer one or more amounts of one or more hunger control delivery reservoirs 128 at one or more times. In an embodiment, one or more detection processors 106 include detection logic 108. For example, in an embodiment, one or more detection processors 106 include detection logic 108 that is programmed to compensate for background occurring during detection of one or more of pH, chemical presence or levels, or nerve signals from the subject. In an embodiment, detection logic 108 is configured to process information obtained during detection of one or more of pH or electrical signals from a subject to account for the personal characteristics of the subject into which the sensor 102 is implanted. For example, in an embodiment, detection logic 108 is configured to determine the amount of one or more appetite suppressants 162 to be administered to an subject to maintain the concentration of the one or more appetite suppressants 162 at one or more set points within the subject. In an embodiment, detection logic 108 is configured to determine the amount of one or more appetite suppressants 162 to be administered to an subject to maintain the concentration of the one or more appetite suppressants 162 within one or more concentration ranges within the subject. In an embodiment, a sensor control unit 104 may include detection memory 110. For example, in an embodiment, one or more sensors 102 save information operably coupled to the identity of one or more detected pH, chemical, or nerve signals from the subject, the pH level, the source of the nerve signals from the subject, changes in the pH, changes in the type or amount of chemical chemicals present, or nerve signals from the subject, or substantially any combination thereof. Numerous types of memory may be used for detection memory 110. Examples of memory include, but are not limited to, flash memory, random access memory, read-only memory, and the like. In an embodiment, circuitry is configured to operate one or more ports, or the reversibly responsive expandable device housing. In an embodiment, the circuitry configured to operate the reversibly responsive expandable device housing includes circuitry for operating one or more energy storage devices. In an embodiment, circuitry configured to operate the reversibly responsive expandable device housing includes circuitry for operating one or more transmitters. In an embodiment, control circuitry is configured to determine when to engage at least one motor 156 of the device.

In an embodiment, a sensor 102 is configured to wirelessly communicate sensed electrical signals originating from a subject. In an embodiment, a sensor 102 is electrically or optically coupled to the control circuitry to communicate the one or more signals thereto. In an embodiment, the control circuitry is configured to determine when to engage the chemical or electrical condition responsive matrix.

In an embodiment, a sensor 102 includes one or more sensor housings 184. In an embodiment, one or more sensor housings 184 are operably coupled with one or more detectors 114.

In an embodiment, numerous types of detectors 114 may be operably coupled to the one or more sensors 102. In an embodiment, the one or more sensors include at least one detector and reporter. In an embodiment, numerous different types of detectors 114 are operably coupled to one or more sensors 102. Examples of such detectors 114 include, but are not limited to, electrodes, surface plasmon resonance detectors 114, microelectromechanical systems detectors 114, microcantilever detectors 114, nitric oxide detectors 114, osmotic detectors 114, relativity-based detectors 114, chemical detectors 114, pressure detectors 114, electrochemical detectors 114, piezoelectric detectors 114, pH detectors 114, hydrogel detectors 114, enzymatic detectors 114, ball integrated circuit detectors 114, affinity viscosimetric detectors 114, blood pressure detectors 114; metal detectors 114, glucose detectors 114, and the like (e.g., U.S. Pat. Nos. 7,162,289; 6,280,604; 5,603,820; 5,582,170; 6,287,452; 7,291,503; 6,764,446; 7,168,294; 6,823,717; 7,205,701; 6,268,161; 4,703,756; 6,965,791; 6,546,268; 6,210,326; 6,514,689; 6,234,973; 6,442,413; Tu et al., Electroanalysis, 11:70-74 (1999), Malinski et al., Molecular Mechanisms of Metal Toxicity and Carcinogenicity, Environmental Health Perspectives 102, Supplement 3, September 1994, each of which is incorporated herein by reference). In an embodiment, one or more detectors 114 are configured to detect one or more of pH, chemicals, or nerve signals from the subject.

In an embodiment, one or more sensor housings 184 include circuitry that is operably coupled to one or more detectors 114. In an embodiment, one or more sensor housings 184 include circuitry that is configured to facilitate elimination of one or more sacrificial layers. In an embodiment, one or more sensor housings 184 include circuitry that is configured to facilitate reconfiguration of one or more shape memory materials. In an embodiment, one or more sensor housings 184 include circuitry that is configured to be operably coupled to one or more detectors 114. In an embodiment, one or more sensor housings 184 include circuitry that is configured to be operably coupled to one or more sensor control units 104. In an embodiment, one or more sensor housings 184 include circuitry that is configured to be operably coupled to one or more sensor power sources 116. In an embodiment, one or more sensor housings 184 include circuitry that is configured to be operably coupled to one or more sensor receivers 132. In an embodiment, one or more sensor housings 184 include circuitry that is configured to be operably coupled to one or more sensor transmitters 126.

In an embodiment, a sensor 102 includes one or more sensor power sources 116. In an embodiment, a sensor 102 is operably coupled to one or more sensor batteries 120. In an embodiment, a sensor battery 120 includes a thin-film fuel cell for providing electrical power. In an embodiment, the fuel cell is of a solid oxide type (SOFC), a solid polymer type (SPFC), a proton exchange membrane type (PEMFC), and/or substantially any combination thereof. Methods to fabricate such thin-film fuel cells are known and have been described (e.g., U.S. Pat. No. 7,189,471, incorporated herein by reference). In an embodiment, one or more sensor batteries 120 include one or more storage films that are configured for energy storage and energy conversion. Methods to fabricate such storage films are known and have been described (e.g., U.S. Pat. No. 7,238,628, incorporated herein by reference). In an embodiment, a sensor battery 120 is a biobased battery (e.g., U.S. Pat. No. 6,994,934, incorporated herein by reference). In an embodiment, one or more sensor batteries 120 are thin-film batteries. Methods to fabricate thin-film batteries, including thin film microbatteries, are known and have been described (e.g., U.S. Pat. Nos. 5,338,625, 7,194,801; 7,144,655; 6,818,356, incorporated herein by reference). In an embodiment, one or more sensor electromagnetic receivers 118 is used to electromagnetically couple power to energize one or more sensors 102 from an external power source 116. Methods to construct electromagnetic receivers 118 have been described (e.g., U.S. Pat. No. 5,571,152). In an embodiment, the receiver and/or transmitter are not part of the sensor.

Briefly, in an embodiment, one or more electromagnetic receivers 118 are operably coupled to one or more rectifier chips. In an embodiment, the one or more sensor electromagnetic receivers 118 include one or more cores about which are wrapped an electrical conductor. In an embodiment, cores comprise a material, such as a ferrite material, due to its relatively high magnetic permeability and low magnetic hysteresis. However, other materials can be used for this purpose. In an embodiment, a sensor 102 is operably coupled to one or more capacitors 122. In an embodiment, one or more sensor electromagnetic receivers 118 are operably coupled to one or more sensor batteries 120. In an embodiment, one or more sensor electromagnetic receivers 118 are operably coupled to one or more capacitors 122. Accordingly, in an embodiment, one or more sensors 102 are configured such that they are operably coupled to a rechargeable power source 116.

In an embodiment, the system 100 includes one or more sensor transmitters 126. Numerous types of transmitters 126 can be used in association with system 100. Examples of such transmitters 126 include, but are not limited to, transmitters that transmit one or more acoustic signals, optical signals, radio signals, wireless signals, hardwired signals, infrared signals, ultrasonic signals, and the like (e.g., U.S. Pat. Nos. RE39,785; 7,260,768; 7,260,764; 7,260,402; 7,257,327; 7,215,887; 7,218,900), incorporated herein by reference. In an embodiment, one or more sensor transmitters 126 may transmit one or more signals that are encrypted. Numerous types of transmitters are known and have been described (e.g., U.S. Pat. Nos. and Published U.S. Patent Applications: U.S. Pat. Nos. 7,236,595; 7,260,155; 7,227,956; U.S. 2006/0280307), in corporate herein by reference.

In an embodiment, the system 100 includes one or more sensor receivers 132. Numerous types of sensor receivers 132 may be used in association with system 100. Examples of such sensor receivers 132 include, but are not limited to, receivers that receive one or more acoustic signals, optical signals, radio signals, wireless signals, hardwired signals, infrared signals, ultrasonic signals, and the like. Such receivers 132 are known and have been described (e.g., U.S. Pat. Nos. RE39,785; 7,218,900; 7,254,160; 7,245,894; 7,206,605), incorporated herein by reference.

Signal

In an embodiment, numerous types of signals can be used in association with a system 100. In an embodiment, a signal may be an internal signal 160. In an embodiment, a signal may be an external sensor signal 166. In an embodiment, a signal can be an external device signal 170. In an embodiment, a signal can be an interface signal 186. In an embodiment, a signal can be an external signal 188. Examples of such signals include, but are not limited to, analog signals, digital signals, acoustic signals, optical signals, radio signals, wireless signals, hardwired signals, infrared signals, ultrasonic signals, and the like. In an embodiment, one or more signals may not be encrypted. In an embodiment, one or more signals may be encrypted. In an embodiment, one or more signals may be sent through use of a secure mode of transmission. In an embodiment, one or more signals may be coded for receipt by a specific subject. In an embodiment, such code may include anonymous code that is specific for an subject. Accordingly, information included within one or more signals may be protected against being accessed by others who are not the intended recipient.

In an embodiment, one or more signals include information operably coupled to the operation of one or more hunger control delivery reservoirs 128. In an embodiment, the one or more hunger control delivery reservoirs 128 are refillable. For example, in an embodiment, the reservoir includes a magnet that allows the reservoir to be manipulated from either internal or external to the subject's stomach. The magnet allows for location and manipulation of the reservoir such that it can be refilled from an external catheter or other refillable mechanism. In an embodiment, one or more signals include information operably coupled to the operation of one or more motors 156 operably coupled to a hunger control delivery reservoir 128. For example, in an embodiment, one or more signals include information operably coupled to the operation of one or more motors 156 operably coupled to a hunger control delivery reservoir 128. Examples of such information include, but are not limited to, the number of cycles that a motor 156 is to operate, the number of steps that a motor 156 is to operate, the duration of time for which a motor 156 is to operate, the rate at which a motor 156 is to operate, one or more times when a motor 156 is to operate, and the like. Such information may be operably coupled to numerous types of motors 156. In an embodiment, one or more signals include information that is operably coupled to the operation of one or more ports that are operably coupled to one or more hunger control delivery reservoirs 128. In an embodiment, one or more signals include instructions for a hunger control delivery reservoir 128 to open one or more ports. In an embodiment, one or more signals include instructions for the device to close one or more ports. Examples of such ports include, but are not limited to, electromagnetic ports, shape memory ports, and the like (e.g., Low et al., Sensors and Actuators B: Chemical, 76:149-160 (2000), Pan et al., Proceedings of the 26th Annual International Conference of the IEEE EMBS, San Francisco, Calif., USA, Sep. 1-5 (2004), U.S. Pat. No. 6,454,759, each of which is incorporated herein by reference). In an embodiment, such ports may be operably coupled to one or more osmotic motors 156. In an embodiment, one or more ports may be opened and/or closed to regulate entry of fluid into one or more chambers of an osmotic motor 156 to control the operation of the motor 156. For example, in an embodiment, one or more ports may be opened to allow fluid to enter into one or more chambers of an osmotic motor 156 to facilitate movement of one or more moveable members 158 that facilitate extrusion of one or more appetite suppressants 162 from the hunger control delivery reservoir 128. In an embodiment, the one or more ports may be maintained in an open position to provide for entry of fluid into one or more chambers of the osmotic motor 156 or the ports may be closed to disallow entry of fluid into one or more chambers of the osmotic motor 156. Accordingly, in an embodiment, one or more signals may be received by one or more hunger control delivery reservoirs 128 that provide the one or more hunger control delivery reservoirs 128 with instructions operably coupled to the delivery of one or more appetite suppressants 162.

Appetite Suppressants

In an embodiment, numerous types of appetite suppressants 162 are used within system 100 to control hunger in a subject. Examples of such appetite suppressants include but are not limited to leptin, exendin-4, peptide YY, caffeine, cholecystokinin, pancreatic polypeptide, glucagon-like peptide-1, glucagon-like peptide-2, oxyntomodulin, motilin, PHI/PHV, PPY3-36, somatostatin, proopiomelanocortin, chitosan, or a similar agent.

In an embodiment, the at least one appetite suppressant is included with chemical or electrical condition responsive matrix (including, but not limited to responsive particles). In an embodiment, the chemical responsive matrix includes at least one hydrogel. In an embodiment, the chemical responsive matrix is formulated for gradual release of the appetite suppressant from the matrix. In an embodiment, the chemical responsive matrix is formulated to release the appetite suppressant by way of diffusion or dissolution of the matrix. In an embodiment, the chemical responsive matrix is coated in at least one appetite suppressant. In an embodiment, the chemical responsive matrix includes particles formulated to expand in the presence of a particular pH range.

Figure 5:
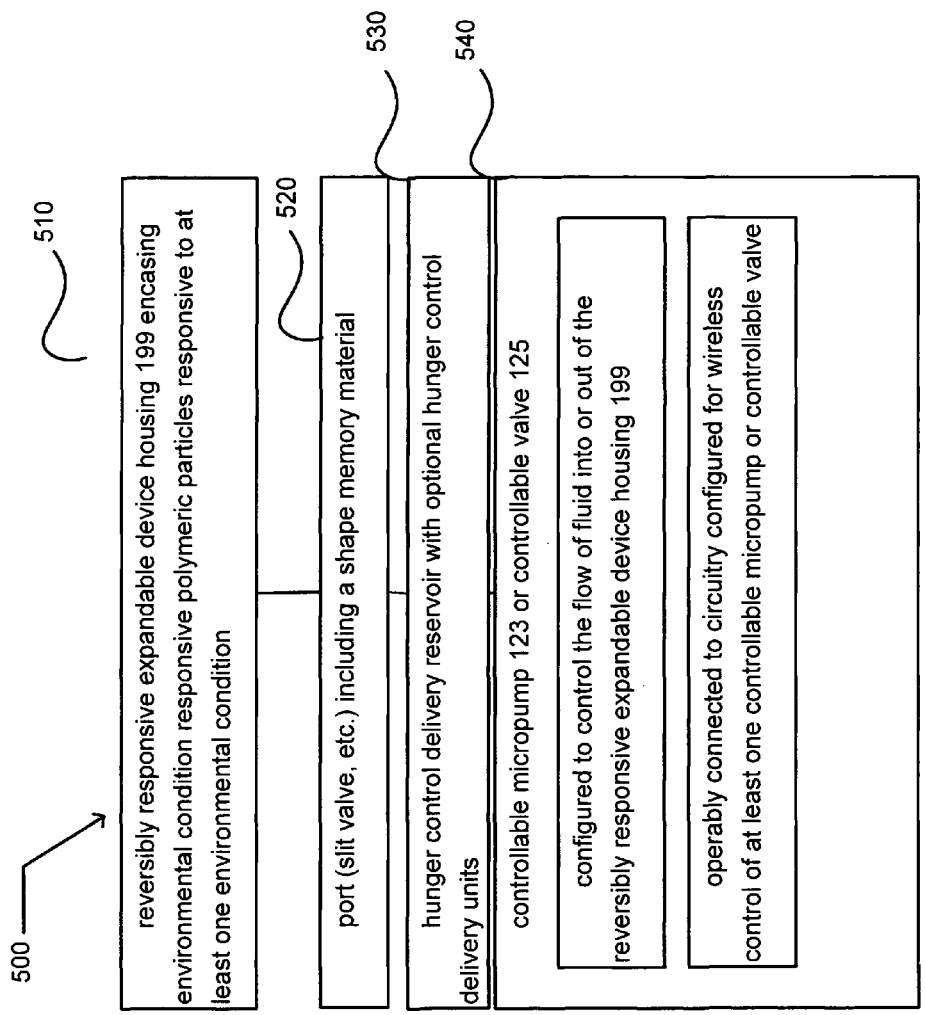
FIG. 5 illustrates a partial view of a particular embodiment of a system and method described herein.

FIG. 5 illustrates embodiment 500 of a stomach-volume-reducing device including reversibly responsive expandable device housing 199 encasing environmental condition responsive polymeric particles responsive to at least one environmental condition, and which optionally includes at least one hunger control delivery reservoir 128 within system 100. In FIG. 5, discussion and explanation may be provided with respect to the above-described example of FIG. 4 and/or with respect to other examples and contexts. However, it should be understood that the modules may execute operations in a number of other environments and contexts, and/or modified versions of FIG. 4. Also, although the various modules are presented in the sequence(s) illustrated, it should be understood that the various modules may be configured in numerous orientations.

The embodiment 500 may include module 510 that includes a reversibly responsive expandable device housing 199 encasing a responsive polymeric matrix that is responsive to at least one chemical, including pH, chemical, or nerve signal.

The embodiment 500 may include module 520 that includes a port that is configured in numerous possible ways. For example, in an embodiment, at least one port 144 may be configured as a slit valve (e.g., U.S. Pat. No. 6,217,906, incorporated herein by reference). In an embodiment, one or more slit valves may be electrically controllable. For example, in an embodiment, a slit valve may include a locking member that is under electrical control. In an embodiment, such a locking member may be an electromagnetically controlled bar that is configured to lock a slit valve in a closed position. In an embodiment, one or more ports 144 may include a shape memory material. In an embodiment, one or more ports 144 may include a shape memory material that is electrically controllable. For example, in an embodiment, one or more ports 144 may include one or more shape memory materials that open when heated. In an embodiment, one or more ports 144 may include one or more shape memory materials that open when heated with an electrical coil. Accordingly, in an embodiment, such ports 144 may be opened and/or closed through application of electric current to a heating coil operably coupled to the port 144. In an embodiment, one or more ports 144 may include one or more electromagnetic closures. Electromagnetic closures may be configured in numerous possible ways. In an embodiment, an electromagnetic closure may include a plug that is configured to eliminate flow through a port 144. The plug may be operably coupled to a spring such that the plug is forced into a port 144 by the spring. The plug may be removed from the port 144 through application of a magnetic field to the plug through use of an electromagnet. Accordingly, flow through the port 144 may be controlled through application of a magnetic field to the plug. In an embodiment, an electromagnetic closure for a port 144 may include a hatchway mechanism wherein a door that covers the port 144 may be opened through application of a magnetic field to the door. In embodiment, ports 144 may be configured to facilitate exit of one or more appetite suppressants 162 from a hunger control delivery reservoir 128.

The embodiment 500 may include module 530 that includes at least one hunger control delivery reservoir with optional hunger control delivery units.

The embodiment 500 may include module 540 that includes at least one controllable micropump 123 or controllable valve 125 operably connected to the at least one port 144. In an embodiment, the at least one controllable micropump 123 or controllable valve 125 is operably connected to at least one transmitter 154 or receiver 118. In an embodiment, the at least one controllable micropump 123 or controllable valve 125 is operably connected to circuitry configured for control of the at least one controllable micropump 123 or controllable valve 125. In an embodiment, the at least one controllable micropump 123 or controllable valve 125 is operably connected to circuitry configured for wireless control of the at least one controllable micropump 123 or controllable valve 125.

Figure 6:
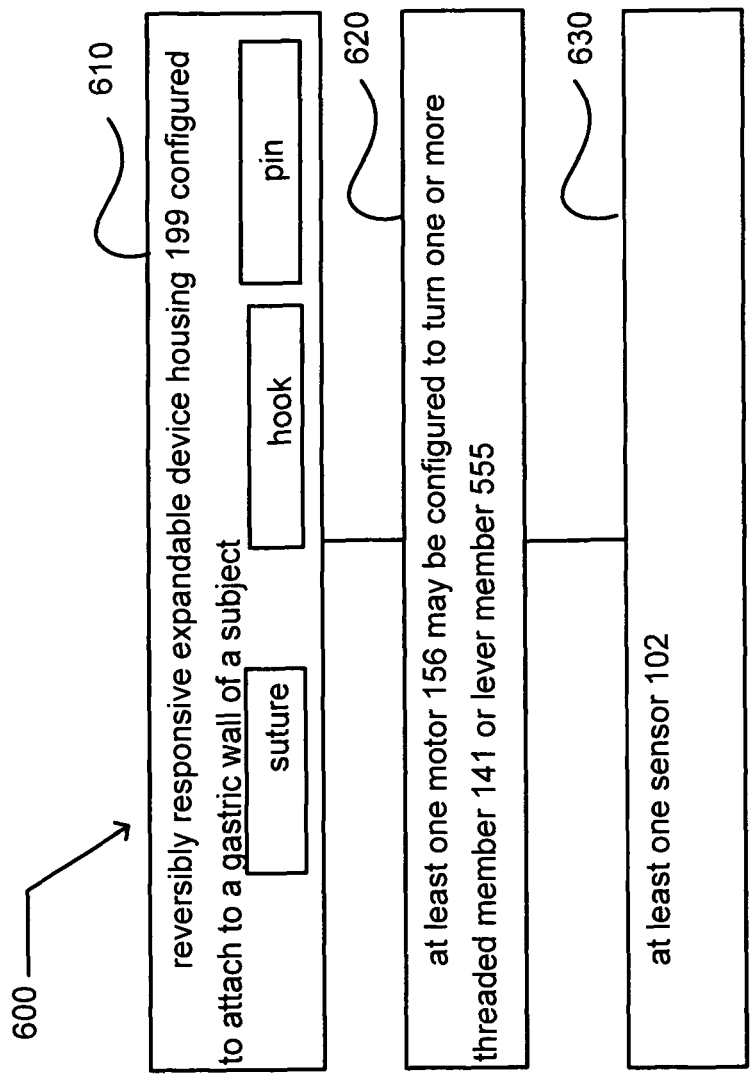
FIG. 6 illustrates a partial view of a particular embodiment of a system and method described herein.

FIG. 6 illustrates an embodiment 600 that may include module 610 that includes at least one reversibly responsive expandable device housing 199 configured to attach to a gastric wall of a subject (e.g., by way of a suture, hook, or pin). In an embodiment, module 620 may include at least one motor 156. In an embodiment, one or more motors 156 may be operably coupled to one or more actuatable mechanical members 159 through a threaded member 141 or lever member 555. In an embodiment, one or more motors 156 may be configured to turn one or more threaded member 141 or lever member 555 (See FIG. 5), to cause movement of one or more actuatable mechanical members 159. In an embodiment, one or more motors 156 may be operably coupled to one or more actuatable mechanical members 159 through a ratchet member 111. In an embodiment, one or more motors 156 may be configured to advance the one or more ratchet members 111 to cause movement of one or more actuatable mechanical members 159. In an embodiment, the at least one actuatable mechanical member 159 includes at least one linear displacement actuator within the member. In an embodiment, the at least one actuatable mechanical member 159 includes at least one shape memory alloy. See, for example, U.S. Pat. Nos. 7,931,693 and 8,021,384, each of which is incorporated herein by reference. In an embodiment, module 630, the device includes at least one sensor.

Accordingly, as shown in FIG. 5, in an embodiment one or more motors 156 may be calibrated to advance one or more actuatable mechanical members 159 a certain distance to increase the volume of the stomach-volume reducing device. In an embodiment, one or more motors 156 facilitate release of one or more appetite suppressants 162 from an optional hunger control delivery reservoir 128. A hunger control delivery reservoir 128 may be operably coupled to numerous types of motors 156. Examples of such motors 156 include, but are not limited to, rotary motors 156, linear motors 156, osmotic motors 156, electric motors 156, piezoelectric motors 156, ultrasonic motors 156, and the like. Accordingly, in an embodiment, one or more motors 156 may be operably coupled to circuitry that is configured to operate the one or more motors 156. For example, in an embodiment, circuitry may be configured to operate one or more motors 156 for a certain period of time to facilitate administration of one or more appetite suppressants 162 to a subject with whom a hunger control delivery reservoir 128 is associated. In an embodiment, circuitry can be configured to calibrate one or more motors 156 to facilitate administration of a select amount of one or more appetite suppressants 162 to a subject with whom a hunger control delivery reservoir 128 is associated. In an embodiment, the at least one hunger control delivery reservoir includes at least one fluid for activating the chemical responsive matrix, and at least one opening in fluid communication with the chemical responsive matrix. In an embodiment, at least one fluid for activating the chemical responsive matrix includes acidified water.

In an embodiment, as shown in FIG. 5, at least one controller 121 is configured to activate expansion of the stomach-volume reducing device to a programmed level of expansion. In an embodiment, at least one sensor 102 is operably coupled to at least one motor 156 and is configured to wirelessly communicate sensed electrical signals originating from the subject. In an embodiment, the at least one sensor 102 is electrically or optically coupled to the control circuitry to communicate the one or more signals thereto. In an embodiment, the control circuitry is configured to determine when to engage the at least one motor 156. In an embodiment, at least one controller 121 is configured to activate expansion of the stomach volume reducing device responsive to the control circuitry determining that the at least one reversibly responsive expandable stomach volume reducing device is to be deployed. In an embodiment, the at least one Controller 121 is configured to activate expansion of the stomach volume reducing device to a programmed level of expansion. In an embodiment, the control circuitry is operably coupled to the stomach volume reducing device configured to operate the at least one motor 156 responsive to receiving one or more signals from the at least one sensor 102 and is configured to actuate the at least one actuatable mechanical member 159 operably coupled to the at least one motor 156. In an embodiment, the system 100 includes a first data transmitter 154 coupled to the control circuitry, the first data transmitter 154 configured to transmit information at least related to data encoded in the one or more sensed electrical signals of the subject. In an embodiment, the first data transmitter 154 is configured to wirelessly transmit the information. In an embodiment, the control circuitry is programmable. In an embodiment, the device is programmable for expansion of about 5%, about 10%, about 15%, about 20%, about 30%, about 40%; about 50%, about 60%, about 70%, about 80%, about 90%, about 100%, or any value less than or therebetween. In an embodiment, the device is programmable for expansion at different rates at different time points. In an embodiment, the device is programmable for expansion at different levels at different time points. In an embodiment, the control circuitry is configured to direct the data transmitter 154 to transmit the information to a third part or a second device. In an embodiment, the second device includes a second stomach-volume-reducing device. In an embodiment, the system includes a memory module configured to store data encoded in the one or more sensed electrical signals of the subject.

In an embodiment, the control circuitry is operably coupled to the stomach-volume reducing device configured to operate the at least one motor 156 responsive to receiving one or more signals from the at least one sensor 102 and is configured to actuate the at least one actuatable mechanical member 159 operably coupled to the at least one motor 156.

In an embodiment, at least one wireless remote controller 121 may be operably coupled to the at least one motor 156. In an embodiment, at least one reversibly responsive reversibly responsive expandable device housing 199 is made from a first polymer, the reversibly responsive reversibly responsive expandable device housing 199 encasing chemical responsive particles made from a second polymer, the reversibly responsive reversibly responsive expandable device housing 199 including at least one port 144; and at least one controllable micropump 123 or controllable valve 125 operably connected to the at least one port 144.

Figure 7:
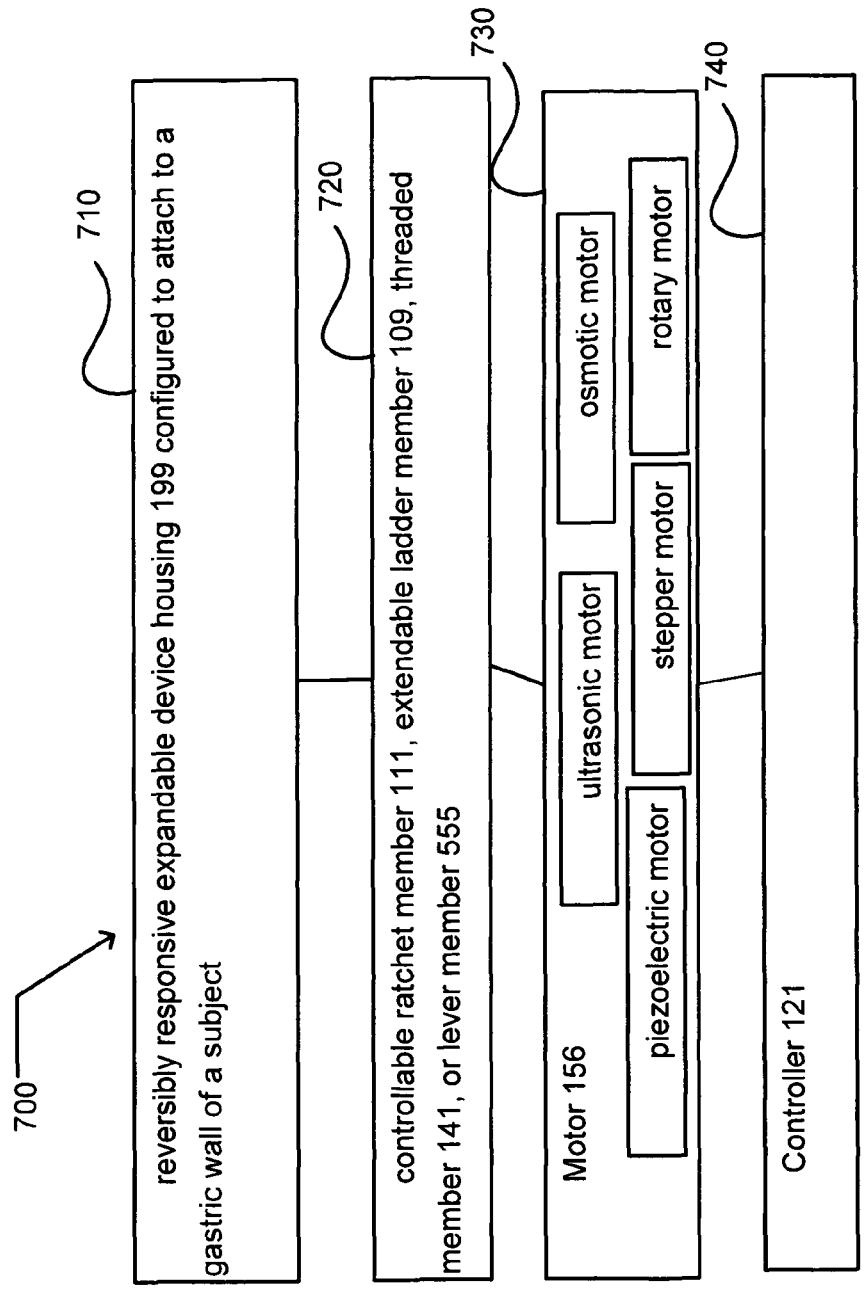
FIG. 7 illustrates a partial view of a particular embodiment of a system and method with various motors as described herein.

FIG. 7 illustrates an embodiment 700 that may include module 710 that includes at least one reversibly responsive expandable device housing 199 configured to attach to a gastric wall of a subject. In an embodiment, module 720 may include at least one controllable ratchet member 111 or extendable ladder member 109, threaded member 141, or lever member 555. In an embodiment, module 730 may include at least one motor 156 (e.g., ultrasonic motor, osmotic motor, piezoelectric motor, stepper motor, rotary motor, etc.), operably coupled to the at least one controllable ratchet member 111 or controllable extendable ladder member 109. In an embodiment, module 740 may include at least one controller operably coupled to the at least one motor 156 and configured to increase or decrease the length of the controllable ratchet 111 or controllable extendable ladder member 109. A controller 121 may be operably coupled to the at least one motor 156.

Figure 8:
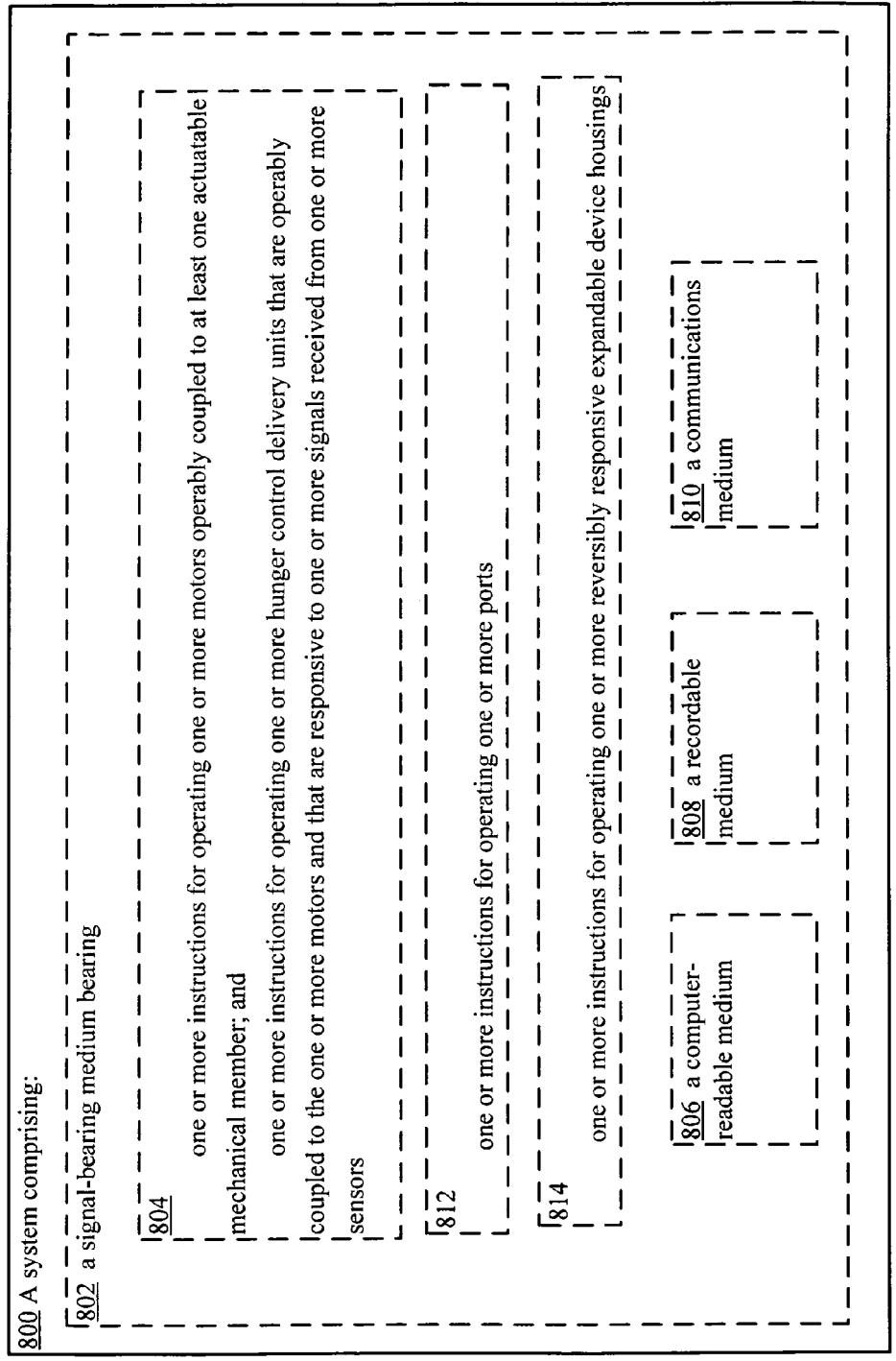
FIG. 8 illustrates a partial view of a particular embodiment of a system as described herein.

FIG. 8 illustrates a partial view of a system 800 that includes a computer program 802 including a signal bearing medium bearing instructions for executing a computer process on a computing device. An embodiment of system 800 is provided using a signal-bearing medium 802 bearing one or more instructions 804 for operating one or more motors 156 and one or more instructions for operating one or more hunger control units 146 that are operably coupled to the one or more motors 156 and that are responsive to one or more signals received from one or more implanted sensors 102. The one or more instructions may be, for example, computer executable and/or logic-implemented instructions. In an embodiment, the signal-bearing medium 802 may include a computer-readable medium 806. In an embodiment, the signal-bearing medium 802 may include a recordable medium 808. In an embodiment, the signal-bearing medium 802 may include a communications medium 810. In an embodiment, the module 812 may include one or more instructions for operating one or more ports 144. In an embodiment, a module 814 may include one or more instructions for operating one or more reversibly responsive reversibly expandable device housings.

FIG. 9 illustrates a partial view of a system 900 that includes circuitry 902 configured to operate at least one controllable ratchet member 111 or controllable extendable ladder member 109. In an embodiment, the system 900 includes circuitry 904 configured to operate one or more motors 156 operably coupled to the at least one controllable ratchet member 111 or controllable extendable ladder member 109. In an embodiment, the system 900 includes at least one controller 905 operably coupled to the one or more motors 156 and configured to increase or decrease the length of the controllable ratchet member 111 or extendable ladder member 109.

Figure 10:
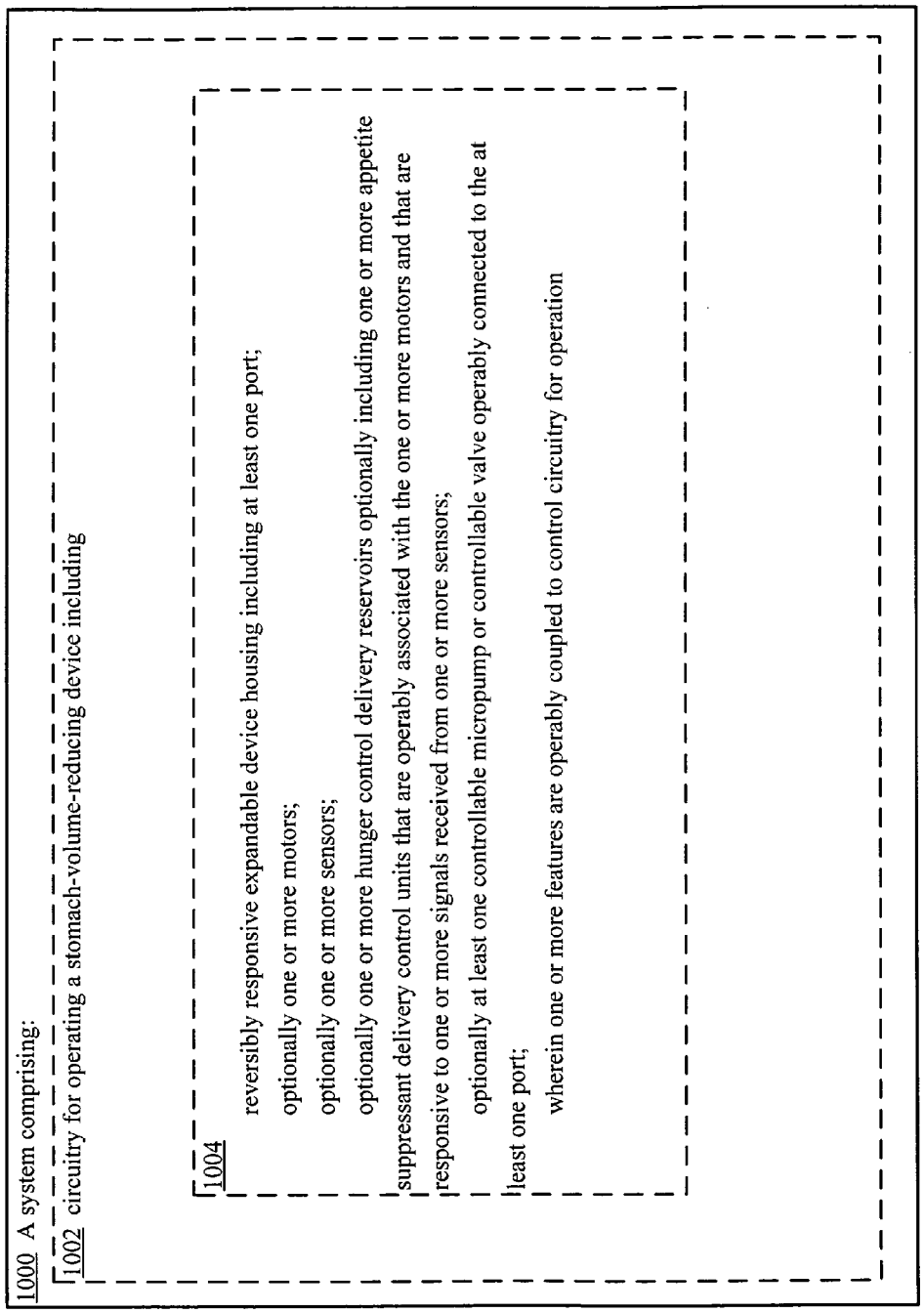
FIG. 10 illustrates a partial view of a particular embodiment of a system as described herein.

FIG. 10 illustrates a partial view of a system 1000 that includes a stomach volume reducing device 1002 including at least one reversibly responsive expandable device housing 199 encasing chemical responsive particles. In an embodiment, the reversibly responsive expandable device housing 199 includes at least one port 144. In an embodiment, the system 1000 includes at least one controllable micropump 123 or controllable valve 125 operably connected to the at least one port 144. In an embodiment, the system 1000 includes at least one sensor 102 configured to sense at least one nerve signal originating from the subject. In an embodiment, the system 1000 includes control circuitry operably coupled to the stomach volume reducing device, the control circuitry configured to operate the at least one port 144 responsive to receiving one or more signals from the at least one sensor 102. In an embodiment, the sensor 102 includes at least one blood pressure cuff.

In an embodiment, the sensor detector component is configured to detect a chemical, pH, or nerve signal.

In an embodiment, the stomach volume reducing device includes one or more hunger control delivery reservoirs 128 that are operably coupled to the one or more ports 144. Device housings 140 may be configured in numerous ways. In an embodiment, a device housing 140 may include one or more hunger control delivery reservoirs 128. In an embodiment, a device housing 140 may include one or more motors 156. In an embodiment, a device housing 140 includes at least one port 144. In an embodiment, a device housing 140 may include one or more entry ports 222. In an embodiment, a device housing 140 may include one or more exit ports 223. In an embodiment, the at least one port 144 includes one or more intelligent responsive matrix that is responsive to one or more environmental condition including at least one of a chemical, pressure, temperature, acoustic signals (e.g., stomach grinding, hiccups, etc.), or electrical signals.

A device housing 140 may be fabricated from numerous types of materials. Examples of such materials include, but are not limited to, metals, elastic chemicals, ceramics, plastics, polymer, nitrile, silicon, cellulose-based plastic, and substantially any combination thereof. In an embodiment, the device housing 140 includes a reversibly responsive expandable device housing 199, for example, includes lactide-glycolide-caprolactone. In an embodiment, the reversibly responsive expandable device housing 199 includes chitosan. In an embodiment, the device housing 199 includes chitosan on at least one external interface. In an embodiment, the reversibly responsive expandable device housing 199 includes a colloid responsive to a carbohydrate. In an embodiment, the device housing expands responsively based on the matrix housed therein. In an embodiment, the reversibly responsive expandable device housing 199 is encased in a container 223. In an embodiment, the container 223 includes an reversibly responsive expandable mesh. In an embodiment, a hunger control delivery reservoir 128 may be configured for implantation within a subject. In an embodiment, a hunger control delivery reservoir 128 may be configured for placement within a body cavity of a subject. In an embodiment, the reversibly responsive expandable device housing 199 includes a polymer formed by a three dimensional model. In an embodiment, the three dimensional model includes a computer generated model. In an embodiment, the reversibly responsive expandable device housing 199 is formed using a three dimensional printer.

In an embodiment, the reversibly responsive expandable device housing 199 is sized for eventual passage through the gastrointestinal tract of a subject. In an embodiment, the device housing 199 is sized for oral administration to a subject. In an embodiment, the device housing 199 is non-toxic.

In an embodiment, the device includes two or more reversibly responsive expandable device housings. In an embodiment, the device housings are non-toxic.

In an embodiment, the reversibly responsive expandable device housing 199 is at least one of biodegradable or biocompatible. In an embodiment, the reversibly responsive expandable device housing 199 includes multiple layers of biodegradable material. In an embodiment, each layer of the multiple layers of biodegradable material is responsive to degradative chemicals. In an embodiment, the degradative chemicals include at least one of an acidic environment, specific protease, exogenously added compound, or pressure. In an embodiment, degradation of one or more layers of the reversibly responsive expandable device housing is predetermined. In an embodiment, the degradation of one or more layers of the reversibly responsive expandable device housing 199 is directed by at least one of a sensor 102 or wireless controller 121.

In an embodiment, the device includes one or more motors 156. In an embodiment, the one or more motors include one or more rotary motors 156. In an embodiment, a rotary motor 156 may operate by imparting angular motion to a rotating structure, such as a shaft. In an embodiment, a rotary motor 156 may operate by imparting angular motion to the motor 156 itself. For example, in an embodiment, a rotary motor 156 may be operably coupled to an immobile threaded structure such that rotation of the rotary motor 156 on the threaded structure will cause the motor 156 to advance on the threaded structure. In an embodiment, a rotary motor 156 that is operably coupled to a hunger control delivery reservoir 128 may be calibrated to administer a select amount of one or more appetite suppressants 162 from the hunger control delivery reservoir 128 to a subject. For example, in an embodiment, a rotary motor 156 may be calibrated to rotate a threaded member 141, or lever member 555 a certain number of times in order to advance an associated moveable member 158 to facilitate administration of an amount of one or more appetite suppressants 162 to a subject. Numerous types of rotary motors 156 may be operably coupled to a hunger control delivery reservoir 128. Examples of such rotary motors 156 include, but are not limited to, electric motors 156, piezoelectric motors 156, ultrasonic piezomotors 156, and the like. Such motors 156 have been described (e.g., Spanner, Survey of the Various Operating Principles of Ultrasonic Piezomotors, White Paper for ACTUATOR 2006, Newscale Technologies, Inc., Victor, N.Y.; Biophan Technologies, Inc., Pittsford, N.Y.; PI (Physik Instrumente) L. P., Auburn, Mass.), incorporated herein by reference.

As shown in the Figures, in an embodiment, one or more motors 156 may include one or more linear motors 156. In an embodiment, a linear motor 156 may operate by imparting substantially linear motion to a moveable structure. For example, in an embodiment, a linear motor 156 may cause a moveable structure to move in a forward motion, a reverse motion, alternately in a forward and reverse direction, or substantially any combination thereof. In an embodiment, one or more linear motors 156 may be operably coupled to one or more moveable structures that are configured as one or more ratchet members. Accordingly, in an embodiment, one or more moveable structures may be operably coupled with one or more moveable members 158 such that operation of one or more linear motors 156 will advance the position of one or more moveable members 158 on the one or more ratchet members. Accordingly, in an embodiment, a linear motor 156 that is operably coupled to a hunger control delivery reservoir 128 may be calibrated to administer a select amount of one or more appetite suppressants 162 from the hunger control delivery reservoir 128 to a subject. For example, in an embodiment, a linear motor 156 may be calibrated to move a ratchet member a certain number of times in order to administer an amount of one or more appetite suppressants 162 to a subject.

In an embodiment, one or more motors 156 may include one or more piezoelectric motors 156. Numerous types of piezoelectric motors 156 may be operably coupled to one or more hunger control delivery reservoirs 128. In an embodiment, one or more linear piezoelectric motors 156 may be operably coupled to a hunger control delivery reservoir 128. In an embodiment, one or more rotary piezoelectric motors 156 may be operably coupled to a hunger control delivery reservoir 128. In an embodiment, one or more ultrasonic piezomotors 156 may be operably coupled to a hunger control delivery reservoir 128. In an embodiment, one or more piezoelectric stepper motors 156 may be operably coupled to a hunger control delivery reservoir 128.

In an embodiment, one or more motors 156 may include one or more stepper motors 156. Stepper motors 156 may be configured in numerous ways. For example, in an embodiment, a stepper motor 156 may be configured as an electromechanical device. In an embodiment, a stepper motor 156 may be configured as a piezoelectric device. In an embodiment, a hunger control delivery reservoir 128 may include one or more stepper motors 156 that are calibrated to facilitate administration of one or more appetite suppressants 162 to a subject. For example, in an embodiment, a hunger control delivery reservoir 128 may include a stepper motor 156 that is operably coupled to a threaded member 141, lever member 555 that is operably coupled to one or more moveable members 158. Rotation of the threaded member 141, lever member 555 by the stepper motor 156 will advance the moveable member 158 and facilitate administration of one or more appetite suppressants 162 to a subject from the hunger control delivery reservoir 128. Accordingly, in an embodiment, operation of a stepper motor 156 may rotate a threaded member 141, lever member 555 such that a moveable member 158 operably coupled to the threaded member 141, lever member 555 is advanced a distance that is directly related to the angular distance traveled by the threaded member 141, lever member 555. Accordingly, in an embodiment, a stepper motor 156 may be calibrated to administer one or more appetite suppressants 162 to a subject. In an embodiment, a stepper motor 156 may be calibrated to administer one or more appetite suppressants 162 to a subject through feedback from one or more sensors 102. For example, in an embodiment, a stepper motor 156 may rotate a threaded member 141, lever member 555 through a known number of turns to deliver an amount of an appetite suppressant to a subject and a sensor may determine the concentration of the appetite suppressant that was delivered to the subject. The amount of appetite suppressant that was delivered may then be correlated to the number of turns of the threaded member 141, lever member 555 and used to calibrate the stepper motor 156.

In an embodiment, one or more motors 156 may include one or more ultrasonic motors 156. In an embodiment, an ultrasonic motor 156 may convert vibrations into linear motion. In an embodiment, an ultrasonic motor 156 may convert vibrations into rotary motion. Ultrasonic motors 156 have been described (e.g., Nanomotion, Inc., Ronkonkoma, N.Y.; PI (Physik Instrumente) L. P., Auburn, Mass.).

In an embodiment, one or more motors 156 may include one or more osmotic motors 156. The device may include numerous types of osmotic motors 156. Osmotic motors 156 have been described (e.g., U.S. Pat. Nos. 6,454,759; 5,112,614; and 7,074,423), incorporated herein by reference. In an embodiment, an osmotic motor 156 may include an osmotic agent that will expand in size upon contact with fluid. Examples of osmotic agents include, but are not limited to, magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, monosaccharides, oligosaccharides, polysaccharides, and substantially any combination thereof. In an embodiment, an osmotic agent may include one or more hydrophilic polymers that swell upon contact with water. Examples of such polymers include, but are not limited to, poly(hydroxy-alkyl methacrylates); poly(vinylpyrrolidone); anionic and cationic hydrogels; polyelectrolyte complexes; poly(vinyl alcohol); formaldehyde or glutaraldehyde; mixtures of methyl cellulose; cross-linked agar and carboxymethylcellulose; mixtures of hydroxypropylmethyl-cellulose and sodium carboxymethylcellulose; polymers of N-vinyllactams; polyoxyethylene-polyoxypropylene gels; polyoxybutylene-polyethylene block copolymer gels; carob gum; polyacrylic gels; polyester gels; polyurea gels; polyether gels; polyamide gels; polypeptide gels; polyamino acid gels; polycellulosic gels; carbopol acidic carboxy polymers; CYANAMER® polyacrylamides; cross-linked indene-maleic anhydride polymers; GOOD-RITE® polyacrylic acids; POLYOX® Polyethylene oxide polymers; starch graft copolymers; and Aqua-Keeps acrylate polymer polysaccharides (e.g., U.S. Pat. No. 7,074,423), incorporated herein by reference.

In an embodiment, one or more hunger control delivery units 146 are operably coupled to one or more reservoir motors 156. In an embodiment, one or more hunger control delivery units 146 are operably coupled to one or more receivers 118 configured to receive one or more signals from one or more sensors 102 that are implanted within a subject. One or more hunger control delivery units 146 may include numerous types of receivers 118. Examples of receivers 118 include, but are not limited to, receivers 118 that receive one or more ultrasonic signals, infrared signals, acoustic signals, optical signals, radio signals, radio frequency signals, microwave signals, and the like. Receivers 118 may receive one or more signals from numerous types of sensors 102. Examples of sensors 102 include, but are not limited to, sensors 102 that are configured to detect one or more chemicals, sensors 102 that are configured to detect blood pressure, sensors 102 that are configured to detect carbon dioxide or other gases, sensors 102 that are configured to detect sugar or protein, sensors 102 that are configured to detect pressure, and the like. In an embodiment, one or more hunger control delivery units 146 may be operably coupled to one or more receivers 118 that are configured to receive one or more signals that facilitate calibration of an associated hunger control delivery reservoir 128. For example, in an embodiment, one or more receivers 118 may be configured to receive one or more signals from one or more sensors 102 that include information related to the concentration of one or more appetite suppressants 162 within a subject. In an embodiment, the hunger control delivery unit 146 may then advance one or more moveable members 158 in response to the one or more signals. The receiver 118 may then receive one or more signals from one or more sensors 102 that include information related to the concentration of the one or more appetite suppressants 162 following administration of the one or more appetite suppressants 162 to the subject from the hunger control delivery reservoir 128. Accordingly, the hunger control delivery unit 146 may then receive information that may be used to calibrate the hunger control delivery reservoir 128 to deliver one or more appetite suppressants 162 to the subject. In an embodiment, one or more hunger control delivery units 146 may receive one or more signals from one or more sensors 102 that are implanted within a subject. Accordingly, in an embodiment, a hunger control delivery reservoir 128 may act directly in response to one or more signals that are transmitted by a sensor that is implanted within a subject. For example, in an embodiment, a hunger control delivery reservoir 128 may receive one or more signals directly from one or more sensors 102 that are implanted within a subject, and may be included in or on the stomach volume reducing device without the signals being received and/or transmitted by a transmitter and/or receiver that is positioned externally to a subject. In an embodiment, the transmitter and/or the receiver 118 is wireless.

In an embodiment, circuitry is configured to operate one or more hunger control delivery units 146 that are operably coupled to the at least one motor 156 and that is responsive to one or more signals received from one or more sensors 102 of the stomach-volume-reducing device. In an embodiment, the one or more signals include at least one of an ultrasonic signal, infrared signal, acoustic signal, optical signal, radio frequency signal, or electromagnetic signal. In an embodiment, control circuitry is configured to operate one or more hunger control delivery units 146 that are operably coupled to one or more receivers 118 that are configured to receive one or more signals that include information related to at least one chemical within a subject.

In an embodiment, the controllable micropump 123 or controllable valve 125 is operably connected to at least one transmitter or receiver 118. In an embodiment, the at least one controllable micropump 123 or controllable valve 125 is operably connected to at least one energy storage device 130.

In an embodiment, one or more hunger control delivery units 146 that are operably coupled to the one or more motors 156 may include one or more hunger control delivery units 146 that are operably coupled to one or more receivers 118 that are configured to receive one or more signals from one or more external interfaces 168. A receiver 118 that is operably coupled to a hunger control delivery unit 146 may be configured to receive numerous types of signals. Examples of such signals include, but are not limited to, analog signals, digital signals, acoustic signals, optical signals, radio signals, wireless signals, hardwired signals, infrared signals, ultrasonic signals, and the like.

In an embodiment, one or more hunger control delivery units 146 that are operably coupled to the one or more motors 156 may include one or more hunger control delivery units 146 that act substantially autonomously. For example, in an embodiment, one or more hunger control delivery units 146 may include operating instructions that direct the acts of the hunger control delivery unit 146 without external interaction. Accordingly, in an embodiment, a hunger control delivery unit 146 may include memory that includes instructions for operating the hunger control delivery unit 146 and a processor 148 that is configured to carry out the instructions. In an embodiment, the one or more hunger control delivery units 146 are configured to receive one or more signals substantially continuously from one or more sensors 102. In an embodiment, the one or more hunger control delivery units 146 are configured to receive one or more signals that include information related to one or more concentrations of at least one chemical within a subject.

In an embodiment, one or more hunger control delivery units 146 that are operably coupled to the one or more motors 156 may include one or more hunger control delivery units 146 that are operably coupled to one or more receivers 118 that are configured to receive one or more infrared signals. Numerous types of infrared transmitters 126 and receivers 118 may be used to send and receive signals. Methods to fabricate infrared transmitters 126 and receivers 118 are known and have been described (e.g., U.S. Pat. Nos. 4,371,814; 5,359,448 and 5,331,450), herein incorporated by reference.

In an embodiment, one or more hunger control delivery units 146 that are operably coupled to the one or more motors 156 may include one or more appetite delivery control units 146 that are operably coupled to one or more receivers 118 that are configured to receive one or more signals that include information related to one or more concentrations of one or more appetite suppressants 162 within a subject. For example, in an embodiment, one or more hunger control delivery reservoirs 128 may include one or more receivers 118 that are configured to receive one or more signals from one or more sensors 102 that are configured to detect cholesterol levels within a subject.

In an embodiment, the device includes a timer 222. In an embodiment, the timer 222 is operably coupled to a transmitter 154 or receiver 118. In an embodiment, the timer transmitter 154 or receiver 118 is operably coupled to at least one motor 156. In an embodiment, the timer transmitter 154 is operably coupled to at least one motor 156 and the motor 156 is operably coupled to a receiver 118. In an embodiment, the motor 156 is responsive to signals received from the timer transmitter 154.

Figure 11:
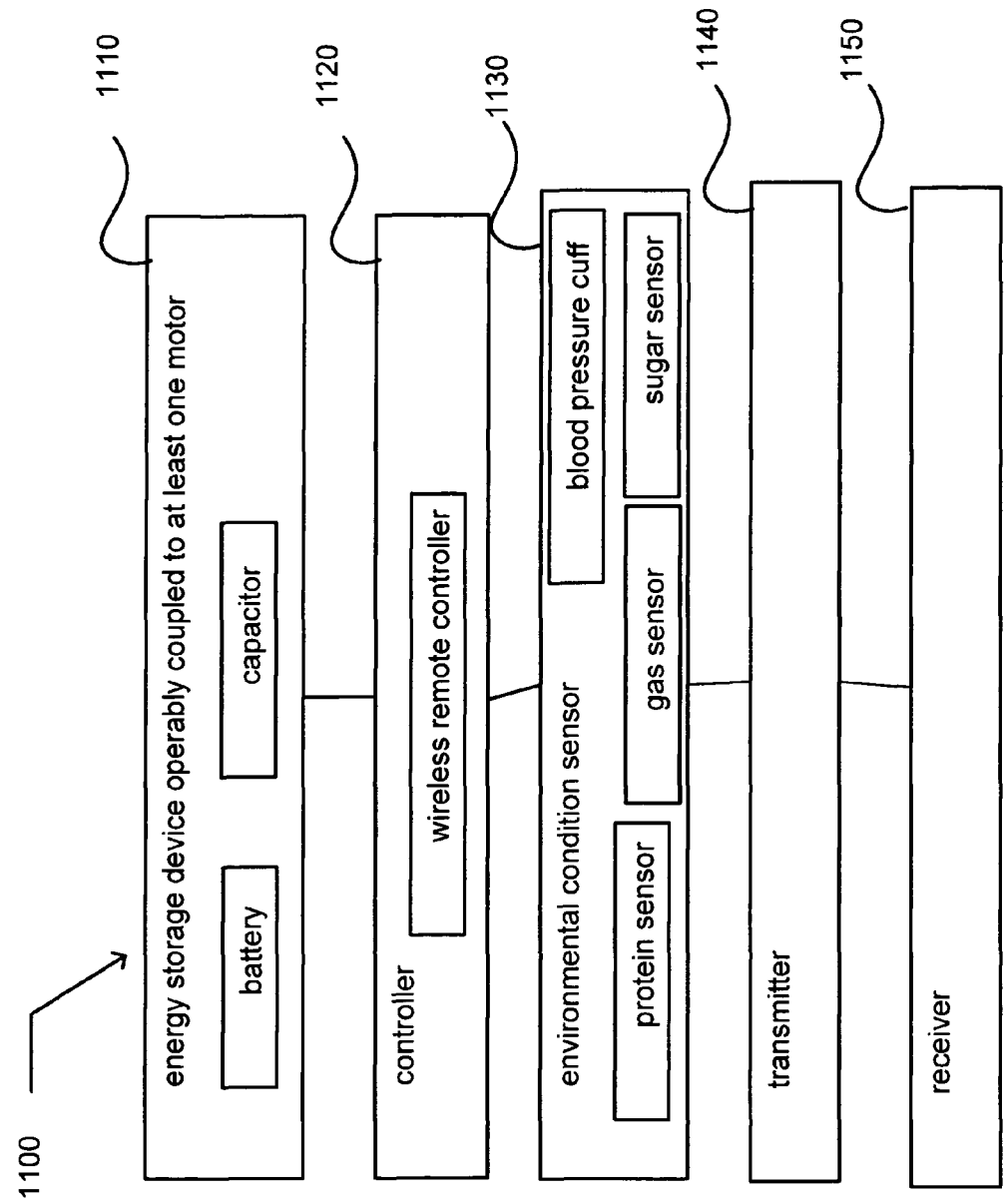
FIG. 11 illustrates a partial view of a particular embodiment including an energy storage device operably coupled to at least one motor as described herein.

FIG. 11 illustrates alternative embodiments of embodiment 200 of hunger control delivery reservoir 128 within system 100. For example, in an embodiment, module 1110, the stomach-volume-reducing device includes an energy storage device (e.g., battery, capacitor, etc.) operably coupled to at least one motor 156. In an embodiment, module 1120, a controller (e.g., wireless remote controller) allows for control of the stomach-volume-reducing device for example, by the subject himself. See FIG. 3. In an embodiment, module 1130, the device includes at least one environmental condition sensor (e.g., blood pressure cuff, protein sensor, gas sensor, sugar sensor, etc.). In an embodiment, module 1140, the stomach-volume-reducing device includes a transmitter. In an embodiment, module 1150, the stomach-volume-reducing device includes a receiver.

In an embodiment, one or more ports 144 may include one or more shape memory closures. Shape memory closures may be fabricated from numerous types of material. In an embodiment, one or more shape memory materials may be magnetic shape-memory materials. Magnetic shape-memory materials change shape in response to a magnetic field. Examples of magnetic shape-memory materials include, but are not limited to, nickel-manganese-gallium alloys, nickel-titanium alloys, copper-zinc-nickel alloys, and copper-aluminum-nickel alloys. In an embodiment, shape memory materials may be shape memory polymers. In an embodiment, shape memory polymers change shape in response to temperature. In an embodiment, a shape memory polymer may include oligo(ε-caprolactone)diol and crystallisable oligo(p-dioxanone)diol. In an embodiment, a shape memory polymer may include combinations of N,N,N',N'-Tetrakis(2-hydroxypropyl)ethylenediamine (HPED), triethanolamine (TEA), butane diol (BD), and hexamethylene diisocynate (HDI), with the following range of compositions based on 1 moles equivalent of HDI: 0.1 to 0.5 moles HPED, 0 to 0.54 moles of TEA, and 0 to 0.40 moles of BD. In an embodiment, shape memory materials may be light-induced shape-memory polymers (Lendlein et al., Letters to Nature, Nature 434:879-882 (2005)), incorporated by reference. Light-induced shape-memory polymers change shape in response to light.

In an embodiment, one or more ports 144 may include one or more slit valves. In an embodiment, one or more hunger control delivery devices 128 may include one or more slit valves. Slit valves have been described (e.g., U.S. Pat. No. 6,217,906), which is incorporated by reference.

In an embodiment, one or more ports 144 may include one or more electromagnetic closures. In an embodiment, one or more hunger control delivery reservoirs 128 may include one or more electromagnetic closures. Electromagnetic closures may be configured in numerous ways. In an embodiment, an electromagnetic closure may include a plug that is configured to eliminate flow through a port 144. The plug may be operably coupled to a spring such that the plug is forced into a port 144 by the spring. The plug may be removed from the port 144 through application of a magnetic field to the plug through use of an electromagnet. Accordingly, flow through the exit port may be controlled through application of a magnetic field to the plug. In an embodiment, an electromagnetic closure for an exit port may include a hatchway mechanism wherein a door that covers the exit port may be opened through application of a magnetic field to the door. In an embodiment, one or more ports 144 may be configured to facilitate exit of one or more appetite suppressants 162 from a hunger control delivery reservoir 128 to the subject.

In an embodiment, one or more ports 144 may include one or more piezoelectric closures. In an embodiment, one or more piezoelectric closures may be configured such that application of an electric current to one or more piezoelectric materials within the closure causes the one or more piezoelectric materials to distort and open a port 144. In an embodiment, one or more piezoelectric closures may be configured such that application of an electric current to one or more piezoelectric materials within the closure causes the one or more piezoelectric materials to distort and close a port 144. Piezoelectric valves have been described (e.g., Lindler and Anderson, Piezoelectric Direct Drive Servovalve, SPIE Paper 4698-53, Industrial and Commercial Applications of Smart Structures Technologies, San Diego, March 2002), incorporated herein by reference.

In an embodiment, one or more device housings 140 that are operably coupled to the one or more moveable members 158 and the one or more ports 144 may include one or more reservoirs 128. In an embodiment, one or more device housings 140 may be configured to include one or more reservoirs 128 that are positioned between one or more moveable members 158 and one or more ports 144. Accordingly, movement of the one or more moveable members 158 toward the one or more ports 144 will cause one or more appetite suppressants 162 contained within the one or more reservoirs 128 to be extruded through the one or more ports 144.

In an embodiment, one or more device housings 140 that are operably coupled to the one or more moveable members 158 and the one or more ports 144 may include one or more energy storage devices 134. A device housing 140 may be operably coupled to numerous types of energy storage devices 134. Examples of such energy storage devices 134 include, but are not limited to, batteries (e.g., thin-film batteries), capacitors, electromagnetic receivers, and the like.

In an embodiment, one or more device housings 140 that are operably coupled to the one or more moveable members 158 and the one or more ports 144 may include one or more transmitters 126. A device housing 140 may include numerous types of transmitters 126. Examples of such transmitters 126 include, but are not limited to, transmitters that transmit one or more analog signals, digital signals, acoustic signals, optical signals, radio signals, wireless signals, hardwired signals, infrared signals, ultrasonic signals, and the like.

In an embodiment, one or more device housings 140 that are operably coupled to the one or more moveable members 158 and the one or more ports 144 may include one or more ratchet members 109. In an embodiment, one or more device housings 140 may be configured to include one or more ratchet members 109 that are operably coupled with one or more moveable members 158. In an embodiment, the one or more ratchet members 109 may be configured to move the one or more operably coupled moveable members 158 toward one or more ports 144. In an embodiment, the device housing 140 may be configured to include one or more reservoirs 142 that are positioned between the one or more ports 144 and the one or more moveable members 158. Accordingly, in an embodiment, movement of the one or more ratchet members 109 by one or more motors 156 will move the one or more moveable members 158 toward the one or more ports 144 and facilitate extrusion of one or more appetite suppressants 162 that are contained within the one or more reservoirs 128.

Figure 12:
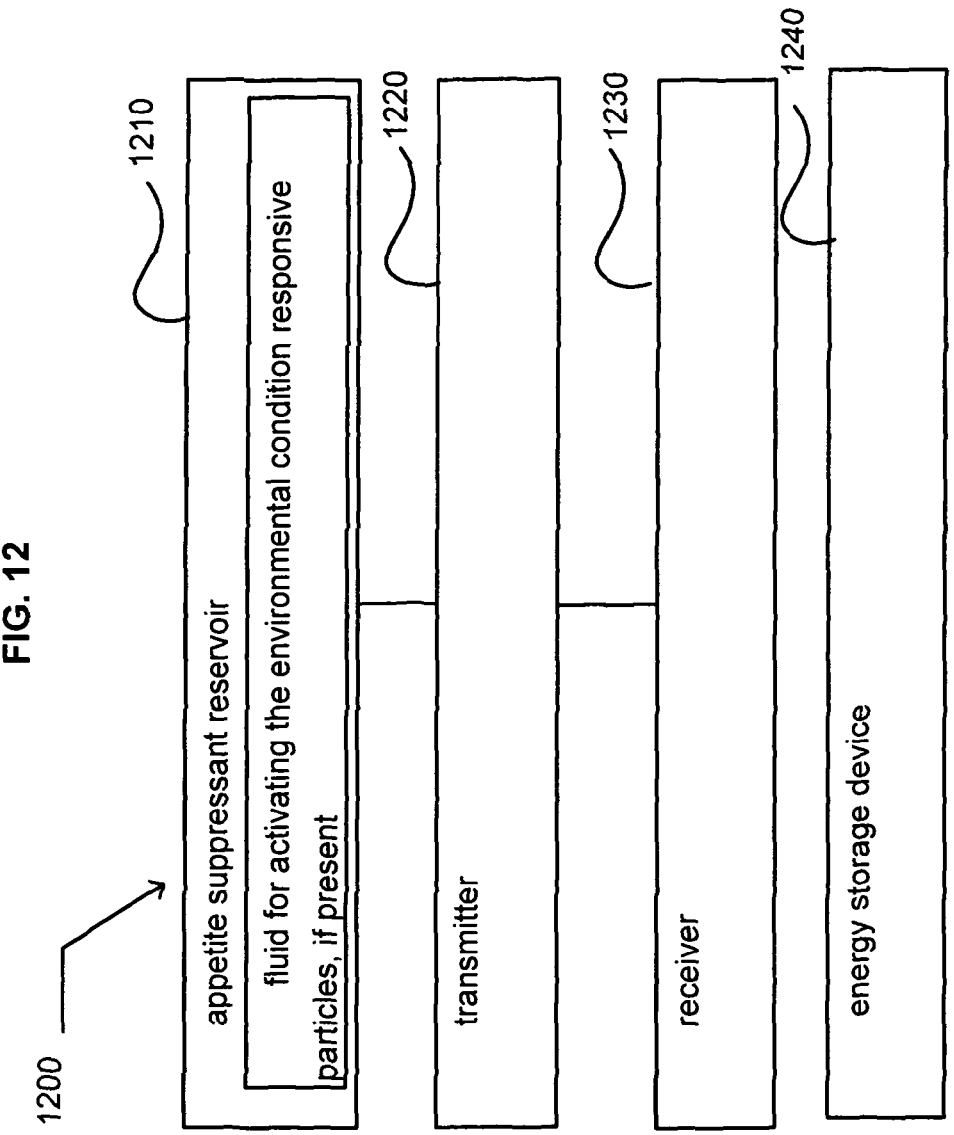
FIG. 12 illustrates a partial view of a particular embodiment including an appetite suppressant reservoir as described herein.

As illustrated in FIG. 12, in an embodiment of the stomach-volume-reducing device 1200, module 1210 includes an appetite suppressant reservoir and optionally fluid for activating the environmental condition responsive particles, if present. In an embodiment, module 1220, the device includes a transmitter or, module 1230, a receiver, or module 1240, an energy storage device.

Figure 13:
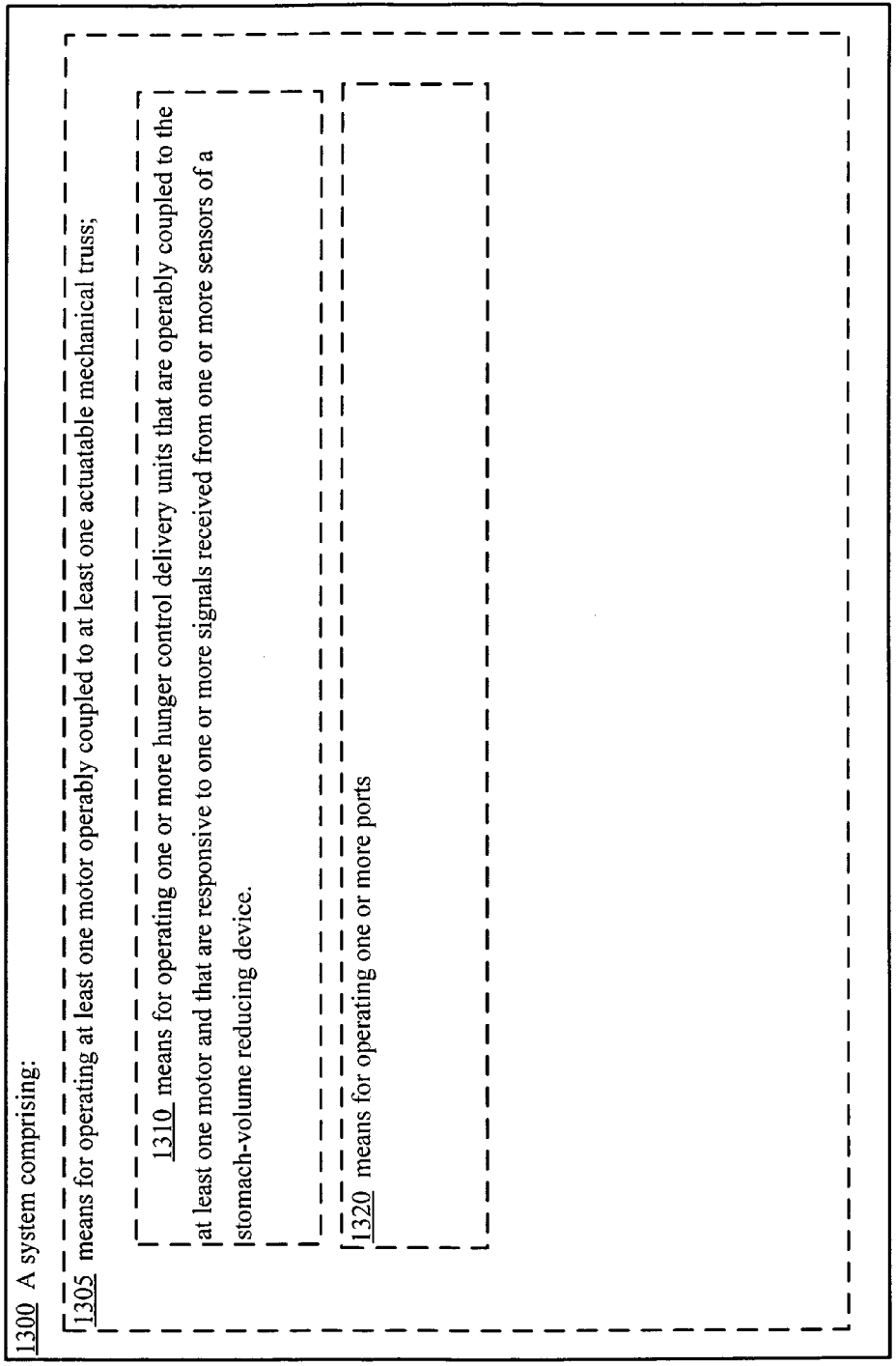
FIG. 13 illustrates a partial view of a particular embodiment of a system described herein.

As illustrated in FIG. 13, a system 1300 includes means 1305 for operating at least one motor operably coupled to at least one actuatable mechanical truss; 1310 means for operating one or more appetite suppressant delivery control units that are operably coupled to the at least one motor and that are responsive to one or more signals received from one or more sensors of a stomach-volume reducing device, and in one embodiment 1320, means for operating one or more ports.

Figure 14:
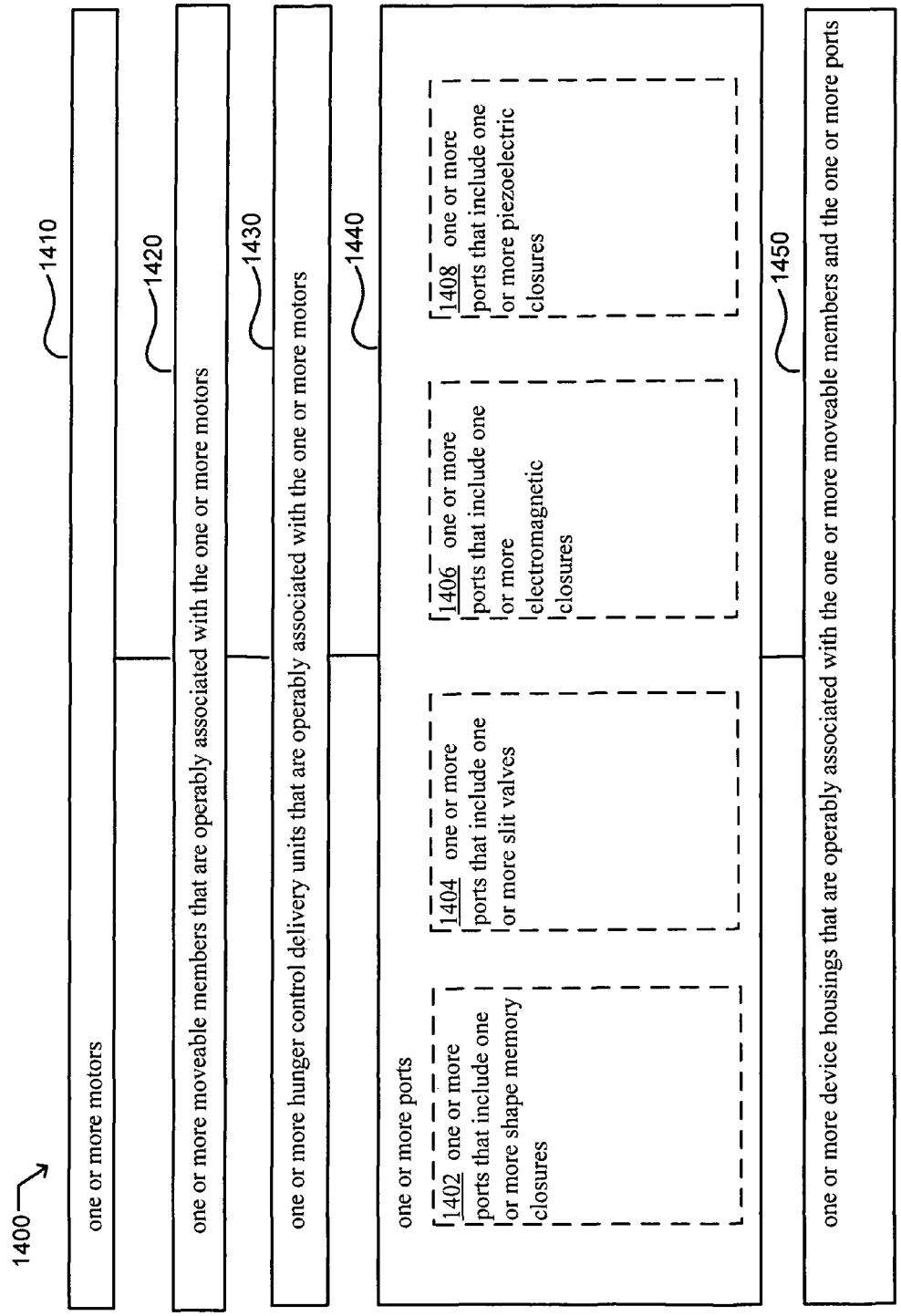
FIG. 14 illustrates a partial view of a particular embodiment of a system including one or more ports as described herein.

As illustrated in FIG. 14, in an embodiment 1400 of the stomach-volume-reducing device, the device includes one or more motors 1410, one or more moveable members that are operably associated with the one or more motors 1420, one or more hunger control delivery units that are operably associated with the one or more motors 1430, one or more ports 1440. In an embodiment, 1402, one or more ports include one or more shape memory closures. In an embodiment 1404, one or more ports include one or more slit valves. In an embodiment 1406, one or more ports include one or more electromagnetic closures. In an embodiment 1408, one or more ports include one or more piezoelectric closures. In an embodiment 1450, one or more device housings are operably associated with the one or more moveable members and the one or more ports.

Figure 15:
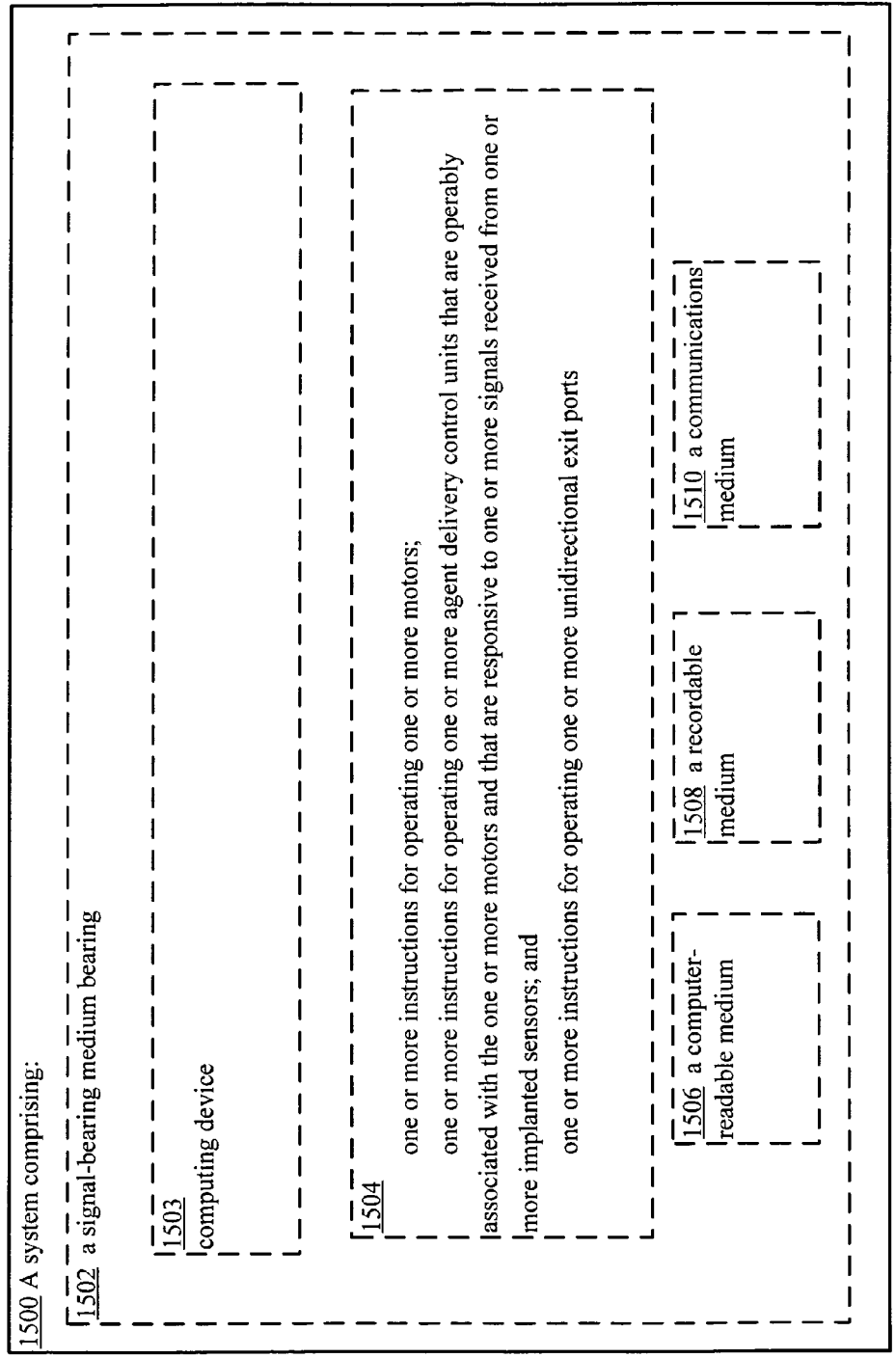
FIG. 15 illustrates a partial view of a particular embodiment of a system described herein.

FIG. 15 illustrates a partial view of a system 1500 that includes a computer program 1504 for executing a computer process on a computing device 1503. An embodiment of system 1500 is provided using a signal-bearing medium 1502 bearing one or more instructions for operating one or more motors 156; one or more instructions for operating one or more hunger control delivery units 146 that are operably coupled to the one or more motors 156 and that are responsive to one or more signals received from one or more implanted sensors 102; and one or more instructions for operating one or more ports 144. The one or more instructions may be, for example, computer executable and/or logic-implemented instructions. In an embodiment, the signal-bearing medium 1502 may include a computer-readable medium 1506. In an embodiment, the signal-bearing medium 1502 may include a recordable medium 1508. In an embodiment, the signal-bearing medium 1502 may include a communications medium 1510.

Figure 16:
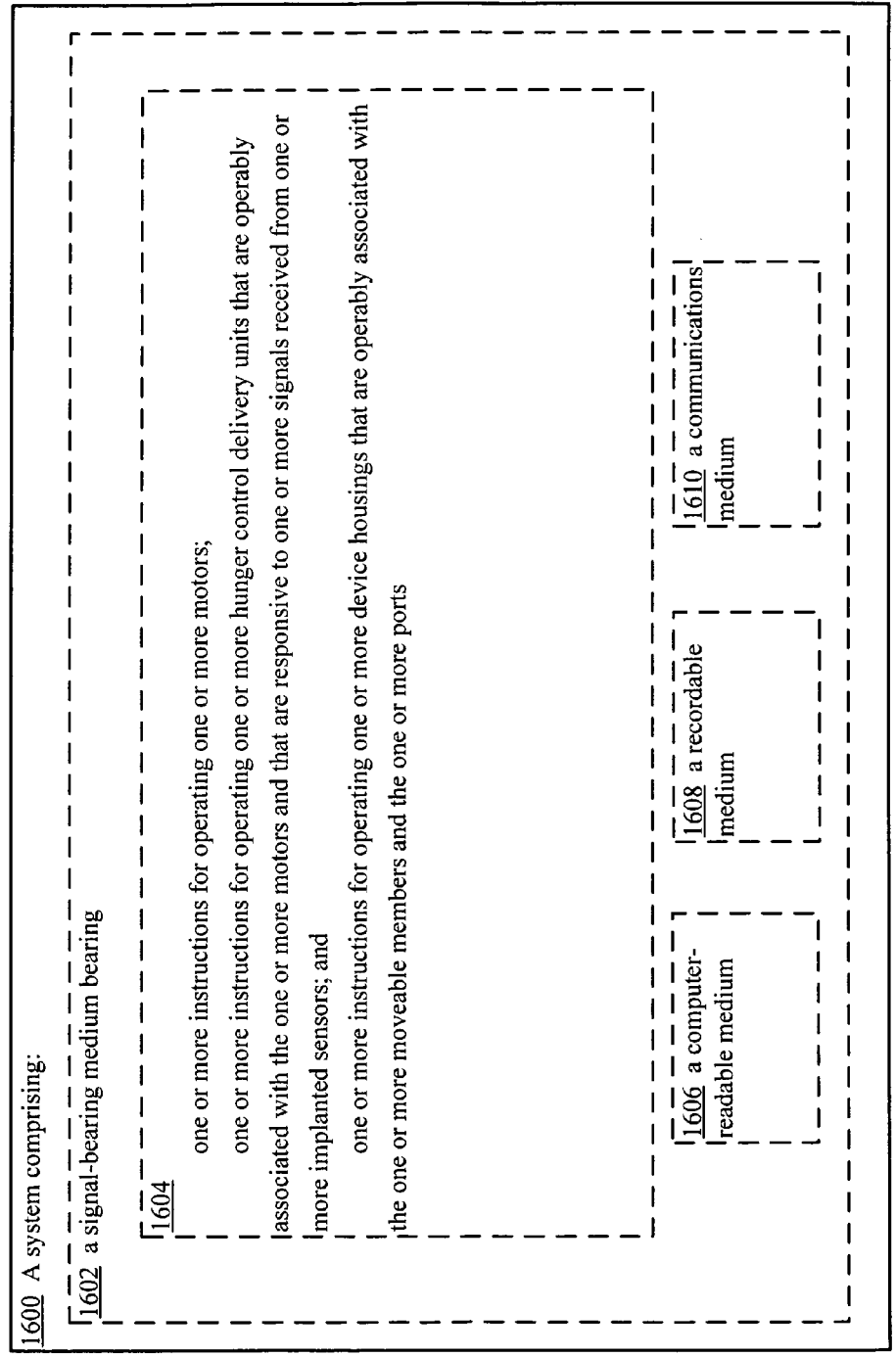
FIG. 16 illustrates a partial view of a particular embodiment of a system described herein.

FIG. 16 illustrates a partial view of a system 1600 that includes a computer program 1604 for executing a computer process on a computing device 1603. An embodiment of system 1600 is provided using a signal-bearing medium 1602 bearing one or more instructions for operating one or more motors 156; one or more instructions for operating one or more hunger control delivery units 146 that are operably coupled to the one or more motors 156 and that are responsive to one or more signals received from one or more implanted sensors 102; one or more instructions for operating one or more ports 144; and one or more instructions for operating one or more device housings that are operably coupled to the one or more moveable members and the one or more ports. The one or more instructions may be, for example, computer executable and/or logic-implemented instructions. In an embodiment, the signal-bearing medium 1602 may include a computer-readable medium 1606. In an embodiment, the signal-bearing medium 1602 may include a recordable medium 1608. In an embodiment, the signal-bearing medium 1602 may include a communications medium 1610.

FIGS. 17A and 17B illustrate embodiments of a hunger control delivery reservoir 128 that includes a piezoelectric linear motor 156 that is operably coupled to a moveable member 158 through a ratcheted member 2500. The hunger control delivery reservoir 128 includes a device housing 140, a hunger control delivery unit 146, one or more appetite suppressants 162, and a port 144. The moveable member 158 is illustrated in an advanced position relative to the position of the moveable member 158 as illustrated in FIG. 17A.

FIG. 18A illustrates an embodiment of a hunger control delivery reservoir 128 that includes a piezoelectric linear motor 156 that is operably coupled to a moveable member 158 through a ratcheted member 2500. The hunger control delivery reservoir 128 includes a device housing 140, a hunger control delivery unit 146, one or more appetite suppressants 162, a port 144, and moveable member retainers 2600.

FIG. 18B illustrates an embodiment of a hunger control delivery reservoir 128 that includes a piezoelectric linear motor 156 that is operably coupled to a moveable member 158 through a ratcheted member 2500. The hunger control delivery reservoir 128 includes a device housing 140, a hunger control delivery unit 146, one or more appetite suppressants 162, a port 144, and moveable member retainers 2600. The moveable member 158 is illustrated in an advanced position relative to the position of the moveable member 158 as illustrated in FIG. 26A.

FIG. 19A illustrates an embodiment of a hunger control delivery reservoir 128 that includes an osmotic motor 156 that facilitates movement of a moveable member 158 through introduction of solute into the osmotic motor 156. The hunger control delivery reservoir 128 includes a device housing 140, a hunger control delivery unit 146, one or more appetite suppressants 162, an electromagnetic exit port 2000 that is shown in the closed position, and an electromagnetic entry port 2700 that is shown in the closed position.

FIG. 19B illustrates an embodiment of a stomach volume reducing device that optionally includes a hunger control delivery reservoir 128 and including an osmotic motor 156 that facilitates movement of a moveable member 158 through introduction of solute into the osmotic motor 156. The hunger control delivery reservoir 128 includes a reservoir housing 140, a hunger control delivery unit 146, one or more appetite suppressants 162, an electromagnetic exit port 2000 that is shown in the open position, and an electromagnetic entry port 2700 that is shown in the open position. The moveable member 158 is illustrated in an advanced position relative to the position of the moveable member 158 as illustrated in FIG. 27A.

FIG. 20A illustrates an embodiment of a hunger control delivery reservoir 128 that includes an osmotic motor 156 that facilitates movement of a moveable member 158 through introduction of solute into the osmotic motor 156. The hunger control delivery reservoir 128 includes a device housing 140, hunger control delivery units 146, one or more appetite suppressants 162, an exit port 2800 made from a shape memory material that is shown in the closed position, and an entry port 2802 made from a shape memory material that is shown in the closed position.

FIG. 21A illustrates an embodiment of a hunger control delivery reservoir 128 that includes an assembly of subject hunger control delivery reservoirs 128. Each hunger control delivery reservoir 128 includes an osmotic motor 156 that facilitates movement of a moveable member 158 through introduction of solute into the osmotic motor 156. Each hunger control delivery reservoir 128 includes a device housing 140, hunger control delivery units 146, one or more appetite suppressants 162, an exit port 2800 made from a shape memory material that is shown in the closed position, and an entry port 2802 made from a shape memory material that is shown in the closed position.

FIG. 21B illustrates an embodiment of a hunger control delivery reservoir 128 that includes an assembly of subject hunger control delivery reservoirs 128. Each hunger control delivery reservoir 128 includes an osmotic motor 156 that facilitates movement of a moveable member 158 through introduction of solute into the osmotic motor 156. Each hunger control delivery reservoir 128 includes a device housing 140, hunger control delivery units 146, one or more appetite suppressants 162, an exit port 2800 made from a shape memory material that is shown in the open position, and an entry port 2802 made from a shape memory material that is shown in the open position. The moveable members 158 are shown in an advanced position relative to their position as illustrated in FIG. 29A.

FIG. 22A illustrates a side-view of an embodiment of sensor 102 that includes a sensor control unit 104, and a sensor housing 184 that includes selectively accessible sections 112 that are covered with a sacrificial layer 3000 and which enclose sensor detectors 114. All of the selectively accessible sections 112 are shown as being sequestered from the outside environment.

FIG. 22B illustrates a side-view of an embodiment of sensor 102 that includes a sensor control unit 104, and a sensor housing 184 that includes selectively accessible sections 112 that are covered with a sacrificial layer 3000 and which enclose sensor detectors 114. The sacrificial layer 3000 is shown as having been removed from three of the selectively accessible sections 112 of the sensor 102 to expose three sensor detectors 114 to the outside environment.

FIG. 23A illustrates a side-view of an embodiment of sensor 102 that includes a sensor control unit 104, and a sensor housing 184 that includes selectively accessible sections 112 that are covered with a shape memory material 3100 and which enclose sensor detectors 114. All of the selectively accessible sections 112 are shown as being sequestered from the outside environment.

FIG. 23B illustrates a side-view of an embodiment of sensor 102 that includes a sensor control unit 104, and a sensor housing 184 that includes selectively accessible sections 112 that are covered with a shape memory material 3100 and which enclose sensor detectors 114. The shape memory material 3100 covering two of the selectively accessible sections 112 is shown as having been reshaped to expose two sensor detectors 114 to the outside environment.

FIG. 23C illustrates a top-view of an embodiment of sensor 102 that includes a sensor control unit 104, and a sensor housing 184 that includes selectively accessible sections 112 and which enclose sensor detectors 114.

Figure 24:
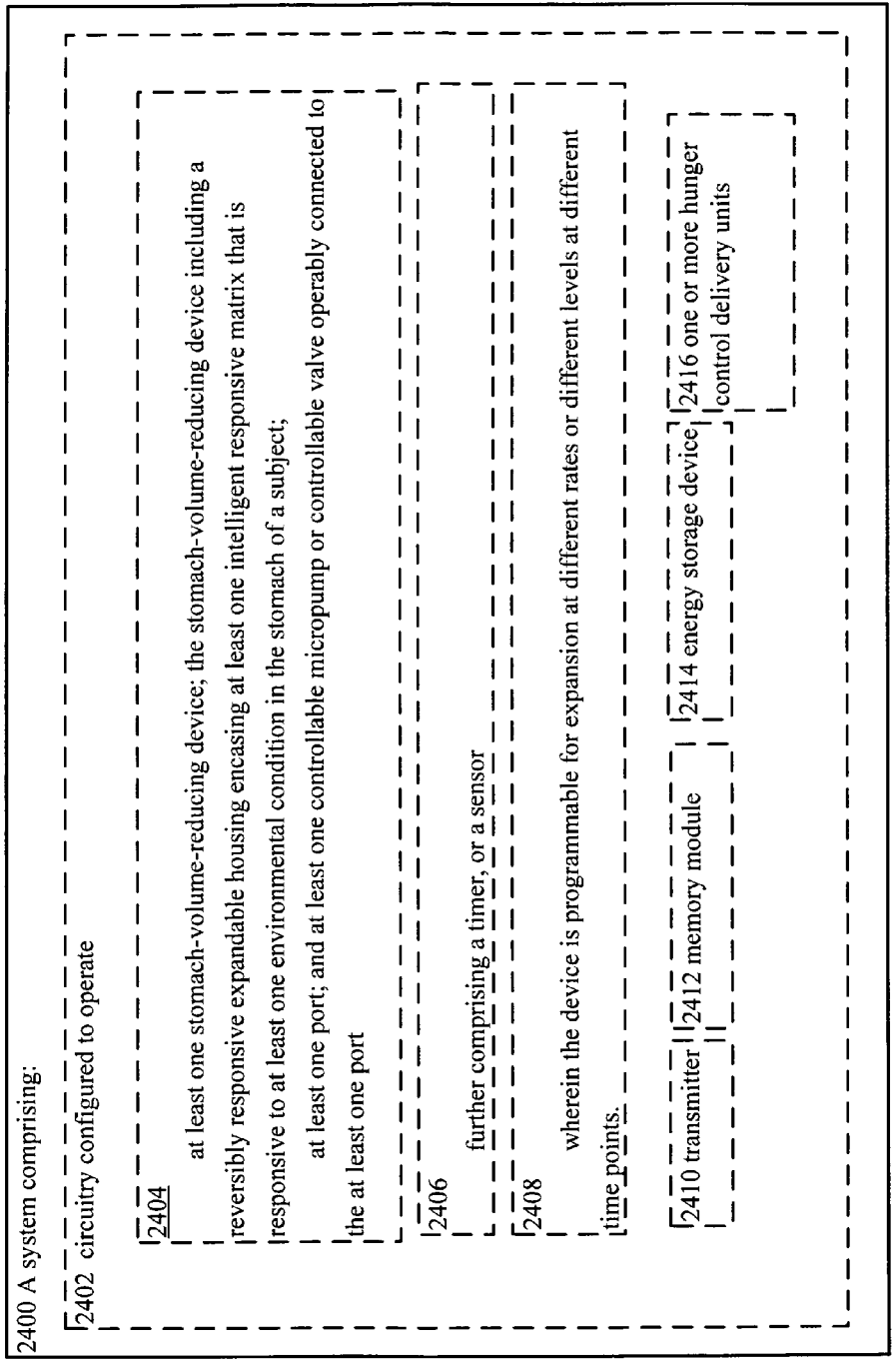
FIG. 24 illustrates a partial view of a particular embodiment of a system including circuitry as described herein.

As illustrated in FIG. 24, a system 2400, includes circuitry 2402 configured to operate 2404 at least one stomach-volume-reducing device; the stomach-volume-reducing device including a reversibly responsive expandable housing encasing at least one intelligent responsive matrix that is responsive to at least one environmental condition in the stomach of a subject; at least one port; and at least one controllable micropump or controllable valve operably connected to the at least one port. In an embodiment 2406, the device further comprises a timer or a sensor. In an embodiment 2408, the device is programmable for expansion at different rates or different levels at different time points. In an embodiment 2410, the device includes a transmitter. In an embodiment 2412, the device includes a memory module. In an embodiment 2414, the device includes an energy storage device. In an embodiment 2416, the device includes one or more hunger control delivery units.

Figure 25:
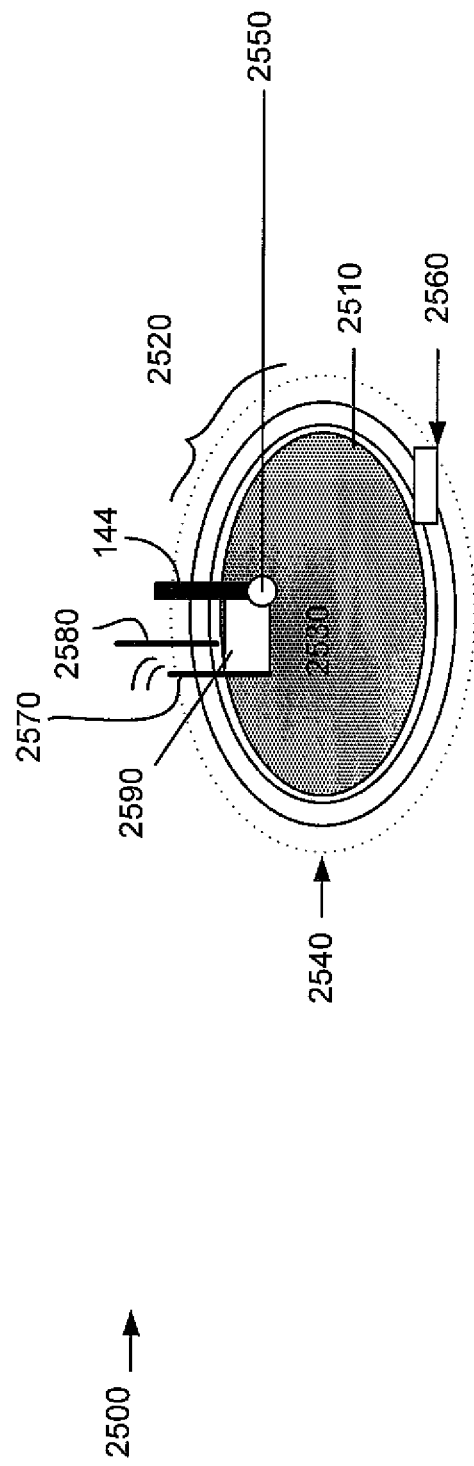
FIG. 25 illustrates a partial view of a particular embodiment of a device including an intelligent responsive matrix as described herein.

As illustrated in FIG. 25, in an embodiment, the stomach-volume-reducing device 2500 includes multiple layers of biodegradable materials 2510. In an embodiment, the device housing includes a reversibly responsive expandable device housing 2520 optionally including or encasing at least one intelligent responsive matrix 2530. In an embodiment, at least one of the biodegradable materials 2510 includes a mesh 2540. In an embodiment, the device 2500 includes at least one energy storage device 2550, sensor 2560, port 144, transmitter 2570, receiver 2580, or controllable valve or pump 2590.

Figure 26:
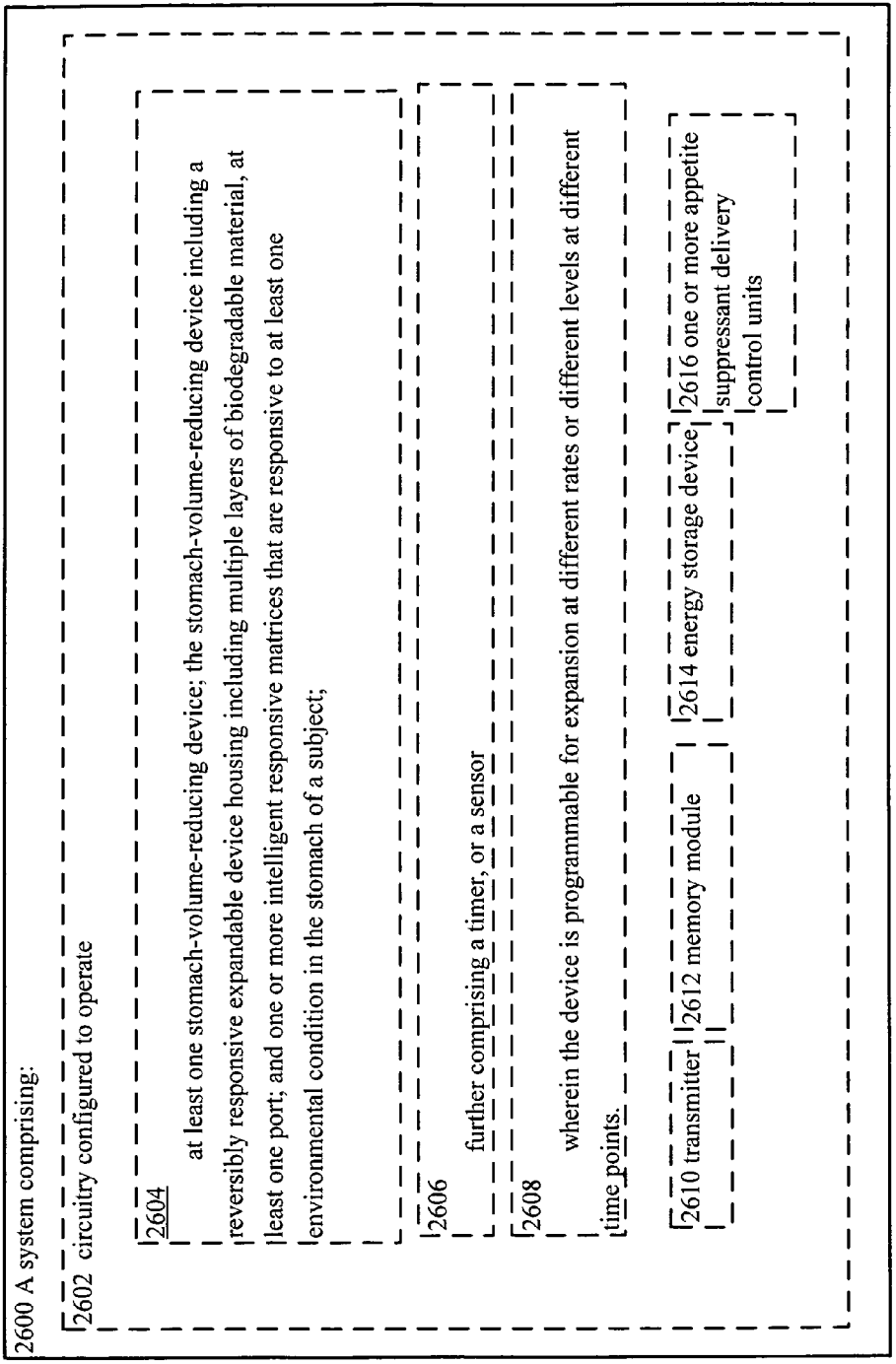
FIG. 26 illustrates a partial view of a particular embodiment of a system including circuitry as described herein.

As illustrated in FIG. 26, in an embodiment a system 2600 includes circuitry configured 2602 to operate 2604 at least one stomach-volume-reducing device; the stomach-volume-reducing device including a reversibly responsive expandable device housing including multiple layers of biodegradable materials, at least one port; and one or more intelligent responsive matrices that are responsive to at least one environmental condition in the stomach of a subject; optionally 2606 one sensor or timer, 2610 transmitter, 2612 memory module, 2614 energy storage device, or 2616 one or more hunger control delivery units. In an embodiment, 2608 the device is programmable for expansion at different rates or different levels at different time points.

Figure 27:
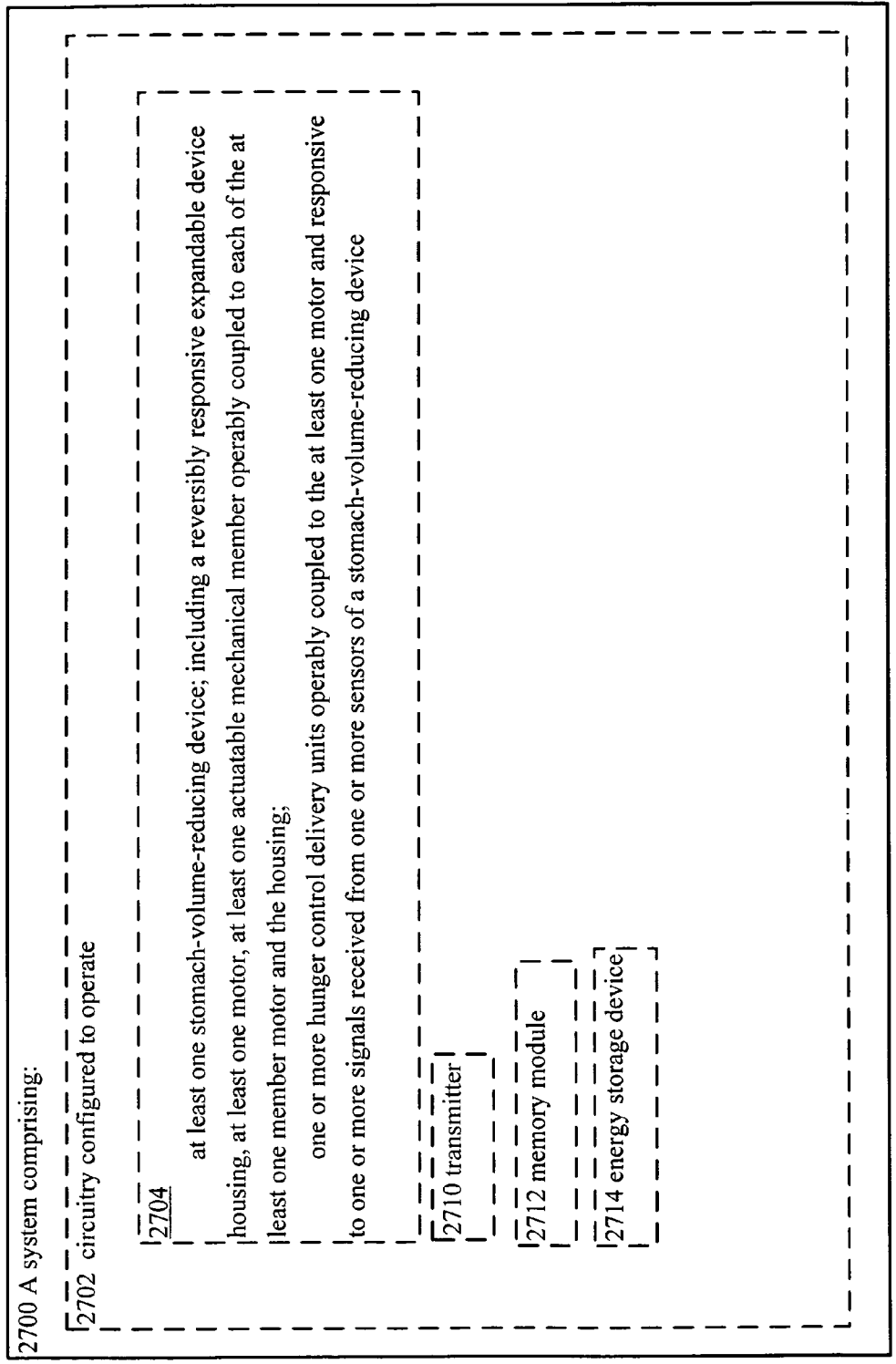
FIG. 27 illustrates a partial view of a particular embodiment of a system including circuitry as described herein.

As illustrated in FIG. 27, in an embodiment a system 2700 includes circuitry 2702 configured to operate 2705 at least one stomach-volume-reducing device, the device including a reversibly responsive expandable device housing, at least one motor, at least one actuatable mechanical member operably coupled to each of the at least one motor and the housing, optionally including one or more hunger control delivery units operably coupled to the at least one motor and responsive to one or more signals received from one or more sensors of a stomach-volume-reducing device. In an embodiment 2710 the device includes a transmitter. In an embodiment, the device includes at least one of a memory module 2712, or an energy storage device 2714.

Figure 28:
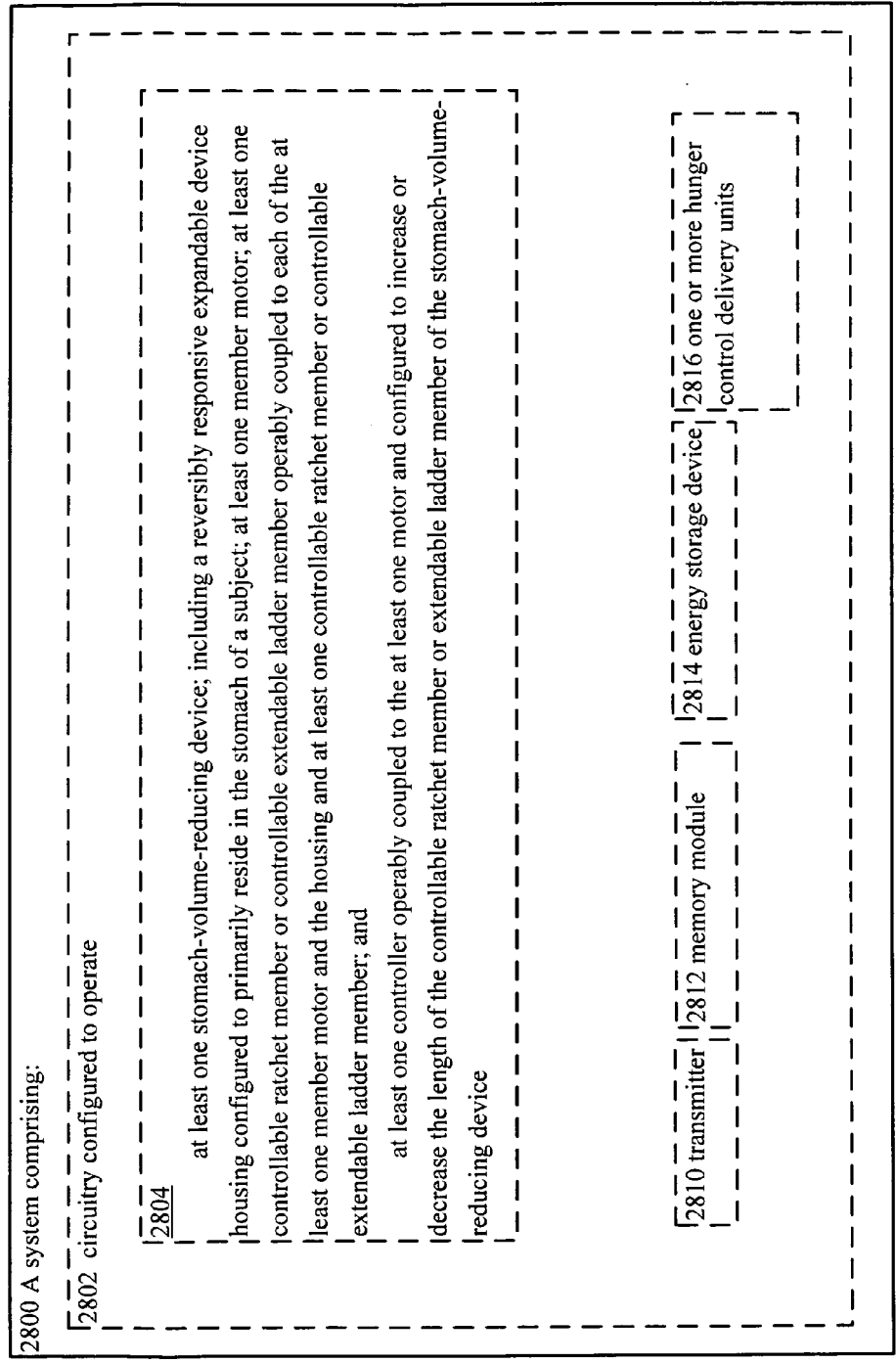
FIG. 28 illustrates a partial view of a particular embodiment of a system as described herein.

As illustrated in FIG. 28, in an embodiment, a system 2800 comprises 2802 circuitry configured to operate 2804 at least one stomach-volume-reducing device, including a reversibly responsive expandable device housing configured to primarily reside in the stomach of a subject; at least one member motor, at least one controllable ratchet member or controllable extendable ladder member operably coupled to each of the at least one member motor and the housing and at least one controllable ratchet member or controllable extendable ladder member; and at least one controller operably coupled to the at least one motor and configured to increase or decrease the length of the controllable ratchet member or extendable ladder member of the stomach-volume-reducing device. In an embodiment, the device includes at least one of a transmitter 2810, memory module 2812, energy storage device 2814, or one or more hunger control delivery units 2816.

Figure 29:
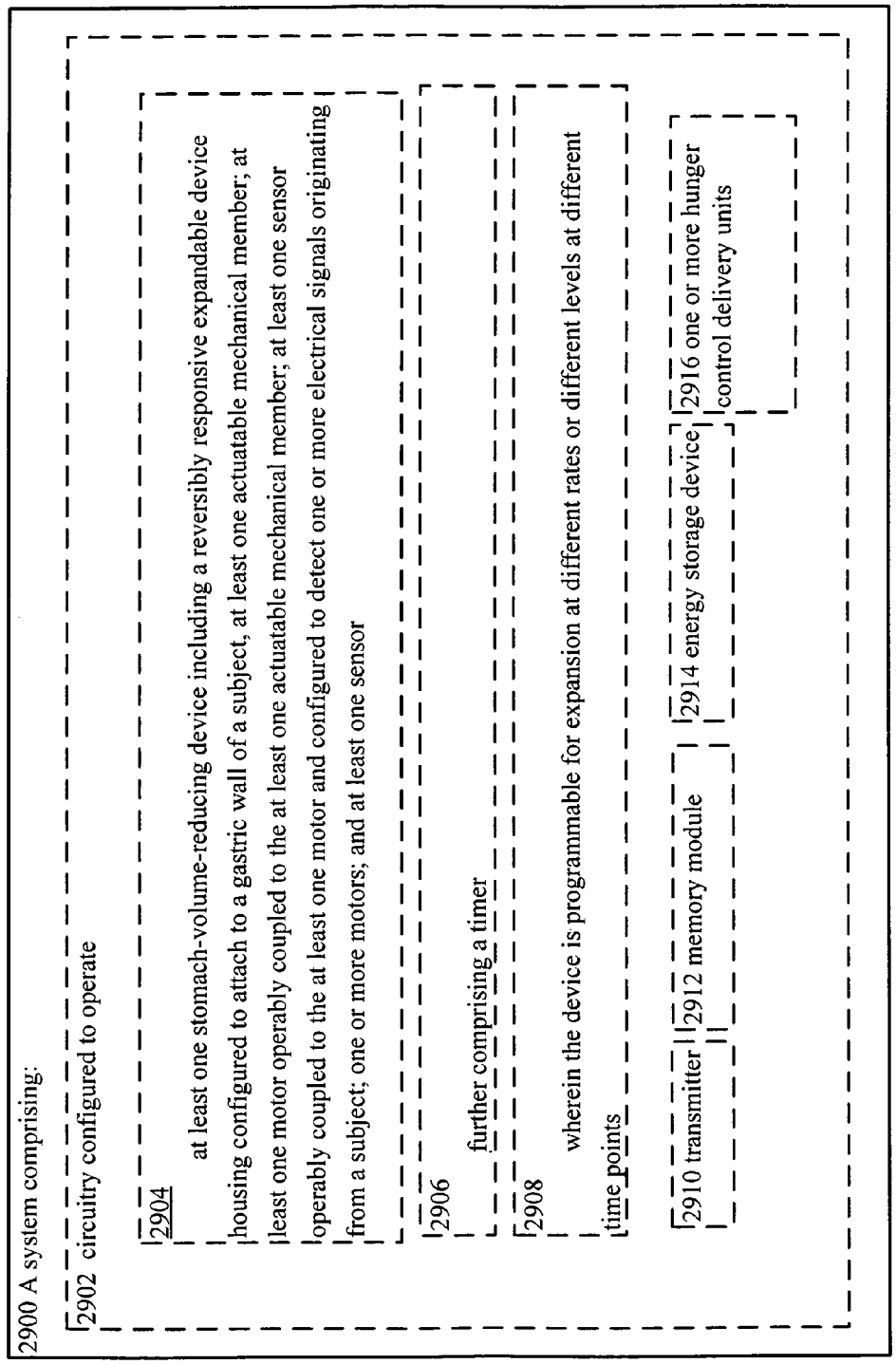
FIG. 29 illustrates a partial view of a particular embodiment of a system as described herein.

As illustrated in FIG. 29, in an embodiment, a system 2900 comprises circuitry 2902 configured to operate 2904 at least one stomach-volume-reducing device including a reversibly responsive expandable device housing configured to attach to a gastric wall of a subject, at least one actuatable mechanical member; at least one motor operably coupled to the at least one actuatable mechanical member; at least one sensor operably coupled to the at least one motor and configured to detect one or more electrical signals originating from a subject; one or more motors; and at least one sensor. In an embodiment, the device includes 2906 a timer. In an embodiment 2908 the device is programmable for expansion at different rates or different levels at different time points. In an embodiment, the device includes 2910 a transmitter, or 2912 a memory module. In an embodiment, the device includes an 2914 energy storage device, or 2916 one or more hunger control delivery units.

Figure 30:
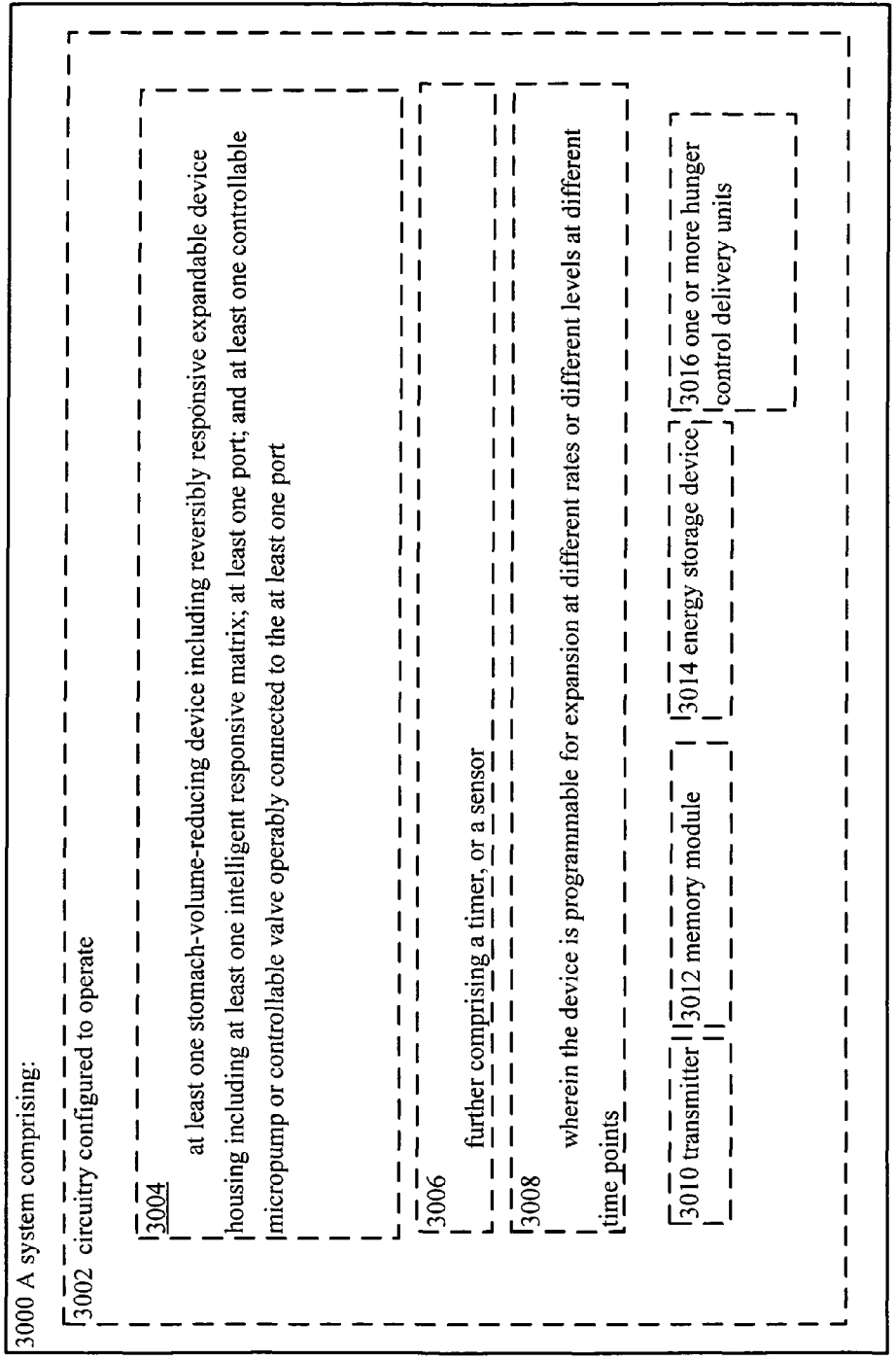
FIG. 30 illustrates a partial view of a particular embodiment of a system as described herein.

As illustrated in FIG. 30, in an embodiment 3000, a system includes circuitry 3002 configured to operate 3004 at least one stomach-volume-reducing device including reversibly responsive expandable device housing including at least one intelligent responsive matrix, at least one port; and at least one controllable micropump or controllable valve operably connected to the at least one port. In an embodiment, the device further comprises 3006 a timer or sensor. In an embodiment 3008 the device is programmable for expansion at different rates or different levels at different time points. In an embodiment, the device includes a transmitter 3010. In an embodiment, the device includes a memory module 3012. In an embodiment, the device includes an energy storage device 3014. In an embodiment, the device includes one or more hunger control delivery units 3016.

Figure 31:
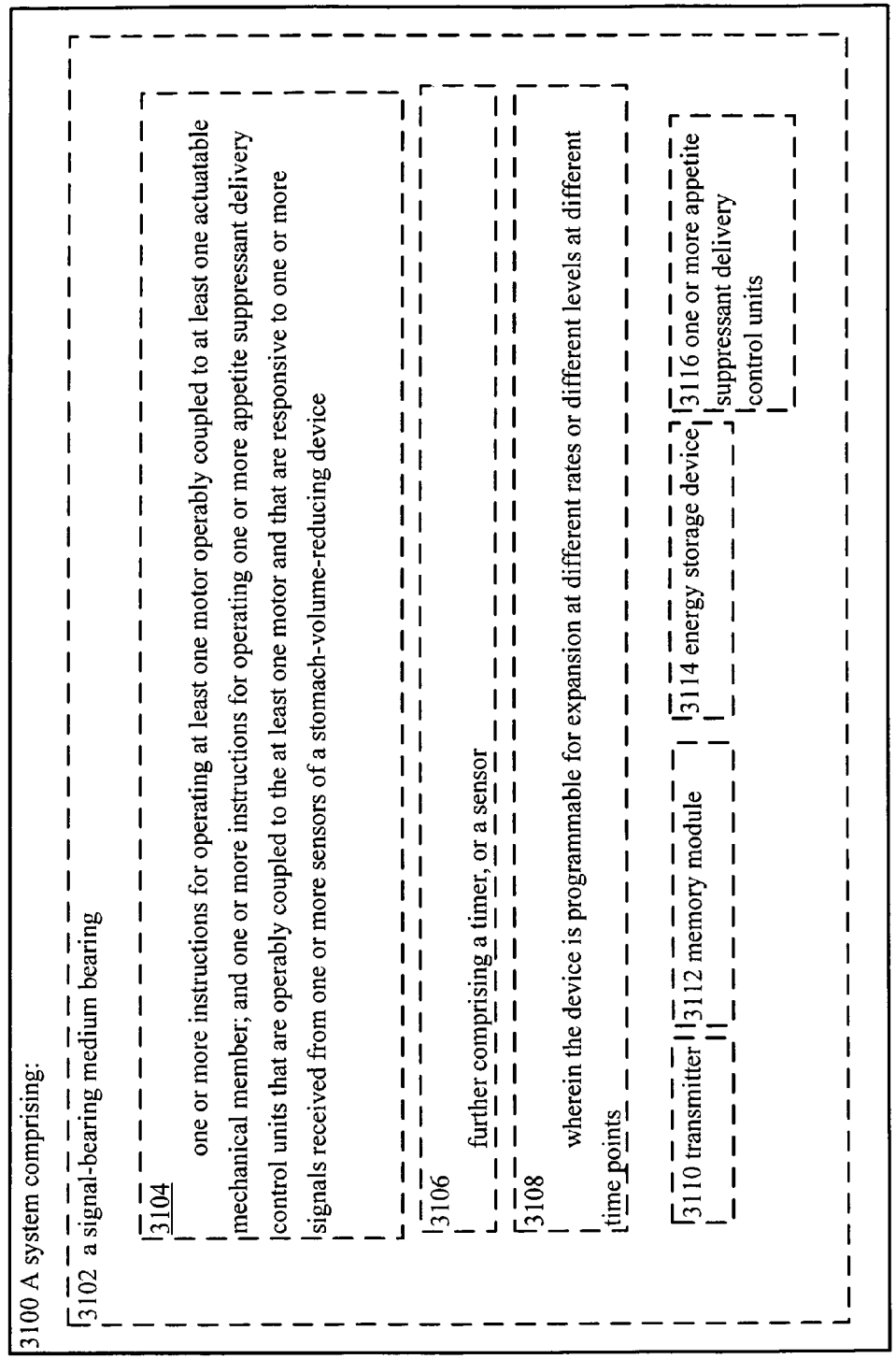
FIG. 31 illustrates a partial view of a particular embodiment of a system as described herein.

As illustrated in FIG. 31, in an embodiment 3100, a system comprises a signal-bearing medium 3102 bearing 3104 one or more instructions for operating at least one motor operably coupled to at least to one actuatable mechanical member; and one or more instructions for operating one or more appetite suppressant delivery control units that are operably coupled to the at least one motor and that are responsive to one or more signals received from one or more sensors of a stomach-volume-reducing device. In an embodiment 3106, the device further includes at least one timer or sensor. In an embodiment 3108, the device is programmable for expansion at different rates or different levels at different time points. In an embodiment, the device includes 3110 a transmitter. In an embodiment, the device includes 3112 a memory module. In an embodiment, the device includes 3114 an energy storage device. In an embodiment 3116 the device includes one or more hunger control delivery units.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, subjectly and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various embodiments described herein can be implemented, subjectly and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electromagnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, subjectly and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into an image processing system. Those having skill in the art will recognize that a typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that at least a portion of the devices and/or processes described herein can be integrated into a mote system. Those having skill in the art will recognize that a typical mote system generally includes one or more memories such as volatile or non-volatile memories, processors such as microprocessors or digital signal processors, computational entities such as operating systems, user interfaces, drivers, sensors, actuators, applications programs, one or more interaction devices (e.g., an antenna USB ports, acoustic ports, etc.), control systems including feedback loops and control motors (e.g., feedback for sensing or estimating position and/or velocity; control motors for moving and/or adjusting components and/or quantities). A mote system may be implemented utilizing suitable components, such as those found in mote computing/communication systems. Specific examples of such components entail such as Intel Corporation's and/or Crossbow Corporation's mote components and supporting hardware, software, and/or firmware.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). A sale of a system or method may likewise occur in a territory even if components of the system or method are located and/or used outside the territory.

Further, implementation of at least part of a system for performing a method in one territory does not preclude use of the system in another territory.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Those skilled in the art will appreciate that a user may be representative of a human user, a robotic user (e.g., computational entity), and/or substantially any combination thereof (e.g., a user may be assisted by one or more robotic agents) unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Various non-limiting embodiments are described herein as Prophetic Examples.

Prophetic Example 1

A pH-Responsive Intragastric Device to Induce Satiety

A pH-responsive stomach filling device is constructed from biodegradable polymer and a pH-sensitive hydrogel. The device is constructed with an expandable polymer envelope encasing hydrogel particles which expand under acidic conditions and contract under neutral conditions. A pH-responsive hydrogel synthesized with ionizable monomers, 2-dimethylaminoethyl methacrylate (DMAEMA) and N-isopropylacrylamide (NIPAM) is described (see e.g., Zhang et al., *Polymer* 50: 2516-2525, 2009, which is incorporated herein by reference). The hydrogel absorbs water and swells in response to acidic conditions, e.g., pH≤4, and collapses and frees water when the pH rises, e.g., pH≥7.5 or above. The hydrogel may swell approximately tenfold when the pH is decreased from approximately pH=8 to pH=4 at 37° C. Superporous hydrogels that display rapid (approximately 5 minutes or less) and reversible pH-dependent swelling may be synthesized using a freezedrying/gas blowing technique and glyoxal as a crosslinking agent. Methods and compositions to create reversibly swelling superporous hydrogels are described (see e.g., Gupta and Shivakumar, *DARU* 18(3): 200-210, 2010, which is incorporated herein by reference).

A flexible, long-lasting biodegradable envelope is fabricated to contain the pH-responsive hydrogel. In an embodiment, the long-lasting biodegradable envelope is time-dependent. The envelopes may be cylindrical and approximately 3 cm in length with a radius of approximately 1 cm. The envelopes contain a micropump and valves to control the flow of fluid in and out of the envelope. The flexible envelopes are constructed from a biodegradable material, for example a copolymer of lactide, glycolide, and caprolactone (see e.g., Bertleff et al., *J. Soc. Lap. Surg.* 13: 550-554, 2009, which is incorporated herein by reference), and contain a micropump and valves to allow pumping of fluid in and out of the envelope. A piezoelectric micropump is incorporated in the envelopes (e.g., Nanopump™ available from Debiotech S. A., Lausanne, Switzerland; see Tech Sheet: Implantable Nanopump™, which is incorporated herein by reference), and the envelopes are filled with approximately 9 cm$^3$ hydrogel particles. The micropump is controlled by circuitry and a battery integrated onto the Nanopump™ chip, and wireless signaling allows turning the pump on and off as required. The completed envelopes are sealed with biocompatible cyanoacrylate glue (Glubran 2 available from GEM, Viareggio, Italy).

To avoid gastric bypass surgery or other invasive procedures and yet reduce food consumption, a weight loss patient ingests 11 to 12 envelopes containing pH-responsive hydrogel. When the patient desires to increase his feeling of satiety, e.g., prior to a meal he ingests approximately 250 to 700 mL, up to 1000 mL acidic water, depending on degree of satiety desired. A wireless device is used to remotely actuate the micropumps on the envelopes to pump acidic stomach fluid into the lumen of the envelopes. After as long as 80 minutes, the pumps are turned off and the valves are closed. The hydrogel will swell in acidic stomach fluid (e.g., approximate pH=3) to as much as 10 times its original volume (i.e., approximately 90 mL per envelope). The total volume of the envelopes may be approximately 250 mL to 1 liter and likely to occupy approximately 20% to 90% of the available space in the stomach. In an embodiment, approximately 40% of the available space in the stomach is occupied by the stomach volume reducing device.

To eliminate discomfort from the swollen envelopes or to make room for a meal, the obese patient can reduce the volume of the envelopes by introducing a buffer solution at approximately pH=8 into the envelopes. Approximately 250 to 1000 mL of a sodium bicarbonate buffer solution at approximately pH≥8.0 is ingested by the patient and the micropumps on the envelopes are activated remotely to pump bicarbonate buffer solution into the envelopes. Neutralization of the hydrogel will free water from the hydrogel and allow the hydrogel to shrink. The freed water is pumped out of the envelopes, and they may contract to approximately ⅒ the volume, i.e., from about 90 mL to about 9 mL. The envelopes may shrink to cylinders approximately 3 cm long and 2 cm in diameter, a size that is likely to be retained in the stomach during peristalsis where a maximum particle size of approximately 2 mm is allowed passage through the pyloric valve. Alternatively, an intermediate degree of swelling/shrinking may be induced by consumption of a buffer solution at an intermediate pH, for example at pH=7 the swollen hydrogel may contract to approximately 70% of its volume at pH=4 (see e.g., Zhang et al., Ibid.). To reestablish satiety and stomach filling the patient may induce the envelopes in his stomach to swell again by ingesting acidic water and activating the micropump and valves on the envelopes. Repeated cycles of swelling and shrinking the envelopes may be induced by ingesting appropriate buffer solutions and actuating micropumps and valves to exchange buffer solutions between the stomach and envelopes.

The envelopes and the hydrogel particles they contain are biodegradable to guard against gastric obstruction and to allow periodic adjustment of the number of envelopes residing in the stomach. The envelopes are constructed of a biodegradable polymer, for example, lactide-glycolide-caprolactone (available from LGC, Polyganics, B. V. Groningen, Netherlands), and may undergo hydrolysis and degradation over a period of approximately 5 weeks (see e.g., Bertleff et al., Ibid.). Methods and compositions to make biodegradable polymers that degrade in weeks, months or years are described (see e.g., U.S. Pat. No. 7,919,112 B2 issued to Pathak et al. on Apr. 5, 2011, which is incorporated herein by reference). For example, a polymer envelope may be produced that degrades in 6 months following ingestion. Degradation of the envelope releases its hydrogel particles into the stomach fluid and allows the mechanical and chemical digestion of the hydrogel particles as well as the envelope. Degradation and digestion of the envelope and hydrogel particles facilitates their passage through the pyloric valve and ultimately excretion through the colon.

Prophetic Example 2

A Glucose-Responsive, pH-Sensitive Adherent Intragastric Device to Reduce Food Ingestion A moderately obese subject with a Body Mass Index of approximately 30, wishes to reduce his food intake without undergoing an invasive procedure. He is orally administered a stomach filling device which resides in the stomach. The device responds to a first chemical signal provided when the subject desires a feeling of satiety, for example a high level of glucose. The responsive device swells in the low pH environment of the stomach and thereby reduces the volume of the stomach. After a time, the glucose is catalytically degraded by enzymes in the responsive gel, where the oxygen-rich product aids in swelling properties. The device remains in a swollen state until the subject or his caregiver decides to reduce the volume of the device, whereupon a second signal, a buffer at pH=7.5, is given orally to cause the device to shrink. The device, enclosed in an envelope with valves and a minipump, may be swollen and shrunk multiple cycles, and may be swollen or shrunk to intermediate sizes, e.g., to 50% of maximum size.

A chemically responsive hydrogel is used to construct the stomach filling device, for example a glucose-responsive, pH-sensitive hydrogel that is activated by glucose and swells in low pH conditions. Preparation of a glucose-responsive, pH-sensitive hydrogel constructed has been described (see e.g., Podual et al., *Polymer* 41: 3975-3983, 2000, which is incorporated herein by reference). Briefly, two monomers, diethylaminoethyl methacrylate (DEAEM) and poly (ethylene glycol) monomethacrylate (PEGMA) are combined with a crosslinking agent, triethylene glycol dimethacrylate (TEGDMA), then a solution of the functionalized enzymes glucose oxidase and catalase, and containing the binding agent acryloyl chloride, is added to the comonomer mixture. The resulting copolymer is dried in a vacuum oven and enveloped in elastic, biodegradable polymeric envelopes.

An elastic biodegradable envelope is fabricated to contain the glucose-responsive, pH-sensitive hydrogel and isolate it from gastric fluid. Each envelope may be cylindrical and approximately 3 cm in length with a radius of approximately 1 cm. The envelopes each contain a micropump and valves to control the flow of fluid in and out of the envelope. The flexible envelopes are constructed from a time-dependent biodegradable material, for example, a copolymer of lactide, glycolide and caprolactone (see e.g., Bertleff et al., *J. Soc. Lap. Surg.* 13: 550-554, 2009, which is incorporated herein by reference). To promote retention in the stomach, the envelope also contains chitosan, a cationic polysaccharide, which adheres to the mucosal surface. Methods and compositions to incorporate chitosan in polymers are described (see e.g., U.S. Pat. No. 7,919,293 B2 issued to Sung et al. on Apr. 5, 2011 which is incorporated herein by reference). The envelopes are filled with approximately 9 cm$^3$ hydrogel particles, and they contain a micropump and valves to allow pumping fluid in and out of the envelope. A piezoelectric micropump is incorporated in the envelopes (e.g., Nanopump™ available from Debiotech S. A., Lausanne, Switzerland: see Tech Sheet: Implantable Nanopump™, which is incorporated herein by reference). The micropump is controlled by circuitry and a battery integrated onto the Nanopump™ chip, and wireless signaling allows turning the pump on and off as required. The completed envelopes are sealed with biocompatible cyanoacrylate glue (Glubran 2 available from GEM, Viareggio, Italy).

To induce satiety and reduce food consumption, the overweight subject ingests 11 to 12 envelopes containing the glucose-responsive, pH-sensitive hydrogel and, prior to a meal, ingests approximately 250-1000 mL, depending on desired satiety, of 0.1 M Dextrose in saline at pH=6.5. Shortly afterward (approximately 1-2 minutes later) a wireless device is used to remotely actuate the optional micropumps on the envelopes to pump the acidic buffer and stomach fluid into the lumen of the envelopes. After as long as 80 minutes the pumps are turned off and the valves are closed. The hydrogel, in the presence of the glucose, will hydrate and swell in acidic fluid (e.g., approximate pH<7) to as much as 10 times its volume (i.e., approximately 90 mL per envelope). The total volume of the envelopes may be approximately 250 mL-1 liter and likely to occupy approximately 20% to 90% of the available space in the stomach. The envelopes may adhere to the stomach mucosa by virtue of the chitosan they contain.

To remove discomfort from the swollen envelopes or to make room for a meal, the subject patient can reduce the volume of the envelopes by introducing a buffer solution at approximately pH=7.4 into the envelopes. Approximately 250-1000 mL of a sodium bicarbonate buffer solution at approximately pH≥7.4 is ingested by the patient. In the absence of glucose, which has been degraded by the immobilized enzyme in the hydrogel, neutralization of the hydrogel will free water from the hydrogel and allow the hydrogel to shrink as much as tenfold by weight (See e.g., Podual et al., Ibid.). The device may contract to approximately $^1$/$_{10}$ their volume, i.e., from about 90 mL to about 9 mL. The shrunken envelopes may remain adhered to the gastric mucosa through binding by chitosan present in the envelopes. Alternatively, an intermediate degree of swelling/shrinking may be induced by consumption of a buffer solution at an intermediate pH, for example at pH=7, and the swollen hydrogel may contract to approximately 50% of its maximum volume at pH=6.5 (see e.g., Podual et al., Ibid.). To reestablish satiety and stomach filling, the patient may induce the envelopes in his stomach to swell again by ingesting acidic water and activating the micropump and valves on the envelopes. Repeated cycles of swelling and shrinking the envelopes may be induced by ingesting various amounts of appropriate buffer solutions and optional actuating micropumps and valves to exchange buffer solutions between the stomach and envelopes.

The envelopes and the hydrogel particles they contain are biodegradable to guard against gastric obstruction and to allow periodic adjustment of the number of envelopes residing in the stomach. The envelopes are constructed of a biodegradable polymer, for example, lactide-glycolide-caprolactone (available from LGC, Polyganics, B. V. Groningen, Netherlands), and undergo hydrolysis and degradation over a period of approximately 5 weeks (see e.g., Bertleff et al., Ibid.). Methods and compositions to make biodegradable polymers that degrade in weeks, months or years are described (see e.g., U.S. Pat. No. 7,919,112 B2 issued to Pathak et al. on Apr. 5, 2011 which is incorporated herein by reference). For example a polymer envelope may be produced which degrades in 1 year following ingestion. Degradation of the envelope releases its hydrogel particles into the stomach fluid and allows the mechanical and chemical digestion of the hydrogel particles as well as the envelope. Degradation and digestion of the envelope and hydrogel particles facilitates their passage through the pyloric valve and ultimately excretion through the colon. See FIG. 1.

For example, as already stated, FIG. 1 illustrates an embodiment in which a reversibly responsive expandable housing device is a polymer envelope that is encasing glucose-responsive, pH-sensitive hydrogel particles. A portion of the hydrogel particles or a subset of the ingested envelopes may include, within the glucose-responsive, pH-sensitive hydrogel, an appetite suppressant that is released upon the gel swelling in response to the glucose and in the presence of low pH. Further, the device includes a microchip, piezoelectric pump, a port 144 that may be operably associated with a sensor for sensing at least one environmental condition of the subject's stomach, and one or more microvalves.

Prophetic Example 3

An Automatic Intragastric Device Responsive to a Provided Chemical and to External Wireless Signals An automatic stomach filling device is implanted in the stomach of an obese patient to induce satiety and reduce food intake. A responsive, reversibly responsive expandable, stomach-filling device is attached to the stomach wall of the patient and will potentially occupy approximately 0.4 L to 4 L in the stomach. The device expands or contracts in response to signals from a microsensor able to detect a chemical in the stomach. The stomach filling device may also be controlled manually using an external remote via a wireless signal. The device may be expanded or contracted to occupy variable volumes representing 10% to 100% of the subject's maximal stomach volume.

The intragastric device contains multiple "umbrella-like" devices that expand and contract by virtue of piezo-electric motors which raise or lower space-filling "umbrellas," (e.g. mechanical members or true stretchers and ribs as in the mechanics of an umbrella). The devices contain two ellipsoid space fillers (umbrellas) and four member rods that are driven by four piezo-electric motors 156. See FIG. 2. The ellipsoid umbrellas and member rods are constructed from a long-lasting biodegradable material, for example, a copolymer of lactide, glycolide and caprolactone (see e.g., Bertleff et al., *J. Soc. Lap. Surg.* 13: 550-554, 2009, which is incorporated herein by reference). Piezo-electric motors 2.8×2.8×6 mm with a thrust speed of approximately 10 mm/sec are available from New Scale Technologies Inc., Victor, N.Y., and are powered by 2.3 volts DC. The umbrella devices each include control circuitry (e.g., a microchip), which responds to electrical signals from chemical-detecting microsensors and actuates the piezo-electric motors 156. Alternatively the piezo-electric motors 156 are controlled manually by signaling from an external wireless remote.

The chemical-detecting microsensor is a surface acoustic wave sensor that includes a piezoelectric layer, or piezoelectric substrate, a hydrogel located on the surface of the sensor with a molecular recognition component within the hydrogel capable of detecting the chemical, and input and output transducer(s). The molecular recognition component is a nucleic acid analog immobilized in the hydrogel and having a backbone comprising phosphoramide. The probe nucleic acid analog specifically recognizes and binds to a provided chemical that is a peptide nucleic acid. The provided chemical is ingested in a gelatin capsule together with an aqueous liquid, and the gelatin capsule quickly dissolves. Binding of the provided chemical by the probe recognition element alters the phase of the hydrogel, and this change is detected as a change in a property of the propagating surface acoustic wave. The surface acoustic wave generated within the piezoelectric layer is detected by interdigitated electrodes and transduced by the output transducer into an electrical signal, which is transmitted via the control circuitry to the umbrella device. A chemical-detecting surface acoustic wave microsensor with responsive hydrogel is described in U.S. Patent App. Pub. No. 2006/0024813, which is incorporated herein by reference.

Multiple umbrella devices are enveloped in a flexible polymer envelope, which may be fabricated from silicone. The envelope may be fabricated to fit the subject's stomach. Imaging of the stomach using magnetic resonance imaging, computed tomography, or other techniques can be used to model the subject's stomach shape and create an envelope to occupy approximately 10% of maximal stomach volume (e.g., approximately 0.4 L for stomach with maximum volume of 4 L). A three-dimensional printer (available from Z Corporation, Burlington, Mass.) may be used to produce a mandrel for generating the envelope. Fabrication of silicone balloons is described (See e.g., U.S. Patent App. Pub. No. 2007/0100368 by Quijano et al., which is incorporated herein by reference). Approximately 40 umbrella devices, which occupy approximately 0.4 L in the contracted state (see FIG. 2), are placed in the silicone envelope, and the envelope is sealed with biocompatible cyanoacrylate glue (Glubran 2 available from GEM, Viareggio, Italy).

For example, as already indicated, FIG. 2 illustrates a reversibly responsive expandable device housing that is, in this embodiment, a non-toxic polymer envelope encasing an actuatable mechanical member (truss rod, as noted other actuatable mechanical members can be used). As illustrated in FIG. 2, the actuatable mechanical members are moveable by at least one piezoelectric motor. In addition, the device includes a motor control chip (operably coupled to control circuitry) and an ellipsoid space filler. In an embodiment, a sensor is operably coupled to at least one of the actuatable mechanical member, or the motor.

The completed intragastric device is implanted using an endoscopic tube and a sheath to compress the device. Methods to compress stomach filling devices and implant them using endoscopy are described (See e.g., U.S. Patent App. Pub. No. 2007/0100368 Ibid.). The intragastric device is attached to the stomach wall using sutures introduced by endoscopic methods. Methods and devices to suture the stomach wall are described (see e.g., Swanstrom et al. *The Permanente Journal* 12: 42-47, 2008, which is incorporated herein by reference). The intragastric device may be removed by an endoscopic procedure that includes cutting the sutures to the stomach and retrieving the device using a sheath and retrieval tool (see e.g., U.S. Patent App. Pub. No. 2007/0100368 Ibid.).

To reduce food ingestion, the intragastric device expands automatically in response to electrical signals from the chemical-detecting sensor. See FIG. 3. For example, FIG. 3 illustrates a stomach volume reducing device in a collapsed state (FIG. 3A), as well as in an expanded state (FIG. 3B). For example, the chemical is ingested prior to an expected meal, and the chemical-detecting sensor, after detecting the chemical, transmits an electrical signal to the umbrella-like devices to actuate the piezo-electric motors, erect the ellipsoid space fillers, and expand the space filling device to occupy approximately 70% of the stomach volume. The chemical-detecting sensor may also signal to reduce the space filling volume, i.e., contract the device, when the chemical has dissipated from the gel over time and no additional chemical is detected, or after a predetermined time (e.g., 2-3 hours following eating or signaling). An external remote control may be used to reduce or increase the volume of the device to variable degrees. For example, the subject may use the external remote control to respond to gastric discomfort or make room for a meal by reducing the volume of the device. Alternatively, the external remote may be used to increase the feeling of fullness or to fill an expanded stomach by increasing the volume of the device. See FIG. 2.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device, comprising:
   a reversibly responsive expandable device housing configured to reversibly expand or contract and primarily reside in the stomach of a subject;
   at least one member motor;
   at least one actuatable mechanical member operably coupled to each of the at least one member motor and the housing; and
   at least one crystalline colloidal array sensor operably coupled to the at least one member motor and configured to detect at least one chemical in the stomach of the subject.

2. The device of claim 1, wherein the device resides solely in the stomach of the subject.

3. The device of claim 1, wherein the device is attached to the gastric wall of the subject.

4. The device of claim 1, further including at least one energy storage device operably coupled to the at least one motor.

5. The device of claim 4, wherein the energy storage device includes at least one battery.

6. The device of claim 1, wherein the at least one sensor includes at least one chemical sensor.

7. The device of claim 1, wherein the at least one actuatable mechanical member includes at least one linear displacement actuator within the member.

8. The device of claim 1, further including at least one wireless remote controller operably coupled to the at least one motor.

9. The device of claim 1, wherein the at least one reversibly responsive expandable device housing is fabricated from a first polymer, and encasing chemical responsive particles made from a second polymer;
   the reversibly responsive expandable device housing including at least one port; and
   at least one controllable micropump or controllable valve operably connected to the at least one port.

10. The device of claim 1, wherein the at least one hunger control delivery reservoir operably coupled to the at least one reservoir motor includes one or more appetite suppressant delivery control units.

11. The device of claim 10, wherein the one or more appetite suppressant delivery control units act substantially autonomously.

12. The device of claim 10, wherein the one or more appetite suppressant delivery control units are configured to receive one or more signals substantially continuously from one or more appetite suppressant delivery sensors.

13. The device of claim 10, wherein the one or more appetite suppressant delivery control units are configured to receive one or more signals that include information related to one or more concentrations of at least one chemical within a subject.

14. The device of claim 1, further including a timer.

15. The device of claim 14, further including a timer transmitter operably coupled to the at least one motor.

16. The device of claim 15, wherein the at least one motor is operably coupled to a receiver.

17. The device of claim 15, wherein the motor is responsive to signals received from the timer transmitter.

18. A device, comprising:
   a reversibly responsive expandable device housing configured to reversibly expand or contract and primarily reside in the stomach of a subject;
   at least one controllable ratchet member or extendable ladder member operably coupled to the housing;
   at least one member motor operably coupled to the at least one controllable ratchet member or controllable extendable ladder member;
   at least one controller operably coupled to the at least one member motor and configured to increase or decrease the length of the controllable ratchet or controllable extendable ladder member; and
   at least one hunger control delivery reservoir operably coupled to at least one reservoir motor, and configured to receive one or more signals from at least one internal or external interface.

19. The device of claim 18, wherein the device resides solely in the stomach of a subject.

20. The device of claim 18, wherein the device is attached to the gastric wall of the subject.

21. The device of claim 18, wherein the at least one controllable ratchet member or controllable extendable ladder member is configured to receive one or more signals from one or more internal or external interfaces.

22. The device of claim 18, wherein the at least one controllable ratchet member or controllable extendable ladder member includes one or more member control units.

23. The device of claim 22, wherein the one or more member control units act substantially autonomously.

24. The device of claim 22, wherein the one or more member control units are configured to receive one or more signals substantially continuously from one or more member sensors.

25. A system, comprising:
   a stomach-volume-reducing device including a reversibly responsive expandable device housing configured to reversibly expand or contract and primarily reside in the stomach of a subject;
   at least one motor;
   at least one actuatable mechanical member operably coupled to each of the at least one motor and the housing;
   one or more appetite suppressant delivery control units operably coupled to the at least one motor and that are responsive to one or more signals received from one or more sensors of a stomach-volume-reducing device; and
   circuitry configured to operate the at least one motor; and
   circuitry configured to operate the one or more appetite suppressant delivery control units.

26. A system, comprising:
- a stomach-volume-reducing device, including
  - a reversibly responsive expandable device housing configured to reversibly expand or contract and attach to a gastric wall of a subject, at least one actuatable mechanical member;
  - at least one motor operably coupled to the at least one actuatable mechanical member;
  - at least one crystalline colloidal array sensor operably coupled to the at least one motor and configured to detect one or more electrical signals originating from a subject; and
  - control circuitry operably coupled to the stomach-volume-reducing device, the control circuitry configured to operate the at least one motor responsive to receiving one or more signals from the at least one sensor.

27. The system of claim 26, wherein the at least one sensor is operably coupled to the at least one motor and is configured to wirelessly communicate the sensed one or more electrical signals originating from the subject.

28. The system of claim 26, wherein the at least one sensor is electrically or optically coupled to the control circuitry to communicate the one or more signals thereto.

29. The system of claim 26, wherein the control circuitry is configured to determine when to engage the at least one motor.

30. The system of claim 26, further including at least one controller configured to activate expansion of the stomach-volume-reducing device responsive to the control circuitry determining that the at least one reversibly responsive expandable stomach-volume-reducing device is to be deployed.

31. The system of claim 30, wherein the at least one controller is configured to activate expansion of the stomach-volume-reducing device to a programmed level of expansion.

32. The system of claim 26, wherein the control circuitry operably coupled to the stomach-volume-reducing device configured to operate the at least one motor responsive to receiving one or more signals from the at least one sensor is configured to actuate the at least one actuatable mechanical member operably coupled to the at least one motor.

33. The system of claim 26, further including a first data transmitter coupled to the control circuitry, the first data transmitter configured to transmit information at least related to data encoded in the one or more sensed electrical signals of the subject.

34. The system of claim 33, wherein the first data transmitter is configured to wirelessly transmit the information.

35. The system of claim 26, wherein the control circuitry is programmable.

36. The system of claim 35, wherein the device is programmable for expansion of about 5%, about 10%, about 15%, about 20%, about 30%, about 40%, about 50%, about 60%, about 70%, about 80%, about 90%, about 100%, or any value less than or therebetween.

37. The system of claim 26, wherein the control circuitry is configured to direct a data transmitter to transmit the information to a third party or a second device.

38. The system of claim 37, wherein the second device includes a second stomach-volume-reducing device.

39. The system of claim 26, further including a memory module configured to store data encoded in the one or more sensed electrical signals of the subject.

40. The system of claim 26, further including a timer.

41. The system of claim 26, further including circuitry configured to operate one or more appetite suppressant delivery control units that are operably coupled to the at least one motor and that is responsive to one or more signals received from one or more sensors of the stomach-volume reducing device.

42. The system of claim 26, further including circuitry configured to operate one or more appetite suppressant delivery control units that are operably coupled to one or more receivers that are configured to receive one or more signals that include information related to at least one chemical within a subject.

43. The system of claim 26, further including circuitry configured to operate one or more ports in the stomach-volume-reducing device.

44. The system of claim 26, further including circuitry configured to operate the reversibly responsive expandable device housing.

* * * * *